US009447394B2

(12) United States Patent
Armstrong

(10) Patent No.: US 9,447,394 B2

(45) Date of Patent: *Sep. 20, 2016

(54) METHODS AND COMPOSITIONS FOR TREATMENT OF MYOTUBULAR MYOPATHY USING CHIMERIC POLYPEPTIDES COMPRISING MYOTUBULARIN 1(MTM1) POLYPEPTIDES

(71) Applicant: Valerion Therapeutics, LLC, Concord, MA (US)

(72) Inventor: Dustin D. Armstrong, Quincy, MA (US)

(73) Assignee: Valerion Therapeutics, LLC, Concord, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/485,524

(22) Filed: Sep. 12, 2014

(65) Prior Publication Data

US 2015/0218540 A1 Aug. 6, 2015

Related U.S. Application Data

(63) Continuation of application No. 13/378,283, filed as application No. PCT/US2010/038703 on Jun. 15, 2010, now Pat. No. 8,834,866.

(60) Provisional application No. 61/268,732, filed on Jun. 15, 2009.

(51) Int. Cl.

| | |
|---|---|
| ***C07K 16/28*** | (2006.01) |
| ***C12N 9/00*** | (2006.01) |
| ***C12N 9/16*** | (2006.01) |
| ***A61K 47/48*** | (2006.01) |
| ***C07K 16/44*** | (2006.01) |
| *A61K 38/00* | (2006.01) |
| *A61K 39/00* | (2006.01) |

(52) U.S. Cl.

CPC .......... *C12N 9/16* (2013.01); *A61K 47/48415* (2013.01); *A61K 47/48507* (2013.01); *C07K 16/28* (2013.01); *C07K 16/44* (2013.01); *A61K 38/00* (2013.01); *A61K 2039/505* (2013.01); *C07K 2317/24* (2013.01); *C07K 2317/54* (2013.01); *C07K 2317/55* (2013.01); *C07K 2317/56* (2013.01); *C07K 2317/77* (2013.01); *C07K 2319/00* (2013.01); *C07K 2319/33* (2013.01); *C12Y 301/03064* (2013.01)

(58) Field of Classification Search

CPC .... C12N 9/00; C12N 9/96; A61K 2039/505; C07K 16/28; C07K 2319/01; C07K 2319/33

USPC .................... 424/94.3, 152.1; 435/188, 69.7; 536/23.2, 23.4

See application file for complete search history.

(56) References Cited

U.S. PATENT DOCUMENTS

| | | | |
|---|---|---|---|
| 5,622,699 | A | 4/1997 | Ruoslahti et al. |
| 6,068,829 | A | 5/2000 | Ruoslahti et al. |
| 6,124,447 | A | 9/2000 | Natori |
| 6,174,687 | B1 | 1/2001 | Rajotte et al. |
| 6,180,084 | B1 | 1/2001 | Ruoslahti et al. |
| 6,232,287 | B1 | 5/2001 | Ruoslahti et al. |
| 6,296,832 | B1 | 10/2001 | Ruoslahti et al. |
| 6,303,573 | B1 | 10/2001 | Ruoslahti et al. |
| 6,306,365 | B1 | 10/2001 | Ruoslahti et al. |
| 6,692,949 | B2 | 2/2004 | Yan et al. |
| 7,189,396 | B1 | 3/2007 | Weisbart |
| 8,609,615 | B2 | 12/2013 | Armstrong |
| 8,834,866 | B2 | 9/2014 | Armstrong |
| 2008/0292618 | A1 | 11/2008 | Weisbart |
| 2010/0111977 | A1 | 5/2010 | Armstrong |
| 2010/0143358 | A1 | 6/2010 | Weisbart |

FOREIGN PATENT DOCUMENTS

| | | | |
|---|---|---|---|
| WO | WO-97/32602 | A1 | 9/1997 |
| WO | WO-98/53804 | | 12/1998 |
| WO | WO-2005/115439 | A2 | 12/2005 |
| WO | WO-2008/091911 | A2 | 7/2008 |
| WO | WO-2008/148063 | A1 | 12/2008 |
| WO | WO-2010/044894 | | 4/2010 |
| WO | WO-2010/138769 | A1 | 12/2010 |
| WO | WO-2013/177428 | A1 | 11/2013 |

OTHER PUBLICATIONS

Hansen et al., "Antibody-Mediated Transduction of Therapeutic Proteins into Living Cells," The Scientific World, vol. 5: 782-788 (2005).

Abhinandan, K. R., et al., "Analyzing the "Degree of Humanness" of Antibody Sequences," Journal of Mol. Biol., 369:852-862 (2007).

Blondeau, F., et al., "Myotubularin, a Phosphatase Deficient in Myotubular Myopathy, Acts on Phosphatidylinositol 3-kinase and Phosphatidylinositol 3-phosphate Pathway," Human Molecular Genetics, 9(15):2223-2229 (2000).

Buj-Bello, A., et al., "AAV-Mediated Intramuscular Delivery of Myotubularin Corrects the Myotubular Myopathy Phenotype in Targed Murine Muscle and Suggests a Function in Plasma Membrane Homeostasis," Human Molecular Genetics, 17(14):2132-2143 (2008).

(Continued)

*Primary Examiner* — Karen Cochrane Carlson

(74) *Attorney, Agent, or Firm* — Ropes & Gray LLP

(57) ABSTRACT

The present invention provides chimeric polypeptides comprising myotubularin 1 (MTMI) polypeptides and an internalizing moiety, wherein, the moiety can be an antibody, and is preferably monoclonal antibody 3E10, a functional variant or a fragment thereof. One aspect of the present invention provides compositions comprising these chimeric polypeptides together with a pharmaceutically acceptable carrier, and optionally, a further therapeutic agent. Another aspect of the present invention provides methods of treating Myotubular Myopathy comprising administering the polypeptides or compositions comprising the polypeptides to a subject in need.

27 Claims, No Drawings

(56) References Cited

OTHER PUBLICATIONS

Buj-Bello, A., et al., "The Lipid Phosphatase Myotubularin is Essential for Skeletal Muscle Maintenance but not for Myogenesis in Mice," PNAS, 99(23):15060-15065 (2002).
Cao, C., et al., "Myotubularin Lipid Phosphatase Binds the hVPS15/hVPS34 Lipid Kinase Complex on Endosomes," Traffic, 8:1052-1067 (2007).
Chaussade, C., et al., "Expression of Myotubularin by an Adenoviral Vector Demonstrates Its Function as a Phosphatidylinositol 3-Phosphate [PtdIns(3)*P*] Phosphatase in Muscle Cell Lines: Involvement of PtdIns(3)*P* in Insulin-Stimulated Glucose Transport," 17(12):2448-2460 (2003).
Fili, N., et al., "Compartmental Signal Modulation: Endosomal Phosphatidylinositol 3-Phospate Controls Endosome Morphology and Selective Cargo Sorting," PNAS, 103(42):15473-15478 (2006).
Hansen, J. E., et al., "Antibody-Mediated Hsp70 Protein Therapy," Brain Research, 1088:187-196 (2006).
Hansen, J. E., et al., "Intranuclear Protein Transduction through a Nucleoside Salvage Pathway*," Journal of Biological Chemistry, 282(29):20790-20793 (2007).
Herman, G. E., et al., "Medical Complications in Long-Term Survivors with X-Linked Myotubular Myopathy," The Journal of Pediatrics, 134(2):206-214 (1999).
International Search Report from PCT/US2010/038703 dated Aug. 25, 2010.
Kim, S., et al., "Myotubularin and MTMR2, Phosphatidylinositol 3-Phosphatases Mutated in Myotubular Myopathy and Type 4B Charcot-Marie-Tooth Disease," The Journal of Biological Chemistry, 277(6):4526-4531 (2002).
Kolvunen, E., et al., "Phage Libraries Displaying Cyclic Peptides with Different Ring Sizes: Ligand Specifications of the RGD-Directed Integrins," Bio/Technology, 13:265-270.
Laporte et al., "Mutations in the MTM1 gene implicated in X-linked myotubular myopathy," Human Molecular Genetics, vol. 6(9), pp. 1505-1511 (1997).
Laporte, J., et al., "MTM1 Mutations in X-Linked Myotubular Myopathy," Human Mutation, 15:393-409 (2000).
Laporte, J., et al., "Myotubularins, a Large Disease-Associated Family of Cooperating Catalytically Active and Inactive Phosphoinositides Phosphatases," Human Molecular Genetics, 12(2):R285-R292 (2003).
Laporte, J., et al., "The PtdIns3*P* Phosphatase Myotubularin is a Cytoplasmic Protein that also Localizes to Rac1-Inducible Plasma Membrane Ruffles," Journal of Cell Science, 115:3105-3117 (2002).
Lawlor et al., "Enzyme replacement therapy rescues weakness and improves muscle pathology in mice with X-linked myotubular myopathy," Human Molecular Genetics, vol. 22(8): 1525-1538 (2013).
Lorenzo, O., et al., "Systematic Analysis of Myotubularins: Heteromeric Interactions, Subcellular Localisation and Endosome-Related Functions," Journal of Cell Science, 119:2953-2959 (2006).
Mankodi, A., et al., "Expanded CUG Repeats Trigger Aberrant Splicing of ClC-1 Chloride Channel Pre-mRNA and Hyperexcitability of Skeletal Muscle in Myotonic Dystrophy," Molecular Cell, 10:35-44 (2002).
NCBI GenBank Accession No. NM_000252.2 dated Apr. 26, 2009.
NCBI GenBank Accession No. NM_001013047.1 dated Oct. 24, 2008.
NCBI GenBank Accession No. NM_019926.2 dated Jan. 25, 2009.
NCBI GenBank Accession No. NP_000243.1 dated Apr. 26, 2009.
NCBI GenBank Accession No. NP_001013065.1 dated Oct. 24, 2008.
NCBI GenBank Accession No. NP_064310.1 dated Jan. 25, 2009.
Pasqualini, R., et al., "A Peptide Isolated from Phage Display Libraries is a Structural and Functional Mimic of an RGD-binding Site on Integrins," The Journal of Cell Biology, 130(5):1189-1196 (1995).
Pasqualini, R., et al., "Organ Targeting in vivo Using Phage Display Peptide Libraries," 380:364-366 (1996).
Pasqualini, R., et al., "Searching for a Molecular Address in the Brain," Molecular Psychiatry, 1:421-422 (1996).
Pennycooke, M., et al., "Differential Expression of Human Nucleoside Transporters in Normal and Tumor Tissue," Biochemical and Biophysical Research Communications, 280:951-959 (2001).
Pierson, C, et al., "Myofiber Size Correlates with *MTM1* Mutation Type and Outcome in X-linked Myotubular Myopathy," 17(7):562-568 (2007).
Rajotte, D., et al., "Membrane Dipeptidase is the Receptor for a Lung-Targeting Peptide Identified by in Vivo Phage Display," The Journal of Biological Chemistry, 274(17):11593-11598 (1999).
Rajotte, D., et al., "Molecular Heterogeneity of the Vascular Endothelium Revealed by In Vivo Phage Display," J. Clin. Invest., 102(2):430-437 (1998).
Robinson, F. L., et al., "Myotubularin Phosphatases: Policing 3-Phosphoinositides," TRENDS in Cell Biology, 16(8):403-412 (2006).
Samoylova, T. I., et al.., "Elucidation of Muscle-Binding Peptides by Phage Display Screening," Muscle & Nerve, 22:460-466 (1999).
Schaletzky, J., et al., "Phosphatidylinositol-5-Phospate Activation and Conserved Substrate Specificity of the Myotubularin Phosphatidylinositol 3-Phosphatases," Current Biology 13:504-509 (2003).
Sharma, K. R., et al., "Clinical and Electromyographic Deep Tendon Reflexes in Polyneuropathy: Diagnostic Value and Prevalence," Acta Neurologica Scandinavica, 119:224-232 (2009).
Taylor, G. S., et al., "Myotubularin, a Protein Tyrosine Phosphatase Mutated in Myotubular Myopahty, Dephosphorylates the Lipid Second Messenger, Phosphatidylinositol 3-Phosphate," PNAS, 97(16):8910-8915 (2000).
Weisbart, R., et al., "An Autoantibody is Modified for Use as a Delivery System to Target the Cell Nucleus: Therapeutic Implications," Journal of Autoimmunity, 11:539-546 (1998).
Weisbart, R., et al., "An Intracellular Delivery Vehicle for Protein Transduction of Micro-Dystrophin," Journal of Drug Targeting, 13(2):81-87 (2005).
Weisbart, R., et al., "Cell Type Specific Targeted Intracellular Delivery Into Muscle of a Monoclonal Antibody that Binds Myosin IIb," Molecular Immunology, 39:783-789 (2003).
Weisbart, R., et al., Novel Protein Transfection fo Primary Rat Cortical Neurons Using an Antibody that Penetrate Living Cells, Journal of Immunology, 164(11):6020-2026 (2000).
Weisbart, R., et al., "Nuclear Delivery of p53 C-terminal Peptides into Cancer Cells Using scFv Fragments of a Monoclonal Antibody that Penetrates Living Cells," Cancer Letters, 195:211-219 (2003).
Zack et al., "Mechanisms of Cellular Penetration and Nuclear Localization of an Anti-Double Strand DNA Autoantibody," Journal of Immunology, 157(5):2082-2088 (1996).

SEQUENCE LISTING

<160> NUMBER OF SEQ ID NOS: 14

<210> SEQ ID NO 1
<211> LENGTH: 603
<212> TYPE: PRT
<213> ORGANISM: Homo sapiens

<400> SEQUENCE: 1

```
Met Ala Ser Ala Ser Thr Ser Lys Tyr Asn Ser His Ser Leu Glu Asn
1               5                   10                  15

Glu Ser Ile Lys Arg Thr Ser Arg Asp Gly Val Asn Arg Asp Leu Thr
            20                  25                  30

Glu Ala Val Pro Arg Leu Pro Gly Glu Thr Leu Ile Thr Asp Lys Glu
        35                  40                  45

Val Ile Tyr Ile Cys Pro Phe Asn Gly Pro Ile Lys Gly Arg Val Tyr
    50                  55                  60

Ile Thr Asn Tyr Arg Leu Tyr Leu Arg Ser Leu Glu Thr Asp Ser Ser
65                  70                  75                  80
```

-continued

```
Leu Ile Leu Asp Val Pro Leu Gly Val Ile Ser Arg Ile Glu Lys Met
                85                  90                  95

Gly Gly Ala Thr Ser Arg Gly Glu Asn Ser Tyr Gly Leu Asp Ile Thr
            100                 105                 110

Cys Lys Asp Met Arg Asn Leu Arg Phe Ala Leu Lys Gln Glu Gly His
        115                 120                 125

Ser Arg Arg Asp Met Phe Glu Ile Leu Thr Arg Tyr Ala Phe Pro Leu
    130                 135                 140

Ala His Ser Leu Pro Leu Phe Ala Phe Leu Asn Glu Glu Lys Phe Asn
145                 150                 155                 160

Val Asp Gly Trp Thr Val Tyr Asn Pro Val Glu Glu Tyr Arg Arg Gln
                165                 170                 175

Gly Leu Pro Asn His His Trp Arg Ile Thr Phe Ile Asn Lys Cys Tyr
            180                 185                 190

Glu Leu Cys Asp Thr Tyr Pro Ala Leu Leu Val Val Pro Tyr Arg Ala
        195                 200                 205

Ser Asp Asp Asp Leu Arg Arg Val Ala Thr Phe Arg Ser Arg Asn Arg
    210                 215                 220

Ile Pro Val Leu Ser Trp Ile His Pro Glu Asn Lys Thr Val Ile Val
225                 230                 235                 240

Arg Cys Ser Gln Pro Leu Val Gly Met Ser Gly Lys Arg Asn Lys Asp
                245                 250                 255

Asp Glu Lys Tyr Leu Asp Val Ile Arg Glu Thr Asn Lys Gln Ile Ser
            260                 265                 270

Lys Leu Thr Ile Tyr Asp Ala Arg Pro Ser Val Asn Ala Val Ala Asn
        275                 280                 285

Lys Ala Thr Gly Gly Gly Tyr Glu Ser Asp Asp Ala Tyr His Asn Ala
    290                 295                 300

Glu Leu Phe Phe Leu Asp Ile His Asn Ile His Val Met Arg Glu Ser
305                 310                 315                 320

Leu Lys Lys Val Lys Asp Ile Val Tyr Pro Asn Val Glu Glu Ser His
                325                 330                 335

Trp Leu Ser Ser Leu Glu Ser Thr His Trp Leu Glu His Ile Lys Leu
            340                 345                 350

Val Leu Thr Gly Ala Ile Gln Val Ala Asp Lys Val Ser Ser Gly Lys
        355                 360                 365

Ser Ser Val Leu Val His Cys Ser Asp Gly Trp Asp Arg Thr Ala Gln
    370                 375                 380

Leu Thr Ser Leu Ala Met Leu Met Leu Asp Ser Phe Tyr Arg Ser Ile
385                 390                 395                 400

Glu Gly Phe Glu Ile Leu Val Gln Lys Lys Trp Ile Ser Phe Gly His
                405                 410                 415

Lys Phe Ala Ser Arg Ile Gly His Gly Asp Lys Asn His Thr Asp Ala
            420                 425                 430

Asp Arg Ser Pro Ile Phe Leu Gln Phe Ile Asp Cys Val Trp Gln Met
        435                 440                 445

Ser Lys Gln Phe Pro Thr Ala Phe Glu Phe Asn Glu Gln Phe Leu Ile
    450                 455                 460

Ile Ile Leu Asp His Leu Tyr Ser Cys Arg Phe Gly Thr Phe Leu Phe
465                 470                 475                 480

Asn Cys Glu Ser Ala Arg Glu Arg Gln Lys Val Thr Glu Arg Thr Val
                485                 490                 495
```

-continued

```
Ser Leu Trp Ser Leu Ile Asn Ser Asn Lys Glu Lys Phe Lys Asn Pro
            500                 505                 510

Phe Tyr Thr Lys Glu Ile Asn Arg Val Leu Tyr Pro Val Ala Ser Met
        515                 520                 525

Arg His Leu Glu Leu Trp Val Asn Tyr Tyr Ile Arg Trp Asn Pro Arg
    530                 535                 540

Ile Lys Gln Gln Gln Pro Asn Pro Val Glu Gln Arg Tyr Met Glu Leu
545                 550                 555                 560

Leu Ala Leu Arg Asp Glu Tyr Ile Lys Arg Leu Glu Glu Leu Gln Leu
                565                 570                 575

Ala Asn Ser Ala Lys Leu Ser Asp Pro Pro Thr Ser Pro Ser Ser Pro
            580                 585                 590

Ser Gln Met Met Pro His Val Gln Thr His Phe
        595                 600


<210> SEQ ID NO 2
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
        115


<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser Gly Gly Gly Gly Ser Gly Gly Gly Gly Ser
1               5                   10                  15


<210> SEQ ID NO 4
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 4

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe His Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys
            100                 105                 110
```

<210> SEQ ID NO 5
<211> LENGTH: 3452
<212> TYPE: DNA
<213> ORGANISM: Homo sapiens

<400> SEQUENCE: 5

```
agagggggcg gagcagggcc cggcagccga gcagcctggc aacggcggtg gcgcccggag     60

cccgagagtt tccaggatgg cttctgcatc aacttctaaa tataattcac actccttgga    120

gaatgagtct attaagagga cgtctcgaga tggagtcaat cgagatctca ctgaggctgt    180

tcctcgactt ccaggagaaa cactaatcac tgacaaagaa gttatttaca tatgtccttt    240

caatggcccc attaagggaa gagtttacat cacaaattat cgtctttatt taagaagttt    300

ggaaacggat tcttctctaa tacttgatgt tcctctgggt gtgatctcga gaattgaaaa    360

aatgggaggc gcgacaagta gaggagaaaa ttcctatggt ctagatatta cttgtaaaga    420

catgagaaac ctgaggttcg ctttgaaaca ggaaggccac agcagaagag atatgtttga    480

gatcctcacg agatacgcgt ttcccctggc tcacagtctg ccattatttg catttttaaa    540

tgaagaaaag tttaacgtgg atggatggac agtttacaat ccagtggaag aatacaggag    600

gcagggcttg cccaatcacc attggagaat aacttttatt aataagtgct atgagctctg    660

tgacacttac cctgctcttt tggtggttcc gtatcgtgcc tcagatgatg acctccggag    720

agttgcaact tttaggtccc gaaatcgaat tccagtgctg tcatggattc atccagaaaa    780

taagacggtc attgtgcgtt gcagtcagcc tcttgtcggt atgagtggga aacgaaataa    840

agatgatgag aaatatctcg atgttatcag ggagactaat aaacaaattt ctaaactcac    900

catttatgat gcaagaccca gcgtaaatgc agtggccaac aaggcaacag gaggaggata    960

tgaaagtgat gatgcatatc ataacgccga acttttcttc ttagacattc ataatattca   1020

tgttatgcgg gaatctttaa aaaaagtgaa ggacattgtt tatcctaatg tagaagaatc   1080

tcattggttg tccagtttgg agtctactca ttggttagaa catatcaagc tcgttttgac   1140

aggagccatt caagtagcag acaaagtttc ttcagggaag agttcagtgc ttgtgcattg   1200

cagtgacgga tgggacagga ctgctcagct gacatccttg gccatgctga tgttggatag   1260

cttctatagg agcattgaag ggttcgaaat actggtacaa aaagaatgga taagttttgg   1320

acataaattt gcatctcgaa taggtcatgg tgataaaaac cacaccgatg ctgaccgttc   1380

tcctattttt ctccagttta ttgattgtgt gtggcaaatg tcaaaacagt tccctacagc   1440
```

-continued

```
ttttgaattc aatgaacaat ttttgattat aattttggat catctgtata gttgccgatt   1500

tggtactttc ttattcaact gtgaatctgc tcgagaaaga cagaaggtta cagaaaggac   1560

tgtttcttta tggtcactga taaacagtaa taaagaaaaa ttcaaaaacc ccttctatac   1620

taaagaaatc aatcgagttt tatatccagt tgccagtatg cgtcacttgg aactctgggt   1680

gaattactac attagatgga accccaggat caagcaacaa cagccgaatc cagtggagca   1740

gcgttacatg gagctcttag ccttacgcga cgaatacata aagcggcttg aggaactgca   1800

gctcgccaac tctgccaagc tttctgatcc cccaacttca ccttccagtc cttcgcaaat   1860

gatgccccat gtgcaaactc acttctgagg ggggaccctg gcaccgcatt agagctcgaa   1920

ataaaggcga tagctgactt tcatttgggg catttgtaaa aagtagatta aaatatttgc   1980

ctccatgtag aacttgaact aacataatct taaactcttg aatatgtgcc ttctagaata   2040

catattacaa gaaaactaca gggtccacac ggcaatcaga agaaaggagc tgagatgagg   2100

ttttggaaaa ccctgacacc tttaaaaagc agtttttgaa agacaaaatt tagatttaat   2160

ttacgtcttg agaaatacta tatatacaat atatattttg tgggcttaat tgaaacaaca   2220

ttattttaaa atcaaagggg atatatgttt gtggaatgga ttttcctgaa gctgcttaac   2280

agttgctttg gattctctaa gatgaatcca aatgtgaaag atgcatgtta ctgccaaaac   2340

caaattgagc tcagcttcct aggcattacc caaaagcaag gtgtttaagt aattgccagc   2400

ttttatacca tcatgagtgg tgacttaagg agaaatagct gtatagatga gtttttcatt   2460

atttggaaat ttaggggtag aaaatgtttt cccctaattt tccagagaag cctattttta   2520

tatttttaaa aaactgacag ggcccagtta aatatgattt gcattttttta aatttgccag   2580

ttttattttc taaattcttt catgagcttg cctaaaattc ggaatggttt tcgggttgtg   2640

gcaaaccccca aagagagcac tgtccaagga tgtcgggagc atcctgctgc ttaggggaat   2700

gttttcgcaa atgttgctct agtcagtcca gctcatctgc caaaatgtag ggctaccgtc   2760

ttggatgcat gagctattgc tagagcatca tccttagaaa tcagtgcccc agatgtacat   2820

gtgttgagcg tattcttgaa agtattgtgt ttatgcattt caatttcaat ggtgttggct   2880

tcccctcccc accccacgcg tgcataaaaa ctggttctac aaatttttac ttgaagtacc   2940

aggccgtttg ctttttcagg ttgttttgtt ttatagtatt aagtgaaatt ttaaatgcac   3000

agttctattt gctatctgaa ctaattcatt tattaagtat atttgtaaaa gctaaggctc   3060

gagttaaaac aatgaagtgt tttacaatga tttgtaaagg actatttata actaatatgg   3120

ttttgttttc aatgaattaa gaaagattaa atatatcttt gtaaattatt ttatgtcata   3180

gtttaattgg tctaccaagt aagacatctc aaatacagta gtataatgta tgaattttgt   3240

aagtataaga aattttatta gacattctct tactttttgt aaatgctgta aatatttcat   3300

aaattaacaa agtgtcactc cataaaaaga aagctaatac taatagccta aaagattttg   3360

tgaaatttca tgaaaacttt ttaatggcaa taatgactaa agacctgctg taataaatgt   3420

attaactgaa acctaaaaaa aaaaaaaaaa aa                                  3452
```

<210> SEQ ID NO 6
<211> LENGTH: 603
<212> TYPE: PRT
<213> ORGANISM: Mus musculus

<400> SEQUENCE: 6

Met Ala Ser Ala Ser Ala Ser Lys Tyr Asn Ser His Ser Leu Glu Asn
1               5                   10                  15

Glu Ser Ile Lys Lys Val Ser Gln Asp Gly Val Ser Gln Asp Val Ser
            20                  25                  30

Glu Thr Val Pro Arg Leu Pro Gly Glu Leu Leu Ile Thr Glu Lys Glu
        35                  40                  45

Val Ile Tyr Ile Cys Pro Phe Asn Gly Pro Ile Lys Gly Arg Val Tyr
    50                  55                  60

Ile Thr Asn Tyr Arg Leu Tyr Leu Arg Ser Leu Glu Thr Asp Ser Ala
65                  70                  75                  80

Leu Ile Leu Asp Val Pro Leu Gly Val Ile Ser Arg Ile Glu Tyr Met
                85                  90                  95

Gly Gly Ala Thr Ser Arg Gly Glu Asn Ser Tyr Gly Leu Asp Ile Thr
            100                 105                 110

Cys Lys Asp Leu Arg Asn Leu Arg Phe Ala Leu Lys Gln Glu Gly His
        115                 120                 125

Ser Arg Arg Asp Met Phe Glu Ile Leu Val Lys His Ala Phe Pro Leu
    130                 135                 140

Ala His Asn Leu Pro Leu Phe Ala Phe Val Asn Glu Glu Lys Phe Asn
145                 150                 155                 160

Val Asp Gly Trp Thr Val Tyr Asn Pro Val Glu Glu Tyr Arg Arg Gln
                165                 170                 175

Gly Leu Pro Asn His His Trp Arg Ile Ser Phe Ile Asn Lys Cys Tyr
            180                 185                 190

Glu Leu Cys Glu Thr Tyr Pro Ala Leu Leu Val Val Pro Tyr Arg Thr
        195                 200                 205

Ser Asp Asp Asp Leu Arg Arg Ile Ala Thr Phe Arg Ser Arg Asn Arg
    210                 215                 220

Leu Pro Val Leu Ser Trp Ile His Pro Glu Asn Lys Met Val Ile Met
225                 230                 235                 240

Arg Cys Ser Gln Pro Leu Val Gly Met Ser Gly Lys Arg Asn Lys Asp
                245                 250                 255

Asp Glu Lys Tyr Leu Asp Val Ile Arg Glu Thr Asn Lys Gln Thr Ser
            260                 265                 270

Lys Leu Met Ile Tyr Asp Ala Arg Pro Ser Val Asn Ala Val Ala Asn
        275                 280                 285

Lys Ala Thr Gly Gly Gly Tyr Glu Ser Asp Asp Ala Tyr Gln Asn Ser
    290                 295                 300

Glu Leu Ser Phe Leu Asp Ile His Asn Ile His Val Met Arg Glu Ser
305                 310                 315                 320

Leu Lys Lys Val Lys Asp Ile Val Tyr Pro Asn Ile Glu Glu Ser His
                325                 330                 335

Trp Leu Ser Ser Leu Glu Ser Thr His Trp Leu Glu His Ile Lys Leu
            340                 345                 350

Val Leu Thr Gly Ala Ile Gln Val Ala Asp Gln Val Ser Ser Gly Lys
        355                 360                 365

Ser Ser Val Leu Val His Cys Ser Asp Gly Trp Asp Arg Thr Ala Gln
    370                 375                 380

Leu Thr Ser Leu Ala Met Leu Met Leu Asp Ser Phe Tyr Arg Thr Ile
385                 390                 395                 400

Glu Gly Phe Glu Ile Leu Val Gln Lys Glu Trp Ile Ser Phe Gly His
                405                 410                 415

-continued

Lys Phe Ala Ser Arg Ile Gly His Gly Asp Lys Asn His Ala Asp Ala
420 425 430

Asp Arg Ser Pro Ile Phe Leu Gln Phe Ile Asp Cys Val Trp Gln Met
435 440 445

Ser Lys Gln Phe Pro Thr Ala Phe Glu Phe Asn Glu Gly Phe Leu Ile
450 455 460

Thr Val Leu Asp His Leu Tyr Ser Cys Arg Phe Gly Thr Phe Leu Phe
465 470 475 480

Asn Cys Asp Ser Ala Arg Glu Arg Gln Lys Leu Thr Glu Arg Thr Val
485 490 495

Ser Leu Trp Ser Leu Ile Asn Ser Asn Lys Asp Lys Phe Lys Asn Pro
500 505 510

Phe Tyr Thr Lys Glu Ile Asn Arg Val Leu Tyr Pro Val Ala Ser Met
515 520 525

Arg His Leu Glu Leu Trp Val Asn Tyr Tyr Ile Arg Trp Asn Pro Arg
530 535 540

Val Lys Gln Gln Gln Pro Asn Pro Val Glu Gln Arg Tyr Met Glu Leu
545 550 555 560

Leu Ala Leu Arg Asp Asp Tyr Ile Lys Arg Leu Glu Glu Leu Gln Leu
565 570 575

Ala Asn Ser Ala Lys Leu Ala Asp Ala Pro Ala Ser Thr Ser Ser Ser
580 585 590

Ser Gln Met Val Pro His Val Gln Thr His Phe
595 600

<210> SEQ ID NO 7
<211> LENGTH: 3338
<212> TYPE: DNA
<213> ORGANISM: Mus musculus

<400> SEQUENCE: 7
ggtgagttcg ctttcttggc tgacctggct cggagccggg cattgcgggg atccaggatt 60
ggaaaggttc caggatggct tctgcatcag catctaagta taattcacac tccttggaga 120
atgaatccat taagaaagtg tctcaagatg gagtcagtca ggatgtgagt gagactgtcc 180
ctcggctccc aggggagtta ctaattactg aaaaagaagt tatttacata tgtcctttca 240
atggccccat taagggaaga gtttacatca caaattatcg tctttattta agaagtttgg 300
aaacggattc tgctctaata cttgatgttc ctctgggtgt gatatcaaga attgaatata 360
tgggaggcgc gactagtaga ggagaaaatt cctatggtct agatattact tgtaaagatt 420
tgagaaacct gaggtttgca ttgaagcaag aaggccacag cagaagagat atgtttgaga 480
tccttgtaaa acatgccttt cctctggcac acaatctgcc attatttgca tttgtaaatg 540
aagagaagtt taacgtggat gggtggactg tttataatcc agttgaagaa tatagaaggc 600
agggcctgcc caatcaccat tggaggataa gttttattaa caagtgctat gagctctgtg 660
agacataccc tgctcttttg gtggttccct atcggacctc agatgatgat cttaggagga 720
tcgcaacgtt tagatcccga aatcggcttc ctgtactgtc gtggattcac ccagaaaaca 780
aaatggtcat tatgcgctgc agtcagcctc ttgtcggtat gagtggtaaa agaaataaag 840
atgacgagaa atacctggat gtgatcaggg aaactaacaa acaaacttct aagctcatga 900
tttatgatgc acgacccagt gtaaatgcag tcgccaacaa ggcaacagga ggaggatatg 960
aaagtgatga cgcatatcaa aactcagaac tttccttctt agacattcat aatattcatg 1020
ttatgcgaga atctttaaaa aaagtgaaag atattgttta tcccaacata gaagaatctc 1080

-continued

```
attggttgtc cagtttggag tctactcatt ggttagaaca tatcaagctt gttctgaccg   1140
gtgccattca agtggcagac caagtgtctt caggaaagag ctcggtactt gtgcactgca   1200
gtgacggatg ggacaggacc gctcagctga catccttggc catgctgatg ttggacagct   1260
tctacagaac tattgaaggc tttgagatat tggtacagaa agagtggata agttttggcc   1320
ataaatttgc atctagaata ggtcatggtg ataaaaacca tgctgatgct gatcgatctc   1380
ctatttttct tcagtttatt gactgtgtgt ggcagatgtc gaaacagttc cccacagctt   1440
ttgagttcaa tgaaggcttt ttgattaccg ttttggatca tctgtatagc tgtcgatttg   1500
gtactttctt attcaactgt gactcggctc gagaaagaca gaaacttaca gaaagaacag   1560
tttctctatg gtcgctaatt aacagcaata aagacaaatt caaaaacccc ttctatacaa   1620
aagaaatcaa tcgggttttg tatccagttg ccagcatgcg tcacttggaa ctgtgggtga   1680
attattacat ccgatggaat cccagggtca agcagcaaca gcccaaccca gtggagcagc   1740
gttacatgga gcttttggcc ttgcgtgacg attatataaa gaggctcgag gaattgcagc   1800
tggccaactc cgccaagctt gctgatgccc ccgcttcgac ttccagttcg tcacagatgg   1860
tgccccatgt gcagacgcac ttctgagggg actcacttct ggcactgcac ttgaactcta   1920
gataagtgaa atagctgact ctcattctgg gcatgtggac aaagtagatt taaagtgtct   1980
gcctccattt agaagttcaa ctaacatctt agacttttga gtatgtgcct tctgtaatac   2040
atatcacaag aaatcgatgg tgtccgtgtg gcaatcataa ggaaggagtc aagagggggt   2100
tctggaaaat cctcatactt ttttttacaa agcacttttg caaagataaa acttaaattt   2160
aatttacctc tatataaatt ctacatatac agtatgtatt ttgtgggctt aattgaaata   2220
ttattttaaa tccagggggg agatttgttt gcaaaatgta ttttcctcca gctgcttata   2280
acagttgctt tggattatct aaaattaatc caaatgtgaa agatgggtat tactgccaaa   2340
gccaaattgc actctgcttc ttcagcaaat tccaagagca aggcgtttaa ataattgcca   2400
atttttattt taccataagt ggtaaggtaa aaagaaagat gaacatttca tcattttgaa   2460
tttttgaaaa taaaaggttc tcccatcatt tttcaagaga agcacatttt tatattaaga   2520
aaaagtgata aggtttgatt ttttttccc tcaacattct cagctttgct ttctaaatta   2580
tcccatgatt tttgtctaac actgagtcat actcaggttg aaggaaaccc ataaatagca   2640
ctgtgcgagg agctggctgg cttctgctgc ttagaggaat atgttcgcaa acatgcctct   2700
agtcaattcg ccttatctgc tgaagtgtag gggcaccgcc ttgaatggat gagctatggc   2760
tagagcatct ttctttacag taatgcccca ggtgtattct gtttatgtct ctctgtttaa   2820
atggtgtgcg tgcataaaaa cttgctctgc acattattac ttgaagtact gggcaatttg   2880
ctttttcagg tttttttca ttttgttttg tagtatgaaa tggaatttta aatgcacagt   2940
tctatttgat atccgaacta attcatttag taaatatatt tgtaaaagct aaagttaaat   3000
caattaatgt tttacagtga tttgtaaagg attatttata gctaatatgg ttttgttttc   3060
agtgaattaa gagagattac atttatcttt gtaaattatt ttatgtcata gcttaatggc   3120
ctaccaaatg agacatctca aatataatag tataatgtat ggattttgta agtataaaaa   3180
ttattagata ttcgtttgct ttttgtaaac actgtaaata tttcataaat taaaatgtgt   3240
cactccataa gaagaaaaaa ctaatactaa tagttgacag gaattggtga aatttcatga   3300
aaatatttc attgcaataa atattaaaag acctgctg                          3338
```

<210> SEQ ID NO 8
<211> LENGTH: 553
<212> TYPE: PRT
<213> ORGANISM: Rattus norvegicus

<400> SEQUENCE: 8

```
Met Ala Ser Ser Ser Ala Ser Asp Cys Asp Ala His Pro Val Glu Arg
1               5                   10                  15

Glu Ser Met Arg Lys Val Ser Gln Asp Gly Val Arg Gln Asp Met Ser
            20                  25                  30

Lys Ser Gly Pro Arg Leu Pro Gly Glu Ser Ala Ile Thr Asp Lys Glu
        35                  40                  45

Val Ile Tyr Ile Cys Pro Phe Ser Gly Pro Val Lys Gly Arg Leu Tyr
    50                  55                  60

Ile Thr Asn Tyr Arg Leu Tyr Leu Arg Ser Leu Glu Thr Asp Leu Ala
65                  70                  75                  80

Pro Ile Leu Asp Val Pro Leu Gly Val Ile Ser Arg Ile Glu Lys Met
                85                  90                  95

Gly Gly Val Thr Ser Arg Gly Glu Asn Ser Tyr Gly Leu Asp Ile Thr
            100                 105                 110

Cys Lys Asp Leu Arg Asn Leu Arg Phe Ala Leu Lys Gln Glu Gly His
        115                 120                 125

Ser Arg Arg Asp Ile Phe Asp Val Leu Thr Arg His Ala Phe Pro Leu
    130                 135                 140

Ala Tyr Asn Leu Pro Leu Phe Ala Phe Val Asn Glu Glu Lys Phe Lys
145                 150                 155                 160

Val Asp Gly Trp Ala Ile Tyr Asn Pro Val Glu Glu Tyr Arg Arg Gln
                165                 170                 175

Gly Leu Pro Asp Arg His Trp Arg Ile Ser Phe Val Asn Gln Arg Tyr
            180                 185                 190

Glu Leu Cys Asp Thr Tyr Pro Ala Leu Leu Val Val Pro Tyr Arg Ala
        195                 200                 205

Ser Asp Asp Asp Leu Arg Arg Val Ala Thr Phe Arg Ser Arg Asn Arg
    210                 215                 220

Ile Pro Val Leu Ser Trp Ile His Pro Glu Asn Arg Ala Ala Ile Met
225                 230                 235                 240

Arg Cys Ser Gln Pro Leu Val Gly Val Gly Gly Lys Arg Ser Arg Asp
                245                 250                 255

Asp Glu Arg Tyr Leu Asp Ile Ile Arg Glu Thr Asn Lys Gln Thr Ser
            260                 265                 270

Lys Leu Thr Ile Tyr Asp Ala Arg Pro Gly Val Asn Ala Val Ala Asn
        275                 280                 285

Lys Ala Thr Gly Gly Gly Tyr Glu Gly Glu Asp Ala Tyr Pro His Ala
    290                 295                 300

Glu Leu Ser Phe Leu Asp Ile His Asn Ile His Val Met Arg Glu Ser
305                 310                 315                 320

Leu Arg Arg Val Arg Asp Ile Val Tyr Pro His Val Glu Glu Ala His
                325                 330                 335

Trp Leu Ser Ser Leu Glu Ser Thr His Trp Leu Glu His Ile Lys Leu
            340                 345                 350

Leu Leu Thr Gly Ala Ile Arg Val Ala Asp Lys Val Ala Ser Gly Leu
        355                 360                 365

Ser Ser Val Leu Val His Cys Ser Asp Gly Trp Asp Arg Thr Ala Gln
    370                 375                 380
```

-continued

```
Leu Thr Thr Leu Ala Met Leu Met Leu Asp Gly Phe Tyr Arg Ser Ile
385                 390                 395                 400

Glu Gly Phe Glu Ile Leu Val Gln Lys Glu Trp Ile Ser Phe Gly His
                405                 410                 415

Lys Phe Ser Ser Arg Ile Gly His Gly Asp Lys Asn His Ala Asp Ala
            420                 425                 430

Asp Arg Ser Pro Ile Phe Leu Gln Phe Ile Asp Cys Val Trp Gln Met
        435                 440                 445

Thr Lys Gln Phe Pro Thr Ala Phe Glu Phe Asn Glu Cys Phe Leu Val
    450                 455                 460

Ala Ile Leu Asp His Leu Tyr Ser Cys Arg Phe Gly Thr Phe Leu Leu
465                 470                 475                 480

Asn Cys Glu Ala Ala Arg Glu Arg Gln Arg Leu Ala Glu Arg Thr Val
                485                 490                 495

Ser Val Trp Ser Leu Ile Asn Ser Asn Lys Asp Glu Phe Thr Asn Pro
            500                 505                 510

Phe Tyr Ala Arg Glu Ser Asn Arg Val Ile Tyr Pro Val Thr Ser Val
        515                 520                 525

Arg His Leu Glu Leu Trp Val Asn Tyr Tyr Ile Arg Trp Asn Pro Arg
    530                 535                 540

Ile Arg Gln Gln Gln Pro His Pro Met
545                 550


<210> SEQ ID NO 9
<211> LENGTH: 2536
<212> TYPE: DNA
<213> ORGANISM: Rattus norvegicus

<400> SEQUENCE: 9

gcgagcgcgt tggcaccagc ggcccccgga gtctcaggtt ccaggatggc gtcctcgtca      60

gcctctgact gtgatgcaca ccccgtggag cgtgagtcca tgaggaaggt gtctcaagat     120

ggagtccgtc aggatatgag caagagtggg cctcgcctcc caggggaatc agccatcact     180

gacaaggaag tcatctacat ttgtcccttc agcggccccg taaagggacg actttacatc     240

accaattacc gtctctacct gagaagtctg gagacggact tggctccgat tcttgacgtc     300

cccctaggcg tgatatcgag aatagagaaa atgggaggcg tgacgagtcg aggagagaat     360

tcctacggcc ttgatatcac ctgcaaagac ctgaggaacc tgaggttcgc tctgaagcag     420

gaaggacaca gcaggaggga catctttgac gtcctcacca gacacgcctt ccccctggct     480

tacaacctgc cgttgtttgc attcgtgaac gaggagaagt ttaaagtgga tggatgggcg     540

atttacaacc cggttgaaga gtacagaagg cagggcctcc ccgatcgcca ttggcggata     600

agtttcgtca atcagcgcta cgagctctgt gacacctacc ctgccctcct ggtcgtcccc     660

taccgtgcgt ccgatgatga cctcagaaga gttgcaacct ttaggtccag aaaccggatt     720

cccgtgctgt cgtggatcca cccagagaac agggcggcga tcatgcggtg cagtcagcct     780

ctggttggtg tgggcgggaa gagaagcaga gatgatgaga gatacctgga catcatccgg     840

gaaaccaata agcagacctc gaagctcaca atttacgatg cgcggcccgg cgtcaatgcg     900

gtggccaaca aggcaacggg aggcggctat gagggcgagg acgcgtaccc tcacgcggag     960

ctctccttcc tggacatcca caacatccac gtgatgcggg aatccttacg gagggtgagg    1020

gacatcgtgt acccccacgt ggaggaagct cattggctgt ccagcttgga gtccacccat    1080

tggttagagc acatcaagct tctcctcact ggtgccatcc gggtcgcaga caaggtggca    1140
```

```
tcggggctga gttcagtcct cgtgcactgc agtgacggct gggaccggac ggctcaactg   1200

accacgctgg ccatgctgat gctcgatggc ttctaccgca gcatcgaggg ctttgagatc   1260

ctggtgcaga aggagtggat cagcttcgga cacaagtttt catctagaat tggccacggt   1320

gacaagaacc acgcggatgc cgaccgctcc ccgattttcc tgcagttcat cgactgcgtg   1380

tggcagatga cgaagcagtt ccccacagct ttcgagttca acgagtgctt cctggttgcc   1440

atcttggatc acctgtacag ctgccggttc gggacttttct tactaaactg tgaggcggca   1500

cgggagagac agagactcgc agaaaggacg gtgtctgtgt ggtccctgat caacagcaac   1560

aaagacgaat tcacaaaccc gttctacgca agggagagca accgcgtgat ctacccggtc   1620

accagcgtgc gccacctgga actgtgggtg aattactaca tccggtggaa ccccaggatc   1680

cggcagcagc agccccaccc catgtagcag cgatataatg agctcctggc cctgcgtgac   1740

gattacatca agaagctgga ggagctgcag ctggccacgc ccaccaagct cactgactcc   1800

tccaccccgc cttccggttc cgcacagata gctccccgca tgcaaactca cttctgaggg   1860

ggttccgggc cccaaaccct gaataagtga cgtcaccaac ttccgttctg tgcgcttgtg   1920

caaaggggat ataaagtctc cgcctctgtg tagaagtcga actaacaccc tagaaccttg   1980

tgtgacacgt gtgagtgtgc gccttttgtg acgtgtgagt gtgcgatttg tgtgacatgt   2040

gtgaatgtgt accctgtgtg atacgtgcaa gtgtgcgcct tgtgtaaagt tcgtgagtgt   2100

gcacctcctg taacatgttt tgcaaggaat ctactgcgct tgtgtgccag tcgtgagtac   2160

agagtagggg gggtcccgga aaaatcctca cacttttttta caaagcgctt gtgcaaagat   2220

taaaattaaa ttatatcaat aattatataa attattataa ttatattgca aagattaaaa   2280

agttaaattt agtttacctc tatataaatc cagacataca taatatgtac tctgtgcgct   2340

taattgaaac gttattttaa atccagaggg gagatttttt ttgtaaaatg gatttttcct   2400

ccagccactt attttgcaaa gataaaaaag ttaaaataaa agttaaattt aattataaaa   2460

aaaaaaaaaa aaaaaaaaaa aaaaaaaaaa aaaaaaaaaa aaaaaaaaaa aaaaaaaaaa   2520

aaaaaaaaaa aaaaaa                                                   2536


<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ser Thr Ser Gly Ser Gly Lys Ser Ser Glu Gly Lys Gly
1               5                   10


<210> SEQ ID NO 11
<211> LENGTH: 864
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30
```

-continued

```
Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe His Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys Gly
            100                 105                 110

Gly Gly Gly Ser Gly Gly Gly Gly Ser Gly Gly Gly Ser Glu Val Gln
        115                 120                 125

Leu Val Glu Ser Gly Gly Gly Leu Val Lys Pro Gly Gly Ser Arg Lys
    130                 135                 140

Leu Ser Cys Ala Ala Ser Gly Phe Thr Phe Ser Asn Tyr Gly Met His
145                 150                 155                 160

Trp Val Arg Gln Ala Pro Glu Lys Gly Leu Glu Trp Val Ala Tyr Ile
                165                 170                 175

Ser Ser Gly Ser Ser Thr Ile Tyr Tyr Ala Asp Thr Val Lys Gly Arg
            180                 185                 190

Phe Thr Ile Ser Arg Asp Asn Ala Lys Asn Thr Leu Phe Leu Gln Met
        195                 200                 205

Thr Ser Leu Arg Ser Glu Asp Thr Ala Met Tyr Tyr Cys Ala Arg Arg
    210                 215                 220

Gly Leu Leu Leu Asp Tyr Trp Gly Gln Gly Thr Thr Leu Thr Val Ser
225                 230                 235                 240

Ser Glu Gln Lys Leu Ser Glu Glu Leu Gly Ser Thr Ser Gly Ser Gly
                245                 250                 255

Lys Ser Ser Glu Gly Lys Gly Met Ala Ser Ala Ser Thr Ser Lys Tyr
            260                 265                 270

Asn Ser His Ser Leu Glu Asn Glu Ser Ile Lys Arg Thr Ser Arg Asp
        275                 280                 285

Gly Val Asn Arg Asp Leu Thr Glu Ala Val Pro Arg Leu Pro Gly Glu
    290                 295                 300

Thr Leu Ile Thr Asp Lys Glu Val Ile Tyr Ile Cys Pro Phe Asn Gly
305                 310                 315                 320

Pro Ile Lys Gly Arg Val Tyr Ile Thr Asn Tyr Arg Leu Tyr Leu Arg
                325                 330                 335

Ser Leu Glu Thr Asp Ser Ser Leu Ile Leu Asp Val Pro Leu Gly Val
            340                 345                 350

Ile Ser Arg Ile Glu Lys Met Gly Gly Ala Thr Ser Arg Gly Glu Asn
        355                 360                 365

Ser Tyr Gly Leu Asp Ile Thr Lys Asp Met Arg Asn Leu Arg Phe Ala
    370                 375                 380

Leu Lys Gln Glu Gly His Arg Arg Asp Met Phe Glu Ile Leu Thr Arg
385                 390                 395                 400

Tyr Ala Phe Pro Leu Ala His Ser Leu Pro Leu Phe Ala Phe Leu Asn
                405                 410                 415

Glu Glu Lys Phe Asn Val Asp Gly Trp Thr Val Tyr Asn Pro Val Glu
            420                 425                 430

Glu Tyr Arg Arg Gln Gly Leu Pro Asn His His Trp Arg Ile Thr Phe
        435                 440                 445
```

-continued

```
Ile Asn Lys Cys Tyr Glu Leu Cys Asp Thr Tyr Pro Ala Leu Leu Val
    450                 455                 460

Val Pro Tyr Arg Ala Ser Asp Asp Asp Leu Arg Arg Val Ala Thr Phe
465                 470                 475                 480

Arg Ser Arg Asn Arg Ile Pro Val Leu Ser Trp Ile His Pro Glu Asn
                485                 490                 495

Lys Thr Val Ile Val Cys Ser Gln Pro Leu Val Gly Met Ser Gly Lys
            500                 505                 510

Arg Asn Lys Asp Asp Lys Tyr Leu Asp Val Ile Arg Glu Thr Asn Lys
        515                 520                 525

Gln Ile Ser Lys Leu Thr Ile Tyr Asp Ala Arg Pro Ser Val Asn Ala
    530                 535                 540

Val Ala Asn Lys Ala Thr Gly Gly Gly Tyr Glu Ser Asp Asp Ala Tyr
545                 550                 555                 560

His Asn Ala Glu Leu Phe Phe Leu Asp Ile His Asn Ile His Val Met
                565                 570                 575

Arg Glu Ser Leu Lys Lys Val Lys Asp Ile Val Tyr Pro Asn Val Glu
            580                 585                 590

Glu Ser His Trp Leu Ser Ser Leu Glu Ser Thr His Trp Leu Glu His
        595                 600                 605

Ile Lys Leu Val Leu Thr Gly Ala Ile Gln Val Ala Asp Lys Val Ser
    610                 615                 620

Ser Gly Lys Ser Val Leu Val His Cys Ser Asp Gly Trp Asp Arg Thr
625                 630                 635                 640

Ala Gln Leu Thr Leu Ala Met Leu Met Leu Asp Ser Phe Tyr Arg Ser
                645                 650                 655

Ile Glu Gly Phe Glu Ile Leu Val Gln Lys Lys Trp Ile Ser Phe Gly
            660                 665                 670

His Lys Phe Ala Ser Arg Ile Gly His Gly Asp Lys Asn His Thr Asp
        675                 680                 685

Ala Asp Arg Ser Pro Ile Phe Leu Gln Phe Ile Asp Cys Val Trp Gln
    690                 695                 700

Met Ser Lys Gln Phe Pro Thr Ala Phe Glu Phe Asn Glu Gln Phe Leu
705                 710                 715                 720

Ile Ile Ile Leu Asp His Leu Tyr Ser Cys Arg Phe Gly Thr Phe Leu
                725                 730                 735

Phe Asn Cys Glu Ser Ala Arg Glu Arg Gln Lys Val Thr Glu Arg Thr
            740                 745                 750

Val Leu Trp Ser Leu Ile Asn Ser Asn Lys Glu Lys Phe Lys Asn Pro
        755                 760                 765

Phe Tyr Thr Glu Ile Asn Arg Val Leu Tyr Pro Val Ala Ser Met Arg
    770                 775                 780

His Leu Glu Leu Trp Val Asn Tyr Tyr Ile Arg Trp Asn Pro Arg Ile
785                 790                 795                 800

Lys Gln Gln Gln Pro Asn Pro Val Glu Gln Arg Tyr Met Glu Leu Leu
                805                 810                 815

Ala Leu Arg Asp Glu Tyr Ile Lys Arg Leu Glu Glu Leu Gln Leu Ala
            820                 825                 830

Asn Ser Ala Lys Leu Ser Asp Pro Pro Thr Ser Pro Ser Ser Pro Ser
        835                 840                 845

Gln Met Met Pro His Val Gln Thr His Phe His His His His His His
    850                 855                 860
```

-continued

```
<210> SEQ ID NO 12
<211> LENGTH: 7
<212> TYPE: PRT
<213> ORGANISM: Unknown
<220> FEATURE:
<223> OTHER INFORMATION: Description of Unknown: Homing peptide

<400> SEQUENCE: 12

Ala Ser Ser Leu Asn Ile Ala
1               5


<210> SEQ ID NO 13
<211> LENGTH: 7
<212> TYPE: PRT
<213> ORGANISM: Rattus sp.

<400> SEQUENCE: 13

Arg Arg Arg Arg Arg Arg Arg
1               5


<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5
```

METHODS AND COMPOSITIONS FOR TREATMENT OF MYOTUBULAR MYOPATHY USING CHIMERIC POLYPEPTIDES COMPRISING MYOTUBULARIN 1(MTM1) POLYPEPTIDES

RELATED APPLICATIONS

This application is a continuation of U.S. application Ser. No. 13/378,283, filed May 3, 2012, which is a national stage filing under 35 U.S.C. 371 of International Application No. PCT/US2010/038703, filed Jun. 15, 2010, which claims the benefit of the filing date under 35 U.S.C. 119(e) to U.S. provisional application No. 61/268,732, filed Jun. 15, 2009, the disclosure of which is hereby incorporated by reference in its entirety. International Application No. PCT/US2010/038703 was published under PCT Article 21(2) in English.

SEQUENCE LISTING

The instant application contains a Sequence Listing which has been submitted via EFS-Web and is hereby incorporated by reference in its entirety. Said ASCII copy, created on Sep. 12, 2014, is named 1061990003302_Seq.txt, and is 38,819 bytes in size.

BACKGROUND OF THE INVENTION

Myotubuler myopathy (MTM) is a rare and severe X-linked muscle disorder that occurs with an estimated incidence of 1 male in every 50,000 births. Myotubular myopathy is a member of a category of diseases referred to as centronuclear myopathies. A cardinal feature of centronuclear myopathies is that the nucleus is positioned in the center of many of the affected individual's muscle cells, rather than in the normal location at the ends of these cells. Although centronuclear myopathies share this characteristic feature, the various diseases have different causes, afflict different patient populations, and have unique disease progression and prognosis.

Myotubular myopathy is caused by a deficiency of the myotubularin 1 (MTM1) protein, a phosphoinositide phosphatase (Bello A B et al., Human Molecular Genetics, 2008, Vol, 17, No. 14), At birth MTM patients present with severe hypotonia and respiratory distress and those that survive the neonatal period are often totally or partially dependent upon ventilator support (Taylor G S et al., Proc Natl Acad Sci USA. 2000 August 1; 97(16):8910-5; Bello A B et al., *Proc Natl Acad Sci USA*. 2002 November 12; 99(23):15060-5; Pierson C R et al., Neuromuscul Disord. 2007 July; 17(7): 562-568; Herman G E et al., THE JOURNAL OF PEDIATRICS VOLUME 134, NUMBER 2). Patients with MTM exhibit delayed motor milestones and are susceptible to complications such as scoliosis, malocclusion, pyloric stenosis, spherocytosis, and gall and kidney stones, yet linear growth and intelligence are normal and the disease follows a non-progressive course (Herman G E et al., THE JOURNAL OF PEDIATRICS VOLUME 134, NUMBER 2). The average hospital stay for neonatal MTM patients is ~90 days. However, patients that survive will require long-term ventilatory assistance and in-home care. The cost of basic supportive care, as well as the costs associated with handling the medical complications that often arise in MTM patients, impose a substantial personal and economic burden on patients and families.

SUMMARY OF THE INVENTION

Currently, there are no therapies for MTM. Treatment is limited to ventilatory assistance and other forms of supportive care to attempt to manage the disabilities associated with the disease. The present disclosure provides methods and compositions for treating MTM.

The present disclosure provides chimeric polypeptides comprising a myotubularin (MTM1) polypeptide or a bioactive fragment thereof and an internalizing moiety, as well as compositions comprising the chimeric polypeptides in combination with a pharmaceutical carrier. Also disclosed are constructs useful for producing such chimeric polypeptides. Further, the present disclosure teaches methods of making the chimeric polypeptides and constructs that encode them. Additionally, disclosed herein are methods of using the chimeric polypeptides, for example, to manipulate phosphatase activity in a cell and as part of a treatment of diseases or conditions associated with MTM1 mutation or deficiency.

In one aspect, the present disclosure provides a chimeric polypeptide comprising (i) a myotubularin (MTM1) polypeptide, or a bioactive fragment thereof and (ii) an internalizing moiety. In certain embodiments, the chimeric polypeptide has phosphoinositide phosphatase activity. That is, the chimeric polypeptide has the ability to cleave or hydrolyze a phosphorylated phosphoinositide molecule. In certain embodiments, a substrate for the chimeric polypeptide is PI3 or PIP3. In certain embodiments the internalizing moiety promotes transport of said chimeric polypeptide into muscle cells. In other words, the internalizing moiety helps the chimeric polypeptide effectively and efficiently transit cellular membranes. In some embodiments, the internalizing moiety transits cellular membranes via an ENT2 transporter. In other words, the internalizing moiety promotes transport of the chimeric polypeptide across cellular membranes via an ENT2 transporter.

In certain embodiments, the MTM1 polypeptide disclosed herein comprises an amino acid sequence at least 90% identical to SEQ ID NO: 1, or a bioactive fragment thereof. In some embodiments, the MTM1 polypeptide comprises an amino acid sequence at least 80%, 85%, 90%, 95%, 97%, 98%, 99% or 100% identical to an MTM1 polypeptide (such as the MTM1 polypeptides represented in one or more of SEQ ID NOs: 1, 6, 8, or a bioactive fragment of any of the foregoing). In certain embodiments, the MTM1 polypeptide comprises an amino acid sequence at least 80%, 85%, 90%, 95%, 97%, 98%, 99% or 100% identical to an MTM1 polypeptide represented in SEQ ID NOs: 1. In certain embodiments, any of the foregoing or following MTM1 polypeptides disclosed herein and for use in a chimeric polypeptide further comprise one or more polypeptide portions that enhance one or more of in vivo stability, in vivo half life, uptake/administration, and/or purification. In certain embodiments, any of the foregoing or following MTM1 polypeptides and/or chimeric polypeptides may further include one or more epitope tags. Such epitope tags may be joined to the MTM1 polypeptide and/or the internalizing moiety. When more than one epitope tag is present (e.g., 2, 3, 4) the tags may be the same or different.

In some embodiments, the internalizing moiety of any of the foregoing chimeric polypeptides comprises an antibody or an antigen-binding fragment thereof. In certain embodiments, the antibody is a monoclonal antibody or an antigen-binding fragment thereof. The antibody or antigen-binding fragment thereof may be, e.g., monoclonal antibody 3E10, or a variant thereof that retains the cell penetrating activity of 3E10, or an antigen-binding fragment of 3E10 or said 3E10 variant. In certain embodiments, the antibody or antigen-binding fragment thereof may be an antibody or antigen-binding fragment that binds to the same epitope as 3E10, or an antibody or antigen-binding fragment that has substantially the same cell penetrating activity as 3E10, or an antigen-binding fragment thereof. In other embodiments, the internalizing moiety of any of the foregoing chimeric polypeptides comprises a homing peptide as described herein. In certain embodiments, the internalizing moiety comprises an antibody or antigen-binding fragment comprising a light chain variable domain (VL) comprising an amino acid sequence at least 90%, 92%, 95%, 96%, 97%, 98%, 99%, or 100% identical to SEQ ID NO: 4. In certain embodiments, the internalizing moiety comprises an antibody or antigen-binding fragment comprising a heavy chain variable domain (VH) comprising an amino acid sequence at least 90%, 92%, 95%, 96%, 97%, 98%, 99%, or 100% identical to SEQ ID NO: 2. In certain embodiments, the internalizing moiety comprises an antibody or antigen-binding fragment comprising: a light chain variable domain (VL) comprising an amino acid sequence at least 90%, 92%, 95%, 96%, 97%, 98%, 99%, or 100% identical to SEQ ID NO: 4 and a heavy chain variable domain (VH) comprising an amino acid sequence at least 90%, 92%, 95%, 96%, 97%, 98%, 99%, or 100% identical to SEQ ID NO: 2. The invention specifically contemplates internalizing moieties based on any combination of the foregoing VH and VL chains, for example, an internalizing moiety comprising a VH comprising an amino acid sequence at least 98% identical to SEQ ID NO: 2 and a VL at least 96% identical to SEQ ID NO: 4. In certain embodiments, the internalizing moiety comprising a VH comprising the amino acid sequence set forth in SEQ ID NO: 2 and a VL comprising the amino acid sequence set forth in SEQ ID NO: 4. As detailed herein, the VH and VL domains may be included as part of a full length antibody or as part of a fragment, such as an scFv. Moreover, the VH and VL domains may be joined by a linker, or may be joined directly. In either case, the VH and VL domains may be joined in either orientation (e.g., with the VL domain N-terminal to the VH domain or with the VH domain N-terminal to the VL domain).

In certain embodiments, any of the foregoing chimeric polypeptides may be produced by chemically conjugating the MTM1 polypeptide, or bioactive fragment thereof, to the internalizing moiety. In certain embodiments, the chimeric polypeptide may be produced recombinantly to recombinantly conjugate the MTM1 polypeptide, or bioactive fragment thereof, to the internalizing moiety. For example, the chimeric polypeptide may be produced using a recombinant vector encoding both the MTM1 polypeptide and the internalizing moiety. In some embodiments, the chimeric polypeptide is produced in a prokaryotic or eukaryotic cell. For example, the eukaryotic cell may be selected from a yeast cell, an avian cell, an insect cell, or a mammalian cell. Note that for embodiments in which the MTM1 polypeptide is chemically conjugated to the internalizing moiety, the invention contemplates that the MTM1 polypeptide and/or internalizing moiety may be produced recombinantly.

In some embodiments, the MTM1 polypeptide or bioactive fragment thereof may be conjugated or joined (whether chemically or recombinantly) to the internalizing moiety by a linker. In other embodiments, the MTM1 polypeptide or bioactive fragment thereof may be conjugated or joined directly to the internalizing moiety. For example, a recombinantly conjugated chimeric polypeptide can be produced as an in-frame fusion of the MTM1 portion and the internalizing moiety portion. In certain embodiments, the linker may be a cleavable linker. In any of the foregoing embodiments, the internalizing moiety may be conjugated (directly or via a linker) to the N-terminal or C-terminal amino acid of the MTM1 polypeptide. In other embodiments, the internalizing moiety may be conjugated (directly or indirectly) to an internal amino acid of the MTM1 polypeptide. Note that the two portions of the construct are conjugated/joined to each other. Unless otherwise specified, describing the chimeric polypeptide as a conjugation of the MTM1 portion to the internalizing moiety is used equivalently as a conjugation of the internalizing moiety to the MTM1 portion. In certain embodiments, a linker joins together one or more portions of the internalizing moiety, such as a VH and VL domain of an antibody. The invention contemplates the use of 0 linkers, 1 linker, 2 linkers, and more than two linkers. When more than 1 linker is used, the linkers may be the same or different.

In certain embodiments, any of the foregoing chimeric polypeptides may be formulated as compositions formulated in a pharmaceutically acceptable carrier. In certain embodiments, the compositions are formulated for intravenous administration.

In a related aspect, the disclose provides chimeric polypeptides comprising the amino acid sequence set forth in SEQ ID NO: 11 or the amino acid sequence set forth in SEQ ID NO: 11, but in the absence of one or both epitope tags. Such chimeric polypeptides, as well as any of the chimeric polypeptides described herein, may be used in any of the methods described herein.

With respect to chimeric polypeptides, the disclosure contemplates all combinations of any of the foregoing aspects and embodiments, as well as combinations with any of the embodiments set forth in the detailed description and examples. Further, any of the chimeric polypeptides of the disclosure can be used in any of the methods described herein.

In another aspect, the present disclosure provides a nucleic acid construct, comprising a nucleotide sequence that encodes an MTM1 polypeptide or a bioactive fragment thereof, operably linked to a nucleotide sequence that encodes an internalizing moiety. In certain embodiments, the nucleic acid construct encodes a chimeric polypeptide having phosphoinositide phosphatase activity. In certain embodiments, the internalizing moiety targets muscle cells to promote transport into muscle cells. In other embodiments, the internalizing moiety transits cellular membranes via an ENT2 transporter.

In some embodiments, the nucleotide sequence that encodes an MTM1 polypeptide comprises a nucleotide sequence at least 90% identical to SEQ ID NO: 5. In certain embodiments, the nucleotide sequence that encodes an MTM1 polypeptide comprises a nucleotide sequence at least 80%, 85%, 90%, 95%, 97%, 98%, 99% or 100% identical to any one or more of SEQ ID NOs: 5, 7, or 9. In certain embodiments, the nucleotide sequence is a nucleotide sequence that encodes an MTM1 polypeptide comprising an amino acid sequence at least 80%, 85%, 90%, 95%, 97%, 98%, 99% or 100% identical to any one or more of SEQ ID NOs: 1, 6, or 8. In certain embodiments, the nucleotide sequence is a nucleotide sequence that encodes an MTM1 polypeptide comprising an amino acid sequence at least 90%, 95%, 97%, 98%, 99% or 100% identical to SEQ ID NO: 1.

In certain embodiments, the nucleic acid constructs may further comprise a nucleotide sequence that encodes a linker.

In certain embodiments, the internalizing moiety may be an antibody or an antigen-binding fragment thereof. In some embodiments, the antibody or antigen-binding fragment thereof may be monoclonal antibody 3E10, or a variant thereof that retains the cell penetrating activity of 3E10, or an antigen-binding fragment of 3E10 or said 3E10 variant. In other embodiments, the antibody or antigen-binding fragment thereof may be an antibody or antigen-binding fragment that binds to the same epitope as 3E10, or an antibody or antigen-binding fragment that has substantially the same cell penetrating activity as 3E10, or an antigen-binding fragment thereof. In certain embodiments, the internalizing moiety may be a homing peptide. In certain embodiments, the internalizing moiety is a homing peptide which targets muscle cells.

In another aspect, the present disclosure provides a composition comprising any of the foregoing chimeric polypeptide compositions or nucleic acid constructs, and a pharmaceutically acceptable carrier. In certain embodiments, the composition may further comprise a second agent which acts in an additive or synergistic manner for treating myotubular myopathy, for having a bioactive effect of MTM1 on cells, and/or for promoting transport into cells. The second agent may be, e.g., a small molecule, a polypeptide, an antibody, an antisense oligonucleotide, or an siRNA molecule.

With respect to nucleic acid constructs, the disclosure contemplates all combinations of any of the foregoing aspects and embodiments, as well as combinations with any of the embodiments set forth in the detailed description and examples.

In further aspects, the present disclosure provides a method of treating myotubular myopathy in a subject in need thereof, comprising administering to the subject an effective amount of any of the foregoing chimeric polypeptides or nucleic acid constructs. In certain embodiments, the method comprising administering a chimeric polypeptide, which polypeptides comprise: (i) an MTM1 polypeptide or bioactive fragment thereof and (ii) an internalizing moiety which promotes transport of said chimeric polypeptide into muscle cells. In certain embodiments, the chimeric polypeptide has phosphoinositide phosphatase activity. In certain embodiments, the subject is a human. In other embodiments, the subject is selected from any of a mouse, rat, or non-human primate.

In some embodiments, the internalizing moiety transits cellular membranes via an ENT2 transporter. In other words, the internalizing moiety promotes transport into cells via an ENT2 transporter. In certain embodiments, the internalizing moiety comprises an antibody or an antigen-binding fragment thereof. In certain embodiments, the internalizing moiety comprises a monoclonal antibody or an antigen-binding fragment thereof. For example, the antibody or antigen-binding fragment thereof may be monoclonal antibody 3E10, or a variant thereof that retains the cell penetrating activity of 3E10, or an antigen-binding fragment of 3E10 or said 3E10 variant. Additionally, the antibody or antigen-binding fragment thereof may be an antibody or antigen-binding fragment that binds to the same epitope as 3E10, or an antibody or antigen-binding fragment that has substantially the same cell penetrating activity as 3E10, or an antigen-binding fragment thereof.

In certain embodiments, the MTM1 polypeptide comprises an amino acid sequence at least 90% identical to SEQ ID NO: 1, or a bioactive fragment thereof. In some embodiments the MTM1 polypeptide comprises an amino acid sequence at least 80%, 85%, 90%, 95%, 97%, 98%, 99% or 100% identical to an MTM1 polypeptide (such as the MTM1 polypeptides represented in one or more of SEQ ID NOs: 1, 6, 8, or a bioactive fragment of any of the foregoing).

In some embodiments, any of the foregoing chimeric polypeptides may be formulated with a pharmaceutically acceptable carrier.

In certain embodiments, the chimeric polypeptides for use in the claimed method may be conjugated (e.g., chemically or recombinantly) as described herein.

In certain embodiments, any of the foregoing methods may further comprise a second therapy which acts in an additive or synergistic manner for treating myotubular myopathy. In some embodiments, the second therapy may be a drug for helping to relieve one or more symptoms of myotubular myopathy, or a physical or other non-drug therapy for treating or otherwise helping to relieve one or more symptoms of myotubular myopathy. Exemplary non-drug therapies include, but are not limited to, ventilatory therapy, occupational therapy, acupuncture, and massage.

In some embodiments, any of the foregoing chimeric polypeptides may be administered via an appropriate route of administration, e.g., systemically, locally, or intravenously. In certain embodiments, the chimeric polypeptide is administered intravenously via bolus injection or infusion.

With respect to methods for treating myotubular myopathy, the disclosure contemplates all combinations of any of the foregoing aspects and embodiments, as well as combinations with any of the embodiments set forth in the detailed description and examples.

In another aspect, the present disclosure provides a method of delivering a chimeric polypeptide or nucleic acid construct into a cell via an equilibrative nucleoside transporter (ENT2) pathway, comprising contacting a cell with a chimeric polypeptide or nucleic acid construct. In certain embodiments, the method comprises contacting a cell with a chimeric polypeptide, which chimeric polypeptide comprises an MTM1 polypeptide or bioactive fragment thereof and an internalizing moiety which mediates transport across a cellular membrane via an ENT2 pathway, thereby delivering the chimeric polypeptide into the cell. In certain embodiments, the cell is a muscle cell.

In certain embodiments, the MTM1 polypeptide comprises an amino acid sequence at least 90% identical to SEQ ID NO: 1, or a bioactive fragment thereof. In some embodiments the MTM1 polypeptide comprises an amino acid sequence at least 80%, 85%, 90%, 95%, 97%, 98%, 99% or 100% identical to an MTM1 polypeptide (such as the MTM1 polypeptides represented in one or more of SEQ ID NOs: 1, 6, 8, or a bioactive fragment of any of the foregoing).

In certain embodiments, the MTM1 polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof. In other embodiments, the internalizing moiety comprises a monoclonal antibody or an antigen-binding fragment thereof. For example, the antibody or antigen-binding fragment thereof may be monoclonal antibody 3E10, or a variant thereof that retains the cell penetrating activity of 3E10, or an antigen-binding fragment of 3E10 or said 3E10 variant. Additionally, the antibody or antigen-binding fragment thereof may be an antibody or antigen-binding fragment that binds to the same epitope as 3E10, or an antibody or antigen-binding fragment that has substantially the same cell penetrating activity as 3E10, or an antigen-binding fragment thereof. In some embodiments, the internalizing moiety may comprise a homing peptide that targets ENT2.

In certain embodiments, the chimeric polypeptides for use in the method may be produced by chemically conjugating the MTM1 polypeptide, or bioactive fragment thereof, to the internalizing moiety. In some embodiments, the chimeric polypeptide may be produced recombinantly to recombinantly conjugate the MTM1 polypeptide, or bioactive fragment thereof, to the internalizing moiety. In certain embodiments, the chimeric polypeptides for use in the claimed method may be conjugated (e.g., chemically or recombinantly) as described herein.

With respect to methods of delivering a chimeric polypeptide into a cell via an equilibrative nucleoside transporter (ENT2) pathway, the disclosure contemplates all combinations of any of the foregoing aspects and embodiments, as well as combinations with any of the embodiments set forth in the detailed description and examples.

In another aspect, the present disclosure provides a method of delivering a chimeric polypeptide into a muscle cell, comprising contacting a muscle cell with a chimeric polypeptide or nucleic acid construct. In certain embodiments, the method comprises contacting the muscle cell with a chimeric polypeptide, which chimeric polypeptide comprises an MTM1 polypeptide or a bioactive fragment thereof and an internalizing moiety which promotes transport into muscle cells, thereby delivering the chimeric polypeptide into the muscle cell. In certain embodiments, the internalizing moiety promotes transport via an equilibrative nucleoside transporter (ENT2) pathway In certain embodiments, the MTM1 polypeptide comprises an amino acid sequence at least 90% identical to SEQ ID NO: 1, or a bioactive fragment thereof. In some embodiments the MTM1 polypeptide comprises an amino acid sequence at least 80%, 85%, 90%, 95%, 97%, 98%, 99% or 100% identical to an MTM1 polypeptide (such as the MTM1 polypeptides represented in one or more of SEQ ID NOs: 1, 6, 8, or a bioactive fragment thereof).

In certain embodiments, the MTM1 polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof. In other embodiments, the internalizing moiety comprises a monoclonal antibody or an antigen-binding fragment thereof. For example, the antibody or antigen-binding fragment thereof may be monoclonal antibody 3E10, or a variant thereof that retains the cell penetrating activity of 3E10, or an antigen-binding fragment of 3E10 or said 3E10 variant. Additionally, the antibody or antigen-binding fragment thereof may be an antibody or antigen-binding fragment that binds to the same epitope as 3E10, or an antibody or antigen-binding fragment that has substantially the same cell penetrating activity as 3E10, or an antigen-binding fragment thereof. In some embodiments, the internalizing moiety may comprise a homing peptide that targets ENT2, and/or a homing peptide that targets muscle cells.

In some embodiments, the chimeric polypeptide of any of the foregoing methods may be produced by chemically conjugating the MTM1 polypeptide, or bioactive fragment thereof, to the internalizing moiety. In other embodiments, the chimeric polypeptide may be produced recombinantly to recombinantly conjugate the MTM1 polypeptide, or bioactive fragment thereof, to the internalizing moiety. In certain embodiments, the chimeric polypeptides for use in the claimed method may be conjugated (e.g., chemically or recombinantly) as described herein.

With respect to methods of delivering a chimeric polypeptide into a cell via an equilibrative nucleoside transporter (ENT2) pathway, the disclosure contemplates all combinations of any of the foregoing aspects and embodiments, as well as combinations with any of the embodiments set forth in the detailed description and examples.

In other aspects, the present disclosure provides a method of delivering a polypeptide to a subject in need thereof, comprising administering to a subject in need thereof a chimeric polypeptide or a nucleic acid construct. In certain embodiments, the method comprises administering a chimeric polypeptide, which chimeric polypeptide comprises an MTM1 polypeptide or a bioactive fragment thereof and an internalizing moiety which promotes transport into muscle cells, thereby delivering the chimeric polypeptide into the muscle cell. In certain embodiments, the internalizing moiety promotes transport via an ENT2 transporter.

In certain embodiments, the MTM1 polypeptide comprises an amino acid sequence at least 90% identical to SEQ ID NO: 1, or a bioactive fragment thereof. In some embodiments the MTM1 polypeptide comprises an amino acid sequence at least 80%, 85%, 90%, 95%, 97%, 98%, 99% or 100% identical to an MTM1 polypeptide (such as the MTM1 polypeptides represented in one or more of SEQ ID NOs: 1, 6, 8, or a bioactive fragment thereof).

In certain embodiments, the MTM1 polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof. In other embodiments, the internalizing moiety comprises a monoclonal antibody or an antigen-binding fragment thereof. For example, the antibody or antigen-binding fragment thereof may be monoclonal antibody 3E10, or a variant thereof that retains the cell penetrating activity of 3E10, or an antigen-binding fragment of 3E10 or said 3E10 variant. Additionally, the antibody or antigen-binding fragment thereof may be an antibody or antigen-binding fragment that binds to the same epitope as 3E10, or an antibody or antigen-binding fragment that has substantially the same cell penetrating activity as 3E10, or an antigen-binding fragment thereof. In some embodiments, the internalizing moiety may comprise a homing peptide that targets ENT2, and/or targets muscle cells.

In some embodiments, the chimeric polypeptide of any of the foregoing methods may be produced by chemically conjugating the MTM1 polypeptide, or bioactive fragment thereof, to the internalizing moiety. In other embodiments, the chimeric polypeptide may be produced recombinantly to recombinantly conjugate the MTM1 polypeptide, or bioactive fragment thereof, to the internalizing moiety. In certain embodiments, the chimeric polypeptides for use in the claimed method may be conjugated (e.g., chemically or recombinantly) as described herein.

In certain embodiments, the subject of any of the foregoing methods may be a human. In some embodiments, the method of delivery may be, e.g., parenteral or intravenous. In certain embodiments, the chimeric polypeptide is administered intravenously, for example, via bolus injection or infusion.

With respect to methods of delivering a chimeric polypeptide into muscle cells, the disclosure contemplates all combinations of any of the foregoing aspects and embodiments, as well as combinations with any of the embodiments set forth in the detailed description and examples.

In another aspect, the present disclosure provides a method of increasing MTM1 bioactivity in a muscle cell, comprising contacting a muscle cell with a chimeric polypeptide, which chimeric polypeptide comprises an MTM1 polypeptide or bioactive fragment thereof and an internalizing moiety which promotes transport into muscle cells, thereby increasing MTM1 bioactivity in the muscle cell. In certain embodiments, the internalizing moiety promotes transport via an ENT2 transporter.

In certain embodiments, the MTM1 polypeptide comprises an amino acid sequence at least 90% identical to SEQ ID NO: 1, or a bioactive fragment thereof. In some embodiments the MTM1 polypeptide comprises an amino acid sequence at least 80%, 85%, 90%, 95%, 97%, 98%, 99% or 100% identical to an MTM1 polypeptide (such as the MTM1 polypeptides represented in one or more of SEQ ID NOs: 1, 6, 8, or bioactive fragments of any of the foregoing).

In certain embodiments, the MTM1 polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof. In other embodiments, the internalizing moiety comprises a monoclonal antibody or an antigen-binding fragment thereof. For example, the antibody or antigen-binding fragment thereof may be monoclonal antibody 3E10, or a variant thereof that retains the cell penetrating activity of 3E10, or an antigen-binding fragment of 3E10 or said 3E10 variant. Additionally, the antibody or antigen-binding fragment thereof may be an antibody or antigen-binding fragment that binds to the same epitope as 3E10, or an antibody or antigen-binding fragment that has substantially the same cell penetrating activity as 3E10, or an antigen-binding fragment thereof. In some embodiments, the internalizing moiety may comprise a homing peptide that targets ENT2, and/or muscle cells.

In other embodiments, the chimeric polypeptide for use in any of the foregoing methods may be produced by chemically conjugating the MTM1 polypeptide, or bioactive fragment thereof, to the internalizing moiety. In other embodiments, the chimeric polypeptide may be produced recombinantly to recombinantly conjugate the MTM1 polypeptide, or bioactive fragment thereof, to the internalizing moiety.

In some embodiments, the MTM1 bioactivity includes, e.g., MTM1 phosphoinositide phosphatase activity, or MTM1 association with an endosomal protein, or both. In certain embodiments, the phosphoinositide activity is at least 50% that of native MTM1, or at least 80% that of native MTM1. In other embodiments, the phosphoinositide activity is at least 30%, 40%, 50%, 60%, 70%, 75%, 80%, 85%, 90%, 95%, or 100% that of native MTM1. Bioactivity can be assessed relative to that in a control.

With respect to methods of increasing MTM1 bioactivity in cells, the disclosure contemplates all combinations of any of the foregoing aspects and embodiments, as well as combinations with any of the embodiments set forth in the detailed description and examples. The foregoing methods based on administering chimeric polypeptides or contacting cells with chimeric polypeptides can be performed in vitro (e.g., in cells or culture) or in vivo (e.g., in a patient or animal model). In certain embodiments, the method is an in vitro method. In certain embodiments, the method is an in vivo method.

In other aspects, the present disclosure also provides a method of producing any of the foregoing chimeric polypeptides as described herein. Further, the present disclosure contemplates any number of combinations of the foregoing methods and compositions.

The invention contemplates all combinations of any of the foregoing aspects and embodiments, as well as combinations with any of the embodiments set forth in the detailed description and examples.

BRIEF DESCRIPTION OF THE TABLES

Table 1. An experimental design to evaluate phosphoinositide phosphatase activity, endosomal association and secretion of genetically conjugated Fv3E10-GS3-hMTM1. Certain predicted results for control groups are indicated by "yes" or "no"; "?" indicates results to-be-measured. "+" or "–" indicates the presence or absence of a particular compound to the sample. "*" indicates that the prediction is based upon the assumption that phosphoinositide activities will be a function of endogenous and hMTM1 dependent activity.

Table 2. An experimental design to evaluate if Fv3E10-GS3-hMTM1 enters cells via ENTs and associates with endosomal proteins. See Table 1 description for notations. "*" indicates that the sample is immunoprecipitated and detected by immunoblot only if immunoprecipitated in Table 1, groups 10 through 18. "**" indicates that prediction is based on the assumption that the genetic conjugate has no defects in association between Vps34 and hMTM1.

Table 3. In vivo dosing plan for chemically and genetically conjugated 3E10-MTM1. Dosing is planned for twice per week over 20 weeks. Blood and tissues will be collected for immunohistochemistry (IHC), hematoxylin and eosin staining (H&E), and protein isolation.

DETAILED DESCRIPTION OF THE INVENTION

Proteins of the MTM family fall into two basic categories: family members that exhibit phosphoinositide phosphatase activity and family members that bind phosphoinositides but are catalytically inactive. MTM1, mutations in which result in myotubular myopathy, is catalytically active and possesses phosphoinositide phosphatase activity. Some examples of phosphoinositides that act as substrates for MTM1 include, but are not limited to, e.g., phosphatidylinositol 3-phosphate (PI(3)P), PI(4)P, PI(5)P, PI(3,4)$P_2$, PI(4,5) $P_2$, PI(3,5) $P_2$, PI(3,4,5) $P_3$, as well as synthetic phosphoinositide compounds useful for in vitro assays. In certain embodiments, the chimeric polypeptide is capable of cleaving or hydrolyzing any one or more of the foregoing phosphoinositides. In certain embodiments, the chimeric polypeptide is capable of cleaving or hydrolyzing PIP3.

MTM1, as well as other related MTM proteins (MTMRs) assemble individually or in heterodimers on endocytic vesicles at various stages of subcellular transport. MTM1 associates with MTMR12 and interacts with other endosomal proteins such as the GTPase Rab5 and the PI 3-kinase hVps34 via the hVps15 adapter molecule. Without being bound by theory, the differential recruitment and opposing activities of MTM1 PIP3 phosphatase and hVps34 PI-3 kinase may coordinate the temporal membrane distribution of PI and PIP3 that directs the intracellular traffic patterns of endocytic vesicles. Although other MTM-related proteins possess phosphoinositide phosphatase activity, their subcellular localization is sufficiently non-overlapping from that of MTM1 that they are unable to functionally compensate for the MTM1 deficiency. MTM1 is ubiquitously expressed yet the absence of MTM1 in skeletal muscle solely accounts for the pathophysiology of MTM (Taylor G S et al., Proc Natl Acad Sci USA. 2000 August 1; 97(16):8910-5; Bello A B et al., *Proc Natl Acad Sci USA.* 2002 November 12; 99(23): 15060-5), and suggests that the phosphoinositide phosphatase activity of MTM1 possesses a unique subcellular function that is particularly crucial to normal skeletal muscle function. It is believed that MTM1 participates in the maintenance of the longitudinal and transverse architecture of the T-tubule system, and thus defects in the organization of these structures would impair excitation-contraction coupling, and result in the ensuing muscle weakness and atrophy that are hallmarks of the disease (Bello A B et al., Human Molecular Genetics, 2008, Vol. 17, No. 14; Laporte J et al., HUMAN MUTATION 15:393.409 (2000); Herman G E et al., THE JOURNAL OF PEDIATRICS VOLUME 134, NUMBER 2; Weisbart R H et al., J Immunol. 2000 June 1; 164(11):6020-6).

In certain aspects, the disclosure provides conjugates of MTM1 (e.g., chimeric polypeptides comprising MTM1 or a bioactive fragment thereof) that may be used to treat conditions associated with MTM1 deficiency, e.g., myotubular myopathy. The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

I. MTM1 Polypeptides

As used herein, the MTM1 polypeptides include various splicing isoforms, variants, fusion proteins, and modified forms of the wildtype MTM1 polypeptide. Such isoforms, bioactive fragments or variants, fusion proteins, and modified forms of the MTM1 polypeptides have at least a portion of the amino acid sequence of substantial sequence identity to the native MTM1 protein, and retain at least one function of the native MTM1 protein. In certain embodiments, a bioactive fragment, variant, or fusion protein of an MTM1 polypeptide comprises an amino acid sequence that is at least 80%, 85%, 90%, 95%, 97%, 98%, 99% or 100% identical to an MTM1 polypeptide (such as the MTM1 polypeptides represented in one or more of SEQ ID NOs: 1, 6, and 8). As used herein, "fragments" are understood to include bioactive fragments or bioactive variants that exhibit "bioactivity" as described herein. That is, bioactive fragments or variants of MTM1 exhibit bioactivity that can be measured and tested. For example, bioactive fragments or variants exhibit the same or substantially the same bioactivity as native (i.e., wild-type, or normal) MTM1 protein, and such bioactivity can be assessed by the ability of the fragment or variant to, e.g., cleave or hydrolyze an endogenous phosphoinositide substrate known in the art, or an artificial phosphoinositide substrate for in vitro assays (i.e., a phosphoinositide phosphatase activity), recruit and/or associate with other proteins such as, for example, the GTPase Rab5, the PI 3-kinase Vps34 or Vps15 (i.e., proper localization), or treat myotubular myopathy. Methods in which to assess any of these criteria are described herein. As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured.

The structure and various motifs of the MTM1 polypeptide have been well characterized in the art (see, e.g., Laporte et al., 2003, Human Molecular Genetics, 12(2): R285-R292; Laporte et al., 2002, Journal of Cell Science 15:3105-3117; Lorenzo et al., 2006, 119:2953-2959). As such, in certain embodiments, various bioactive fragments or variants of the MTM1 polypeptides can be designed and identified by screening polypeptides made, for example, recombinantly from the corresponding fragment of the nucleic acid encoding an MTM1 polypeptide. For example, several domains of MTM1 have been shown to be important for its phosphatase activity or localization. To illustrate, these domains include: Glucosyltransferase, Rab-like GTPase Activator and Myotubularins (GRAM; amino acid positions 29-97 or up to 160 of SEQ ID NO: 1), Rac-Induced recruitment Domain (RID; amino acid positions 161-272 of SEQ ID NO: 1), PTP/DSP homology (amino acid positions 273-471 of SEQ ID NO: 1; catalytic cysteine is amino acid 375 of SEQ ID NO: 1), and SET-interacting domain (SID; amino acid positions 435-486 of SEQ ID NO: 1). Accordingly, any combination of such domains may be constructed to identify fragments or variants of MTM1 that exhibit the same or substantially the same bioactivity as native MTM1. Suitable bioactive fragments can be used to make chimeric polypeptides, and such chimeric polypeptides can be used in any of the methods described herein.

Exemplary fragments that may be used as part of a chimeric polypeptide include, for example: about residues 29-486 of SEQ ID NO: 1. Thus, in certain embodiments, the chimeric polypeptides comprises residues 29-486 of SEQ ID NO: 1.

In certain embodiments, the MTM1 portion of the chimeric polypeptide corresponds to the sequence of human MTM1. For example, the MTM1 portion of the chimeric polypeptide comprises an amino acid sequence at least 90%, 92%, 95%, 96%, 97%, 98%, 99%, or 100% identical to SEQ ID NO: 1.

In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native MTM1 protein, for example, by testing their ability to cleave or hydrolyze a endogenous phosphoinositide substrate or a synthetic phosphoinositide substrate (i.e., phosphoinositide phosphatase activity), recruit and/or associate with other proteins such as, for example, GTPase Rab5, PT 3-kinase hVps34 or hVps15 (i.e., proper localization), or treat myotubular myopathy.

In certain embodiments, the present invention contemplates modifying the structure of an MTM1 polypeptide for such purposes as enhancing therapeutic or prophylactic efficacy, or stability (e.g., ex vivo shelf life and resistance to proteolytic degradation in vivo). Such modified MTM1 polypeptides have the same or substantially the same bioactivity as naturally-occurring (i.e., native or wild-type) MTM1 polypeptide. Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains.

This invention further contemplates generating sets of combinatorial mutants of an MTM1 polypeptide, as well as truncation mutants, and is especially useful for identifying bioactive variant sequences. Combinatorially-derived variants can be generated which have a selective potency relative to a naturally occurring MTM1 polypeptide. Likewise, mutagenesis can give rise to variants which have intracellular half-lives dramatically different than the corresponding wild-type MTM1 polypeptide. For example, the altered protein can be rendered either more stable or less stable to proteolytic degradation or other cellular process which result in destruction of, or otherwise inactivation of the protein of interest. Such variants can be utilized to alter the MTM1 polypeptide level by modulating their half-life. There are many ways by which the library of potential MTM1 variants sequences can be generated, for example, from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp273-289; Itakura et al., (1984) Annu Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, MTM1 polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the MTM1 polypeptide.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the MTM1 polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, an MTM1 polypeptide may include a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the MTM1 polypeptides.

In certain embodiments, an MTM1 polypeptide may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified MTM1 polypeptides may contain non-amino acid elements, such as lipids, poly- or mono-saccharide, and phosphates. Effects of such non-amino acid elements on the functionality of an MTM1 polypeptide may be tested for its biological activity, for example, its ability to treat myotubular myopathy or ability to cleave phosphoinositides (e.g., PIP3). Given that the native MTM1 polypeptide is glycosylated, in certain embodiments an MTM1 polypeptide used in a chimeric polypeptide according to the present disclosure is glycosylated. In certain embodiments, the level and pattern of glycosylation is the same as or substantially the same as that of the native MTM1 polypeptide. In other embodiments, the level and/or pattern of glycosylation differs from that of the native MTM1 polypeptide (e.g., underglycosylated, overglycosylated, not glycosylated).

In one specific embodiment of the present invention, an MTM1 polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

In certain embodiments, fragments or variants of the MTM1 polypeptide will preferably retain at least 50%, 60%, 70%, 80%, 85%, 90%, 95% or 100% of the biological activity associated with the native MTM1 polypeptide. In certain embodiments, fragments or variants of the MTM1 polypeptide have a half-life ($t_{1/2}$) which is enhanced relative to the half-life of the native protein. For embodiments in which the half-life is enhanced, the half-life of MTM1 fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native MTM1 protein. In some embodiments, the protein half-life is determined in vitro, such as in a buffered saline solution or in serum. In other embodiments, the protein half-life is an in vivo half life, such as the half-life of the protein in the serum or other bodily fluid of an animal.

In certain aspects, an MTM1 polypeptide may be a fusion protein which further comprises one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fe), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the MTM1 polypeptides may contain one or more modifications that are capable of stabilizing the polypeptides. For example, such modifications enhance the in vitro half life of the polypeptides, enhance circulatory half life of the polypeptides or reducing proteolytic degradation of the polypeptides. It should be noted that any portion of a chimeric polypeptide of the invention may be similarly epitope tagged. In other words, an epitope tag may be to MTM1 and/or the internalizing moiety. Moreover, the chimeric polypeptides may comprises more than one epitope tags, such as 2 epitope tags, or may include 0 epitope tags.

In some embodiments, an MTM1 protein may be a fusion protein with all or a portion of an Fc region of an immunoglobulin. Similarly, in certain embodiments, all or a portion of an Fc region of an immunoglobulin can be used as a linker to link an MTM1 protein to an internalizing moiety. As is known, each immunoglobulin heavy chain constant region comprises four or five domains. The domains are named sequentially as follows: CH1-hinge-CH2-CH3(-CH4). The DNA sequences of the heavy chain domains have cross-homology among the immunoglobulin classes, e.g., the CH2 domain of IgG is homologous to the CH2 domain of IgA and IgD, and to the CH3 domain of IgM and IgE. As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igϵ) and IgM (Igμ), may be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc γ or the homologous domains in any of IgA, IgD, IgE, or IgM. Furthermore, it is contemplated that substitution or deletion of amino acids within the immunoglobulin heavy chain constant regions may be useful in the practice of the invention. One example would be to introduce amino acid substitutions in the upper CH2 region to create a Fc variant with reduced affinity for Fc receptors (Cole et al. (1997) J. IMMUNOL. 159:3613). One of ordinary skill in the art can prepare such constructs using well known molecular biology techniques.

II. Internalizing Moieties

As used herein, the term "internalizing moiety" refers to a moiety capable of interacting with a target tissue or a cell type to effect delivery of the attached molecule into the cell (i.e., penetrate desired cell; transport across a cellular membrane). In certain embodiments, this disclosure relates to an internalizing moiety which selectively, although not necessarily exclusively, targets and penetrates muscle cells. In certain embodiments, the internalizing moiety has limited cross-reactivity, and thus preferentially targets a particular cell or tissue type. In certain embodiments, suitable internalizing moieties include, for example, antibodies, monoclonal antibodies, or derivatives or analogs thereof. Other internalizing moieties include for example, homing peptides, fusion proteins, receptors, ligands, aptamers, peptidomimetics, and any member of a specific binding pair. In certain embodiments, the internalizing moiety mediates transit across cellular membranes via an ENT2 transporter.

(a) Antibodies

In certain aspects, an internalizing moiety may comprise an antibody, such as a monoclonal antibody, a polyclonal antibody, and a humanized antibody. Without being bound by theory, such antibody can bind to an antigen of a target tissue and thus mediate the delivery of the subject chimeric polypeptide to the target tissue (e.g., muscle). In some embodiments, internalizing moieties may comprise antibody fragments, derivatives or analogs thereof, including without limitation: Fv fragments, single chain Fv (scFv) fragments, Fab' fragments, F(ab')2 fragments, single domain antibodies, humanized antibodies and antibody fragments, and multivalent versions of the foregoing. Multivalent internalizing moieties including without limitation: monospecific or bispecific antibodies, such as disulfide stabilized Fv fragments, scFv tandems ($(scFv)_2$ fragments), diabodies, tribodies or tetrabodies, which typically are covalently linked or otherwise stabilized (i.e., leucine zipper or helix stabilized) scFv fragments; receptor molecules which naturally interact with a desired target molecule. In certain embodiments, the antibodies or variants thereof, may be modified to make them less immunogenic when administered to a subject. For example, if the subject is human, the antibody may be "humanized"; where the complimentarity determining region(s) of the hybridoma-derived antibody has been transplanted into a human monoclonal antibody, for example as described in Jones, P. et al. (1986), *Nature,* 321, 522-525 or Tempest et al. (1991), *Biotechnology,* 9, 266-273. Also, transgenic mice, or other mammals, may be used to express humanized antibodies. Such humanization may be partial or complete. In certain embodiments, although the antibody is a murine or other non-human antibody, its humanness score is sufficient that humanization is not necessary. In still other embodiments, the antibody or antigen-binding fragment is fully human.

In certain specific embodiments, the internalizing moiety comprises the monoclonal antibody 3E10, an antigen-binding fragment thereof, or a single chain Fv fragment thereof. As used herein, the term "antibodies" refers to complete antibodies or antibody fragments capable of binding to a selected target. Included are Fv, scFv, Fab' and F(ab')2, monoclonal and polyclonal antibodies, engineered antibodies, and synthetic or semi-synthetic antibodies produced using phage display or alternative techniques. Monoclonal antibody 3E10 can be reproduced recombinantly or by a hybridoma placed permanently on deposit with the American Type Culture Collection (ATCC) under ATCC accession number PTA-2439 (See U.S. Pat. No. 7,189,396). Additional suitable antibodies have similar or substantially the same membrane penetrating activity as 3E10 and/or bind to the same epitope as 3E10 and/or have substantially the same antigen-binding characteristics as 3E10.

Monoclonal antibody 3E10 has been shown to penetrate cells without toxicity and has attracted considerable interest as a means to deliver proteins and nucleic acids into the cytoplasmic or nuclear spaces of target tissues (Weisbart R H et al., J Autoimmun. 1998 October; 11(5):539-46; Weisbart R H, et al. Mol Immunol. 2003 March; 39(13):783-9; Zack D J et al., J Immunol. 1996 September 1; 157(5):2082-8.). Further, the VH and Vk sequences of 3E10 are highly homologous to human antibodies, with respective humanness z-scores of 0.943 and −0.880. Thus, Fv3E10 is expected to induce less of an anti-antibody response than many other approved humanized antibodies (Abhinandan K R et al., Mol. Biol. 2007 369, 852-862). A single chain Fv fragment of 3E10 possesses all the cell penetrating capabilities of the original monoclonal antibody, and proteins such as catalase, dystrophin, HSP70 and p53 retain their activity following conjugation to Fv3E10 (Hansen J E et al., Brain Res. 2006 May 9; 1088(1):187-96; Weisbart R H et al., Cancer Lett. 2003 June 10; 195(2):211-9; Weisbart R H et al., J Drug Target. 2005 February; 13(2):81-7; Weisbart R H et al., J Immunol. 2000 June 1; 164(11):6020-6; Hansen J E et al., J Biol Chem. 2007 July 20; 282(29):20790-3). The 3E10 is built on the antibody scaffold present in all mammals; a mouse variable heavy chain and variable kappa light chain. 3E10 gains entry to cells via the ENT2 nucleotide transporter that is particularly enriched in skeletal muscle and cancer cells, and in vitro studies have shown that 3E10 is nontoxic. (Weisbart R H et al., Mol Immunol. 2003 March; 39(13):783-9; Pennycooke M et al., Biochem Biophys Res Commun. 2001 January 26; 280(3):951-9). Given the affinity of 3E10 and fragments thereof for skeletal muscle, and the ability of various conjugates of 3E10 and MTM1 to maintain their respective activities, a recombinant 3E10-MTM1 (and other conjugate variants as described herein) therapy represents a valuable approach to treat MTM. As described herein, a recombinant 3E10 or a fragment or variant can be chemically or genetically conjugated to human MTM1 (hMTM1) and the activity of each conjugate may be confirmed in vitro. Further, the purified conjugates may be injected into MTM1 deficient mice and improvements in disease phenotype, as described herein, may be examined.

The internalizing moiety may also include mutants of mAb 3E10, such as variants of 3E10 which retain the same or substantially the same cell penetration characteristics as mAb 3E10, as well as variants modified by mutation to improve the utility thereof (e.g., improved ability to target specific cell types, improved ability to penetrate the cell membrane, improved ability to localize to the cellular DNA, improved binding affinity, and the like). Such mutants include variants wherein one or more conservative substitutions are introduced into the heavy chain, the light chain and/or the constant region(s) of the antibody. Numerous variants of mAb 3E10 have been characterized in, e.g., U.S. Pat. No. 7,189,396 and WO 2008/091911, the teachings of which are incorporated by reference herein in their entirety. In certain embodiments, the internalizing moiety comprises an antibody having an amino acid sequence at least 80%, 85%, 90%, 95%, 96%, 97%, 99%, or 100% identical to the amino acid sequence of 3E10, or at least 80%, 85%, 90%, 95%, 96%, 97%, 99%, or 100% identical to the amino acid sequence of a single chain Fv of 3E10 (for example, a single chain Fv comprising SEQ ID NO: 2 and SEQ ID NO: 4). In certain embodiments, the internalizing moiety comprises a single chain Fv of 3E10, and the amino acid sequence of the $V_H$ domain is at least 90%, 95%, 96%, 97%, 98%, 99%, or 100% identical to SEQ ID NO: 2, and amino acid sequence of the $V_L$ domain is at least 90%, 95%, 96%, 97%, 98%, 99%, or 100% identical to SEQ ID NO: 4. The variant 3E10 or fragment thereof retains the function of an internalizing moiety.

In certain embodiments, the internalizing moiety comprises an antibody or antigen-binding fragment comprising a light chain variable domain (VL) comprising an amino acid sequence at least 90%, 92%, 95%, 96%, 97%, 98%, 99%, or 100% identical to SEQ ID NO: 4. In certain embodiments, the internalizing moiety comprises an antibody or antigen-binding fragment comprising a heavy chain variable domain (VH) comprising an amino acid sequence at least 90%, 92%, 95%, 96%, 97%, 98%, 99%, or 100% identical to SEQ ID NO: 2. In certain embodiments, the internalizing moiety comprises an antibody or antigen-binding fragment comprising: a light chain variable domain (VL) comprising an amino acid sequence at least 90%, 92%, 95%, 96%, 97%, 98%, 99%, or 100% identical to SEQ ID NO: 4 AND a heavy chain variable domain (VH) comprising an amino acid sequence at least 90%, 92%, 95%, 96%, 97%, 98%, 99%, or 100% identical to SEQ ID NO: 2. The invention specifically contemplates internalizing moieties based on any combination of the foregoing VH and VL chains, for example, an internalizing moiety comprising a VH comprising an amino acid sequence at least 98% identical to SEQ ID NO: 2 and a VL at least 96% identical to SEQ ID NO: 4. In certain embodiments, the internalizing moiety comprising a VH comprising the amino acid sequence set forth in SEQ ID NO: 2 and a VL comprising the amino acid sequence set forth in SEQ ID NO: 4. As detailed herein, the VH and VL domains may be included as part of a full length antibody or as part of a fragment, such as an svFv. Moreover, the VH and VL domains may be joined by a linker, or may be joined directly. In either case, the VH and VL domains may be joined in either orientation (e.g., with the VL domain N-terminal to the VH domain or with the VH domain N-terminal to the VL domain).

As readily recognized by those of skill in the art, altered mAb 3E10 (e.g., chimeric, humanized, CDR-grafted, fully human, bifunctional, antibody polypeptide dimers—i,e., an association of two polypeptide chain components of an antibody, such as one arm of an antibody comprising a heavy chain and a light chain, or an Fab fragment comprising $V_L$, $V_H$, $C_L$ and $C_{H1}$ antibody domains, or an Fv fragment comprising a $V_L$ domain and a $V_H$ domain—single chain antibodies—e.g., an scFv fragment comprising a $V_L$ domain linked to a $V_H$ domain by a linker, and the like)—can also be produced by methods well known in the art. Such antibodies can also be produced by hybridoma, chemical synthesis or recombinant methods described, for example, in (Sambrook et al., Molecular Cloning: A Laboratory Manual 2d Ed. (Cold Spring Harbor Laboratory, 1989); incorporated herein by reference and Harlow and Lane, Antibodies: A Laboratory Manual (Cold Spring Harbor Laboratory 1988), which is incorporated herein by reference). Moreover, other antibody internalizing moieties can be readily made and include rodent, chimeric, humanized, fully human, etc.

Preparation of antibodies or fragments thereof (e.g., an single chain Fv fragment encoded by $V_H$-linker-$V_L$) is well known in the art. In particular, methods of recombinant production of mAb 3E10 antibody fragments as well as conjugates thereof (e.g., Fv3E10-GS3-hMTM1, as disclosed herein) have been described in WO 2008/091911. Further, methods of generating scFv fragments of antibodies are well known in the art. The exemplary method of the present disclosure uses a (GGGGS)3 linker (SEQ ID NO: 3) to join a 3E10 VL and VH domain. However, it is understood that other linkers may also be designed. For example, typical surface amino acids in flexible protein regions include Gly, Asn and Ser. Permutations of amino acid sequences containing Gly, Asn and Ser would be expected to satisfy the criteria (e.g., flexible with minimal hydrophobic or charged character) for a linker sequence. Other near neutral amino acids, such as Thr and Ala, can also be used in the linker sequence. In a specific embodiment, a linker sequence length of about 15 amino acids can be used to provide a suitable separation of functional protein domains, although longer or shorter linker sequences may also be used. Moreover, it is understood that, in certain embodiments, a chimeric polypeptide may include an additional linker joining the internalizing moiety to the MTM polypeptide portion of the chimeric polypeptide. Thus, in certain embodiments, chimeric polypeptides may include more than one linker, such as two linkers. For embodiments in which the chimeric polypeptide includes more than one linker, it is understood that the linkers are independently selected and may be the same or different.

Preparation of antibodies and fragments thereof may also be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods (see, for example, Kuby, Janis, *Immunology*, Third Edition, pp. 131-139, W. H. Freeman & Co. (1997), for a general overview of monoclonal antibody production, that portion of which is incorporated herein by reference). Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology,* 2000, 11:445-449, incorporated herein by reference. These methods typically are much less cumbersome than preparation of hybridomas by traditional monoclonal antibody preparation methods. In one embodiment, phage display technology may be used to generate an internalizing moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13. In certain embodiments, an antibody or antibody fragment is made recombinantly. In other words, once the sequence of the antibody is know (for example, using methods described above), the antibody can be made recombinantly using standard techniques. Thus, other antibodies and antigen-binding fragments related to 3E10 or with similar cell penetrating/transiting characteristics can be readily identified by screening, for example, a phage display library.

In certain embodiments, the internalizing moieties may be modified to make them more resistant to cleavage by proteases. For example, the stability of an internalizing moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of an internalizing moiety may be of the D configuration. The switch from L to D amino acids neutralizes the digestion capabilities of many of the ubiquitous peptidases found in the digestive tract. Alternatively, enhanced stability of an internalizing moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of an internalizing moiety may be achieved by intercalating one or more dextrorotatory amino acids (such as, dextrorotatory phenylalanine or dextrorotatory tryptophan) between the amino acids of an internalizing moiety. In exemplary embodiments, such modifications increase the protease resistance of an internalizing moiety without affecting the activity or specificity of the interaction with a desired target molecule.

(b) Homing Peptides

In certain aspects, an internalizing moiety may comprise a homing peptide which selectively directs the subject chimeric MTM1 polypeptide across a cellular membrane and into cells. In certain embodiment, an internalizing moiety may comprise a homing peptide which selectively directs the subject chimeric MTM1 polypeptide to a target tissue (e.g., muscle). For example, delivering a chimeric polypeptide to the muscle can be mediated by a homing peptide comprising an amino acid sequence of ASSLNIA. Further exemplary homing peptides are disclosed in WO 98/53804, which is incorporated by reference in its entirety. Additional examples of homing peptides include the HIV transactivator of transcription (TAT) which comprises the nuclear localization sequence Tat48-60; Drosophila antennapedia transcription factor homeodomain (e.g., Penetratin which comprises Antp43-58 homeodomain 3rd helix); Homo-arginine peptides (e.g., Arg7 peptide-PKC-ϵ agonist protection of ischemic rat heart); alpha-helical peptides; cationic peptides ("superpositively" charged proteins).

Additionally, homing peptides for a target tissue (or organ) can be identified using various methods well known in the art. Once identified, a homing peptide that is selective for a particular target tissue can be used, in certain embodiments.

An exemplary method is the in vivo phage display method. Specifically, random peptide sequences are expressed as fusion peptides with the surface proteins of phage, and this library of random peptides are infused into the systemic circulation. After infusion into host mice, target tissues or organs are harvested, the phage is then isolated and expanded, and the injection procedure repeated two more times. Each round of injection includes, by default, a negative selection component, as the injected virus has the opportunity to either randomly bind to tissues, or to specifically bind to non-target tissues. Virus sequences that specifically bind to non-target tissues will be quickly eliminated by the selection process, while the number of non-specific binding phage diminishes with each round of selection. Many laboratories have identified the homing peptides that are selective for vasculature of brain, kidney, lung, skin, pancreas, intestine, uterus, adrenal gland, retina, muscle, prostate, or tumors. See, for example, Samoylova et al., 1999, *Muscle Nerve,* 22:460; Pasqualini et al., 1996, *Nature,* 380:364; Koivunen et al., 1995, *Biotechnology,* 13:265; Pasqualini et al., 1995, *J. Cell Biol.,* 130:1189; Pasqualini et al., 1996, *Mole. Psych.,* 1:421, 423; Rajotte et al., 1998, *J. Clin. Invest.,* 102:430; Rajotte et al., 1999, *J. Biol. Chem.,* 274:11593. See, also, U.S. Pat. Nos. 5,622,699; 6,068,829; 6,174,687; 6,180,084; 6,232,287; 6,296,832; 6,303,573; 6,306,365.

III. Chimeric Polypeptides

Chimeric polypeptides of the present invention can be made in various manners. In certain embodiments, the C-terminus of an MTM1 polypeptide can be linked to the N-terminus of an internalizing moiety (e.g., an antibody or a homing peptide). Alternatively, the C-terminus of an internalizing moiety (e.g., an antibody or a homing peptide) can be linked to the N-terminus of an MTM1 polypeptide. For example, chimeric polypeptides can be designed to place the MTM1 polypeptide at the amino or carboxy terminus of either the antibody heavy or light chain of mAb 3E10. In certain embodiments, potential configurations include the use of truncated portions of an antibody's heavy and light chain sequences (e.g., mAB 3E10) as needed to maintain the functional integrity of the attached MTM1 polypeptide. Further still, the internalizing moiety can be linked to an exposed internal (non-terminus) residue of MTM1 or a variant thereof. In further embodiments, any combination of the MTM1-internalizing moiety configurations can be employed, thereby resulting in an MTM1: internalizing moiety ratio that is greater than 1:1 (e.g., two MTM1 molecules to one internalizing moiety).

The MTM1 polypeptide and the internalizing moiety may be conjugated directly to each other. Alternatively, they may be linked to each other via a linker sequence, which separates the MTM1 polypeptide and the internalizing moiety by a distance sufficient to ensure that each domain properly folds into its secondary and tertiary structures. Preferred linker sequences (1) should adopt a flexible extended conformation, (2) should not exhibit a propensity for developing an ordered secondary structure which could interact with the functional domains of the MTM1 polypeptide or the internalizing moiety, and (3) should have minimal hydrophobic or charged character, which could promote interaction with the functional protein domains. Typical surface amino acids in flexible protein regions include Gly, Asn and Ser. Permutations of amino acid sequences containing Gly, Asn and Ser would be expected to satisfy the above criteria for a linker sequence. Other near neutral amino acids, such as Thr and Ala, can also be used in the linker sequence. In a specific embodiment, a linker sequence length of about 15 amino acids can be used to provide a suitable separation of functional protein domains, although longer or shorter linker sequences may also be used. The length of the linker sequence separating the MTM1 polypeptide and the internalizing moiety can be from 5 to 500 amino acids in length, or more preferably from 5 to 100 amino acids in length. Preferably, the linker sequence is from about 5-30 amino acids in length. In preferred embodiments, the linker sequence is from about 5 to about 20 amino acids, and is advantageously from about 10 to about 20 amino acids. In other embodiments, the linker joining the MTM1 polypeptide to an internalizing moiety can be a constant domain of an antibody (e.g., constant domain of mAb 3E10 or all or a portion of an Fc region of another antibody). By way of example, the linker that joins MTM1 with an internalizing moiety is GSTSGSGKSSEGKG (SEQ ID NO: 10). In certain embodiments, the linker is a cleavable linker. As noted above, the chimeric polypeptide may include more than one linker, such as a linker joining the internalizing moiety to the MTM polypeptide and a linker joining portions of the internalizing moiety to each other (e.g., a linker joining a VH and VL domain of a single chain Fv fragment). When the chimeric polypeptide includes more than one linker, such as two linkers, the linkers are independently selected and may be the same or different.

In certain embodiments, the chimeric polypeptides of the present invention can be generated using well-known cross-linking reagents and protocols. For example, there are a large number of chemical cross-linking agents that are known to those skilled in the art and useful for cross-linking the MTM1 polypeptide with an internalizing moiety (e.g., an antibody). For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art, including succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (STAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exists a number of other cross-linking agents including homobifunctional and photoreactive cross-linkers. Disuccinimidyl subcrate (DSS), bismaleimidohexane (BMH) and dimethylpimelimidate.2 HCl (DMP) are examples of useful homobifunctional cross-linking agents, and bis-[B-(4-azidosalicylamido)ethyl]disulfide (BASED) and N-succinimidyl-6(4'-azido-2'-nitrophenylamino)hexanoate (SANPAH) are examples of useful photoreactive cross-linkers for use in this invention. For a recent review of protein coupling techniques, see Means et al. (1990) Bioconjugate Chemistry. 1:2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product. Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds. The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules.

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

In certain specific embodiments, chimeric polypeptides of the invention can be produced by using a universal carrier system. For example, an MTM1 polypeptide can be conjugated to a common carrier such as protein A, poly-L-lysine, hex-histidine, and the like. The conjugated carrier will then form a complex with an antibody which acts as an internalizing moiety. A small portion of the carrier molecule that is responsible for binding immunoglobulin could be used as the carrier.

In certain embodiments, chimeric polypeptides of the invention can be produced by using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). In any of the foregoing methods of cross-linking for chemical conjugation of MTM1 to an internalizing moiety, a cleavable domain or cleavable linker can be used. Cleavage will allow separation of the internalizing moiety and the MTM1 polypeptide. For example, following penetration of a cell by a chimeric polypeptide, cleavage of the cleavable linker would allow separation of MTM1 from the internalizing moiety.

In certain embodiments, the chimeric polypeptides of the present invention can be generated as a fusion protein containing a MTM1 polypeptide and an internalizing moiety (e.g., an antibody or a homing peptide), expressed as one contiguous polypeptide chain. Such chimeric polypeptides are referred to herein as recombinantly conjugated. In preparing such fusion proteins, a fusion gene is constructed comprising nucleic acids which encode an MTM1 polypeptide and an internalizing moiety, and optionally, a peptide linker sequence to span the MTM1 polypeptide and the internalizing moiety. The use of recombinant DNA techniques to create a fusion gene, with the translational product being the desired fusion protein, is well known in the art. Both the coding sequence of a gene and its regulatory regions can be redesigned to change the functional properties of the protein product, the amount of protein made, or the cell type in which the protein is produced. The coding sequence of a gene can be extensively altered—for example, by fusing part of it to the coding sequence of a different gene to produce a novel hybrid gene that encodes a fusion protein. Examples of methods for producing fusion proteins are described in PCT applications PCT/US87/02968, PCT/US89/03587 and PCT/US90/07335, as well as Traunecker et al. (1989) Nature 339:68, incorporated by reference herein. Essentially, the joining of various DNA fragments coding for different polypeptide sequences is performed in accordance with conventional techniques, employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, Eds. Ausubel et al. John Wiley & Sons: 1992). The chimeric polypeptides encoded by the fusion gene may be recombinantly produced using various expression systems as is well known in the art (also see below).

Recombinantly conjugated chimeric polypeptides include embodiments in which the MTM1 polypeptide is conjugated to the N-terminus or C-terminus of the internalizing moiety.

In some embodiments, the immunogenicity of the chimeric polypeptide may be reduced by identifying a candidate T-cell epitope within a junction region spanning the chimeric polypeptide and changing an amino acid within the junction region as described in U.S. Patent Publication No. 2003/0166877.

Chimeric polypeptides of the invention have any of a number of uses. For example, the chimeric polypeptides can be used to identify binding partners of MTM1, such as proteins to which MTM1 endogenously binds, or substrates for MTM1. Chimeric polypeptides can also be used to image skeletal muscle cells, such as MTM1 deficient skeletal muscle cells, and to study the subcellular localization of MTM1 in wildtype or MTM1 deficient skeletal muscle cells. Chimeric polypeptides can also be used as part of a therapeutic method to replace MTM1 protein in deficient cells, in animals, or in human patients. Chimeric polypeptides can be used alone or as part of a therapeutic regimen for treating myotubular myopathy.

IV. MTM1-Related Nucleic Acids and Expression

In certain embodiments, the present invention makes use of nucleic acids for producing an MTM1 polypeptide (including bioactive fragments, variants, and fusions thereof). In certain specific embodiments, the nucleic acids may further comprise DNA which encodes an internalizing moiety (e.g., an antibody or a homing peptide) for making a recombinant chimeric protein of the invention. All these nucleic acids are collectively referred to as MTM1 nucleic acids.

The nucleic acids may be single-stranded or double-stranded, DNA or RNA molecules. In certain embodiments, the disclosure relates to isolated or recombinant nucleic acid sequences that are at least 80%, 85%, 90%, 95%, 97%, 98%, 99% or 100% identical to a region of an MTM1 nucleotide sequence (e.g., SEQ ID NOs: 5, 7, and 9). In further embodiments, the MTM1 nucleic acid sequences can be isolated, recombinant, and/or fused with a heterologous nucleotide sequence, or in a DNA library.

In certain embodiments, MTM1 nucleic acids also include nucleotide sequences that hybridize under highly stringent conditions to any of the above-mentioned native MTM1 nucleotide sequence, or complement sequences thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the native MTM1 nucleic acids due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant MTM1 nucleic acids may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used. In certain aspects, this invention relates to an expression vector comprising a nucleotide sequence encoding an MTM1 polypeptide and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

This invention also pertains to a host cell transfected with a recombinant gene which encodes an MTM1 polypeptide, an internalizing moiety, or a chimeric polypeptide of the invention. The host cell may be any prokaryotic or eukaryotic cell. For example, an MTM1 polypeptide or a chimeric polypeptide may be expressed in bacterial cells such as *E. coli*, insect cells (e.g., using a baculovirus expression system), yeast, or mammalian cells. Other suitable host cells are known to those skilled in the art.

The present invention further pertains to methods of producing an MTM1 polypeptide, an internalizing moiety, and/or a chimeric polypeptide of the invention. For example, a host cell transfected with an expression vector encoding an MTM1 polypeptide, an internalizing moiety, or a chimeric polypeptide can be cultured under appropriate conditions to allow expression of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art. The polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptides (e.g., an MTM1 polypeptide). In a preferred embodiment, the polypeptide is a fusion protein containing a domain which facilitates its purification.

A recombinant MTM1 nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/nco, pRc/CMV, pSV2gpt, pSV2nco, pSV2-dhfr, pTk2, pRSVnco, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

It should be understood that chimeric polypeptides can be made in numerous ways. For example, an MTM1 polypeptide and an internalizing moiety can be made separately, such as recombinantly produced in two separate cell cultures from nucleic acid constructs encoding their respective proteins. Once made, the proteins can be chemically conjugated directly or via a linker. By way of another example, the chimeric polypeptide can be made as an inframe fusion in which the entire chimeric polypeptide, optionally including one or more linker, is made from a nucleic acid construct that includes nucleotide sequence encoding both the MTM1 polypeptide and the internalizing moiety.

V. Methods of Treatment

In certain embodiments, the present invention provides methods of treating conditions associated with deficient or non-functional myotubularin 1 (MTM1) protein, such as myotubular myopathy. These methods involve administering to an individual in need thereof a therapeutically effective amount of a chimeric polypeptide as described above. Specifically, the method comprises administering a chimeric polypeptide comprising (a) a myotubularin (MTM1) polypeptide or bioactive fragment thereof and (b) an internalizing moiety. These methods are particularly aimed at therapeutic and prophylactic treatments of animals, and more particularly, humans.

MTM is a rare and severe X-linked muscle disorder that occurs with an estimated incidence of 1 male in every 50,000 births and is caused by a deficiency of MTM1, a phosphoinositide phosphatase (Bello A B et al., Human Molecular Genetics, 2008, Vol. 17, No. 14). At birth MTM patients present with severe hypotonia and respiratory distress and those that survive the neonatal period are often totally or partially dependent upon ventilator support (Taylor G S et al., Proc Natl Acad Sci USA. 2000 August 1; 97(16):8910-5; Bello A B et al., *Proc Natl Acad Sci USA.* 2002 November 12; 99(23):15060-5; Pierson C R et al., Neuromuscul Disord. 2007 July; 17(7): 562-568; Herman G E et al., THE JOURNAL OF PEDIATRICS VOLUME 134, NUMBER 2). Patients with MTM exhibit delayed motor milestones and are susceptible to complications such as scoliosis, malocclusion, pyloric stenosis, spherocytosis, and gall and kidney stones, yet linear growth and intelligence are normal and the disease follows a non-progressive course (Herman G E et al., THE JOURNAL OF PEDIATRICS VOLUME 134, NUMBER 2). An additional complication is that MTM patients are particularly susceptible to severe and even life threatening respiratory infections. Without being bound by theory, these respiratory infections may be due to the decreased ability of individuals to produce and clear mucous, as well as weakening of lung tissue brought about by long term ventilator use. The average hospital stay for neonatal MTM patients is ~90 days, and the need for long-term ventilatory assistance and in-home care, as well as the costs associated with medical complications impose a substantial personal and economic burden to patients and families.

MTMs are a family of related proteins that exhibit phosphoinositide phosphatase activity or alternatively bind phosphoinositides but are catalytically inactive. MTM1, as well as other related MTM proteins (MTMRs) assemble individually or in heterodimers on endocytic vesicles at various stages of subcellular transport. MTM1 associates with MTMR12 and interacts with other endosomal proteins such the GTPase Rab5 and the PI 3-kinase Vps34 via the Vps15 adapter molecule. The differential recruitment and opposing activities of MTM1 PIP3 phosphatase and Vsp34 PI-3 kinase likely coordinate the temporal membrane distribution of P1 and PIP3 that directs the intracellular traffic patterns of endocytic vesicles. Although other MTM-related proteins possess PIP3 phosphatase activity, their subcellular localization is sufficiently non-overlapping from that of MTM1 that they are unable to functionally compensate for the absence of MTM1. MTM1 is ubiquitously expressed yet the absence of MTM1 in skeletal muscle solely accounts for the pathophysiology of MTM (Blondeau F et al., *Hum Mol Genet.* 2000 September 22; 9(15):2223-9; Taylor G S et al., Proc Natl Acad Sci USA. 2000 August 1; 97(16):8910-5; Bello A B et al., *Proc Natl Acad Sci USA.* 2002 November 12; 99(23):15060-5), and suggests that the PIP3 phosphatase activity of MTM1 possesses a unique subcellular function that is particularly crucial to normal skeletal muscle function. MTM1 is expected to participate in the maintenance of the longitudinal and transverse architecture of the T-tubule system, and thus defects in the organization of these structures would impair excitation-contraction coupling, and result in the ensuing muscle weakness and atrophy (Bello A B et al., Human Molecular Genetics, 2008, Vol. 17, No. 14; Laporte J et al., HUMAN MUTATION 15:393.409 (2000); Herman G E et al., THE JOURNAL OF PEDIATRICS VOLUME 134, NUMBER 2).

Given that the identity of particular endosomal compartments may consist as a defined ratio and distribution of PI and its phosphorylated forms, a therapeutic approach that either blocks PI-3 kinase and/or alternatively increases PIP4 (also "PI(4)P"), PIP5 (also "PI(5)P") or PIP4,5 (also "PI(4,5)$P_2$") is not likely to impart any therapeutic specificity towards MTM. MTM1, MTMR1 and MTMR2 are the most closely related phosphoinositide phosphatases and are expressed in skeletal muscle, and suggests that pharmacologic upregulation of other MTMRs could provide a compensatory benefit to MTM. However, the subcellular locations of MTMR1, MTMR2 and MTM1 do not sufficiently overlap (Lorenzo O et al., Journal of Cell Science 119, 2953-2959 2005) and the mutation of MTMR2 in the recessive motor and sensory demyelinating neuropathy Charcot-Marie-Tooth type 4B (CMT4B) presents with pathological and clinical manifestations that are very different to those of MTM. Therefore, compensatory upregulation of MTMR2 or other MTM-related proteins is likely to provide little, if any, therapeutic compensation for MTM1 deficiency. The mRNA rescue technologies based upon stop codon read-through may be effective for ~20% of MTM patients yet there is no indication that technologies based upon exon skipping will be useful for the ~50% patients possessing deletions and splice site mutations (Laporte J et al., HUMAN MUTATION 15:393.409 (2000)). An approach based upon IGF administration, myostatin inhibition or AKT activation would not correct the underlying biochemical defect of MTM but could counteract any hypotrophic signaling that may exist in MTM.

An approach that restores MTM1 to skeletal muscle either through gene, stem cell or recombinant intravenous therapy is a desirable therapeutic strategy for MTM. In certain embodiments, the present disclosure provides chimeric polypeptides suitable for use in methods for treating MTM. Exemplary chimeric polypeptides comprise (a) an MTM1 polypeptide or a bioactive fragment thereof and (b) an internalizing moiety. In certain embodiments, the internalizing moiety selectively targets the chimeric polypeptide to muscle cells and/or transits cellular membranes via the ENT2 transporter.

Intravenous delivery of recombinant MTM1 may provide the greatest flexibility in dosing with the fewest logistical barriers to development. For example, dosing of intravenous MTM1 can be titrated to effect, or withdrawn if a particular patient experiences a side effect.

MTM1 is a cytoplasmic enzyme and possesses no inherent muscle internalizing moiety, therefore MTM1 may be conjugated to a cell permeable protein to traverse the skeletal muscle sarcolemma and reach the appropriate cytoplasmic compartments. Since MTM1 has been shown to retain PIP3 phosphatase activity following numerous genetic fusions such as N and C-terminal genetic conjugation to purification tags such as GST and 6-His (Kim S A et al., J. Biol. Chem., Vol. 277, Issue 6, 4526-4531, Feb. 8, 2002), and fluorescent reporters such as red and green fluorescent protein (Chaussade C et al., Molecular Endocrinology 17 (12): 2448-2460 2003), MTM1 is expected to retain activity following chemical and genetic conjugation to, e.g., Fv3E10, a muscle internalizing single chain antibody. Additionally, hMTM1 maintains the ability to localize to early endosomes and immunoprecipitate accessory proteins such as Vps15 and Vps34 following genetic conjugation to 6-His and GST purification tags (Taylor G S et al., Proc Natl Acad Sci USA. 2000 August 1; 97(16):8910-5; Cao C et al., Traffic 2007; 8: 1052-1067; Kim S A et al., J. Biol. Chem., Vol. 277, Issue 6, 4526-4531, Feb. 8, 2002), Green and Red Fluorescent Proteins (Cao C et al., Traffic 2007; 8: 1052-1067; Chaussade C et al., Molecular Endocrinology 17 (12): 2448-2460 2003; Robinson F L et al., Trends in Cell Biology, 2006, 16(8): 403-412), and flag epitope tagging (Cao C et al., Traffic 2007; 8: 1052-1067; Kim S A et al., J. Biol. Chem., Vol. 277, Issue 6, 4526-4531, Feb. 8, 2002). Therefore, chemical and genetic conjugates of 3E10 and hMTM1 will retain the ability to penetrate cells, cleave PIP3 to PI, and associate with endosomal proteins.

The terms "treatment", "treating", and the like are used herein to generally mean obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). For example, "treatment" of MTM encompasses a complete reversal or cure of the disease, or any range of improvement in conditions and/or adverse effects attributable to MTM. Merely to illustrate, "treatment" of MTM includes an improvement in any of the following effects associated with MTM or combination thereof: short life expectancy, respiratory insufficiency (partially or completely), poor muscle tone, drooping eyelids, poor strength in proximal muscles, poor strength in distal muscles, facial weakness with or without eye muscle weakness, abnormal curvature of the spine, joint deformities, and weakness in the muscles that control eye movement (ophthalmoplegia). Improvements in any of these conditions can be readily assessed according to standard methods and techniques known in the art. The population of subjects treated by the method of the disease includes subjects suffering from the undesirable condition or disease, as well as subjects at risk for development of the condition or disease.

By the term "therapeutically effective dose" or "effective amount" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

In certain embodiments, one or more chimeric polypeptides of the present invention can be administered, together (simultaneously) or at different times (sequentially). In addition, chimeric polypeptides of the present invention can be administered in combination with one or more additional compounds or therapies for treating myotubular myopathy or for treating neuromuscular disorders in general. For example, one or more chimeric polypeptides can be co-administered in conjunction with one or more therapeutic compounds. The combination therapy may encompass simultaneous or alternating administration. In addition, the combination may encompass acute or chronic administration. Optionally, the chimeric polypeptide of the present invention and additional compounds act in an additive or synergistic manner for treating myotubular myopathy. By way of example, the present method may be used in combination with any of the MTM therapeutic methods as described above (e.g., compensatory upregulation of MTMR2 or other MTM-related proteins, or mRNA rescue technologies based upon stop codon read-through) to achieve an additive or synergistic effect. Additional compounds to be used in combination therapies include, but are not limited to, small molecules, polypeptides, antibodies, antisense oligonucleotides, and siRNA molecules. Further, combination therapy also includes the methods disclosed herein together with other therapies for MTM (e.g., physical therapy, ventilatory support, occupational therapy, accupuncture, etc.). Depending on the nature of the combinatory therapy, administration of the chimeric polypeptides of the invention may be continued while the other therapy is being administered and/or thereafter. Administration of the chimeric polypeptides may be made in a single dose, or in multiple doses. In some instances, administration of the chimeric polypeptides is commenced at least several days prior to the other therapy, while in other instances, administration is begun either immediately before or at the time of the administration of the other therapy.

Regardless of whether the chimeric polypeptide is adminstered as a sole or conjoint therapy, methods of treating including administering a single dose or multiple doses. Multiple doses include administering the chimeric polypeptide at specified intervals, such as daily, weekly, twice monthly, monthly, etc. Multiple doses include an administration scheme in which chimeric polypeptide is administered at specified intervals for the life of the patient.

VI. Gene Therapy

Conventional viral and non-viral based gene transfer methods can be used to introduce nucleic acids encoding polypeptides of MTM1 in mammalian cells or target tissues. Such methods can be used to administer nucleic acids encoding polypeptides of the invention (e.g., MTM1, including variants thereof) to cells in vitro. In some embodiments, the nucleic acids encoding MTM1 are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Such methods are well known in the art.

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection methods and lipofection reagents are well known in the art (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art.

The use of RNA or DNA viral based systems for the delivery of nucleic acids encoding MTM1 or its variants take advantage of highly evolved processes for internalizing a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SW), human immuno deficiency virus (HIV), and combinations thereof, all of which are well known in the art.

In applications where transient expression of the polypeptides of the invention is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures. Construction of recombinant AAV vectors are described in a number of publications, including U.S. Pat. No. 5,173,414; Tratschin et al., *Mol. Cell. Biol.* 5:3251-3260 (1985); Tratschin, et al.;

*Mol. Cell. Biol.* 4:2072-2081 (1984); Hermonat & Muzyczka, *PNAS* 81:6466-6470 (1984); and Samulski et al., *J. Virol.* 63:03822-3828 (1989).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system.

Replication-deficient recombinant adenoviral vectors (Ad) can be engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity.

Packaging cells are used to form virus particles that are capable of infecting a host cell. Such cells include 293 cells, which package adenovirus, and 42 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells, such as muscle cells.

Gene therapy vectors can be delivered in vivo by administration to an individual patient, by systemic administration (e.g., intravenous, intraperitoneal, intramuscular, subdermal, or intracranial infusion) or topical application. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. For example, cells are isolated from the subject organism, transfected with a nucleic acid (gene or cDNA) encoding, e.g., MTM1 or its variants, and re-infused back into the subject organism (e.g., patient). Various cell types suitable for ex vivo transfection are well known to those of skill in the art.

In certain embodiments, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Stem cells are isolated for transduction and differentiation using known methods.

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described herein.

VII. Methods of Administration

Various delivery systems are known and can be used to administer the chimeric polypeptides of the invention, e.g., various formulations, encapsulation in liposomes, microparticles, microcapsules, recombinant cells capable of expressing the compound, receptor-mediated endocytosis (see, e.g., Wu and Wu, 1987, J. Biol. Chem. 262:4429-4432). Methods of introduction can be enteral or parenteral, including but not limited to, intradermal, transdermal, intramuscular, intraperitoneal, intravenous, subcutaneous, pulmonary, intranasal, intraocular, epidural, and oral routes. In particular embodiments, parenteral introduction includes intramuscular, subcutaneous, intravenous, intravascular, and intrapericardial administration.

The chimeric polypeptides may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In certain embodiments, it may be desirable to administer the chimeric polypeptides of the invention locally to the area in need of treatment (e.g., muscle); this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In other embodiments, the chimeric polypeptides of the invention can be delivered in a vesicle, in particular, a liposome (see Langer, 1990, Science 249:1527-1533). In yet another embodiment, the chimeric polypeptides of the invention can be delivered in a controlled release system. In another embodiment, a pump may be used (see Langer, 1990, supra). In another embodiment, polymeric materials can be used (see Howard et al., 1989, J. Neurosurg. 71:105). In certain specific embodiments, the chimeric polypeptides of the invention can be delivered intravenously.

In certain embodiments, the chimeric polypeptides are administered by intravenous infusion. In certain embodiments, the chimeric polypeptides are infused over a period of at least 10, at least 15, at least 20, or at least 30 minutes. In other embodiments, the chimeric polypeptides are infused over a period of at least 60, 90, or 120 minutes. Regardless of the infusion period, the invention contemplates that each infusion is part of an overall treatment plan where chimeric polypeptide is administered according to a regular schedule (e.g., weekly, monthly, etc.).

VIII. Pharmaceutical Compositions

In certain embodiments, the subject chimeric polypeptides of the present invention are formulated with a pharmaceutically acceptable carrier. One or more chimeric polypeptides can be administered alone or as a component of a pharmaceutical formulation (composition). The chimeric polypeptides may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject chimeric polypeptides include those suitable for oral, nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of therapeutic agents and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject polypeptide therapeutic agent as an active ingredient. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral administration (capsules, tablets, pills, dragees, powders, granules, and the like), one or more polypeptide therapeutic agents of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Pharmaceutical compositions suitable for parenteral administration may comprise one or more chimeric polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more polypeptide therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In certain embodiments, the chimeric polypeptides of the present invention are formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the chimeric polypeptides of the invention which will be effective in the treatment of a tissue-related condition or disease (e.g., myotubular myopathy) can be determined by standard clinical techniques. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20-5000 micrograms of the active chimeric polypeptide per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

In certain embodiments, chimeric polypeptides and compositions of the disclosure, including pharmaceutical preparations, are non-pyrogenic. In other words, in certain embodiments, the compositions are substantially pyrogen free. In one embodiment the formulations of the invention are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in relatively large dosages and/or over an extended period of time (e.g., such as for the patients entire life), even small amounts of harmful and dangerous endotoxin could be dangerous. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

The foregoing applies to any of the chimeric polypeptides, compositions, and methods described herein. The invention specifically contemplates any combination of the features of such chimeric polypeptides, compositions, and methods (alone or in combination) with the features described for the various pharmaceutical compositions and route of administration described in this section.

IX. Animal Models of MTM

Mice possessing a targeted inactivation of the MTM1 gene (MTM1 KO) are born at a submendellian distribution but otherwise appear normal. However, within the first weeks of life MTM1 KO mice begin to lose muscle mass that rapidly progresses to respiratory collapse and death at a median age of 7 weeks (14 weeks maximum). Myofibers of MTM KO mice appear hypotrophic and vacuolated with centrally located nuclei surrounded by mitochondria and glycogen, yet there is very little sarcolemma damage and no evidence of apoptosis or inflammation. Ultrastructurally, MTM1 protein appears at submembranous and vesicles of the cytoplasm; and the triads of the T-tubule system of skeletal muscle (Bello A B et al., *Proc Natl Acad Sci USA.* 2002 November 12; 99(23):15060-5). Since the deficiency of MTM1 in skeletal muscle solely accounts for the phenotype in MTM1 KO mice, the constructs disclosed herein may be assessed for therapeutic efficacy using the MTM1 KO mouse model. Further, mice possessing a targeted partial inactivation of the MTM1 gene can also serve as a suitable model system for the present invention. Such mouse models are known in the art. For example, in MTM1δ4 mice, exon 4 is replaced by a loxP site and the Cre allele is absent (Buj-Bello et al., 2002, PNAS 99(23):15060-15065).

Accordingly, in certain embodiments, the present disclosure contemplates methods of surveying improvements in disease phenotype using the MTM1 constructs (e.g., the chimeric polypeptides comprising MTM1) disclosed herein in a mouse model of MTM. Studies in MTM1 deficient mice demonstrate the marked phenotypic differences between wild-type and MTM1 deficient mice (see, e.g., Buj-Bello et al., 2002, PNAS 99(23):15060-15065). For example, a clear divergence in weight gain between normal and MTM1 deficient mice can be seen at ~3 weeks of age. (Bello A B et al., *Proc Natl Acad Sci USA.* 2002 November 12; 99(23): 15060-5) Also, hanging assessment tests indicate a dramatic difference in the hanging performance between MTM1 deficient mice and normal mice. Additionally, MTM1 deficient mice demonstrate a significant deterioration in grip strength (e.g., forelimb grip) as compared to normal mice. Further, compared to normal mice which manifest almost no foot dragging, MTM1 deficient mice demonstrate increased foot dragging as determined by gait analysis. Detailed protocols for evaluating the effect of chimeric polypeptides comprising MTM1 in this animal model are described herein (Example 4).

As such, upon administration (e.g., intravenously) to the MTM1 deficient mice, the ability of the chemical and/or genetic conjugate of a chimeric polypeptide comprising MTM1 (for example, the 3E10-hMTM1 chimeric polypeptide outlined in the examples) to improve one or more symptoms in MTM1 deficient mice (e.g., increase body weight and lifespan, decrease foot drag, improve forelimb grip strength, improve the ability of the treated mice to support themselves against the force of gravity. Further experiments can also assess any improvement in isometric contraction force of selected skeletal muscles, increased myofiber cross-sectional area, reduced central nuclei, morphometry, light/fluorescence microscopy, spontaneous activity, ex vivo myography, and normalized NADH-TR staining. The serum and tissue levels of 3E10-hMTM1, as well as the development of any anti-3E10-hMTM1 antibodies will also be evaluated using immunological-based detection methods.

Moreover, once it is established that 3E10*MTM1 or MTM1 genetic fusion (e.g., 3E10-GS3-hMTM1 or 3E10-GSTS-hMTM1) results in an improvement in phenotype, a complete pharmacokinetic study to determine the effective dose, clearance rate, volume of distribution, and half-life of 3E10-MTM1 can be determined. The pharmacokinetics of 3E10-MTM1 will likely follow a multi-compartment model in which various tissues exhibit different degrees of clearance, and simple assessments of serum half-life will not provide sufficient information to calculate a therapeutic dosing rate. Therefore, the calculation of a dose and dosing rate will ultimately be derived from empirical observations of the pharmacokinetics, pharmacodynamics, toxicology of a given dose of 3E10-MTM1, and the rate and extent to which an increase in weight, wire-hang time, forelimb grip strength, foot drag, spontaneous activity, myofiber diameter and lifespan, for example, are observed. The dose and dosing rate of 3E10-MTM1 determined in a subsequent pharmacokinetic study can be the used as the standard comparator to evaluate optimized lots of recombinant 3E10-MTM1. The PK/PD/TK of the final product will then be examined in larger animals such as rats, dogs, and primates.

The above mouse models provide a suitable animal model system for assessing the activity and effectiveness of the subject chimeric polypeptides. Further these models correlate strongly with MTM, and provide an appropriate model for MTM. Activity of the polypeptide can be assessed in these mouse models, and the results compared to that observed in wildtype control animals and animals not treated with the chimeric polypeptides. The results can be evaluated by examining the mice, as well as by examining the ultrastructure of their muscle cells. Similarly, the subject chimeric polypeptides can be evaluated using cells in culture, for example, cells prepared from the mutant mice.

In other embodiments, a large animal model can also be used to assess the activity and effectiveness of the subject chimeric polypeptides. By way of example, a dog model may be a particularly useful system for studying MTM. The affected dog carries a deficient MTM1 gene and, therefore, the studies described herein for a mouse model similarly apply to a dog model. The evaluation dose of 3E10 chemically or genetically conjugated to hMTM1 delivered to MTM1 deficient dogs will be determined empirically.

X. Other Suitable Models

Other suitable models for evaluating the activity of the chimeric polypeptides of the invention include cell free and cell based assays. Chimeric polypeptides will possess two properties: a bioactivity of MTM1 and a cell penetrating activity of the internalizing moiety that promotes transfer across cell membrane and into cells. Suitable models allow evaluation of one or both of these activities.

By way of example, the chimeric polypeptides can be evaluated for cell penetrating activity using primary cells in culture or a cell line. The cells are contacted with the chimeric polypeptide and assayed to determine whether and to what extent the chimeric polypeptide entered the cell. For example, IHC can be used to evaluate whether the chimeric polypeptide entered the cell, and the results compared to an appropriate control. In certain embodiments in which transfer into the cell is thought to occur via the ENT2 transporter, cells can be examined in the presence or absence of an ENT2 transporter inhibitor.

Further, as described herein, the chimeric polypeptides of the present invention can be used to test for functionality in cell-based assays. In an exemplary embodiment, primary muscle cells from MTM1 deficient mice (e.g., MTM1δ4) can be used to determine whether treatment with the chimeric polypeptides described herein can improve the fusion deficiency of myotubularin deficient myoblasts. Detailed methods are exemplified herein.

By way of further example, bioactivity of MTM1 can be measured in cell free assays, for example, to confirm that the chimeric polypeptide retains the ability to bind suitable binding partners and/or retains phosphatase activity. Similar assays can be conducted in primary cells in culture or in a cell line in culture.

XI. Kits

In certain embodiments, the invention also provides a pharmaceutical package or kit comprising one or more containers filled with at least one chimeric polypeptide of the invention. Exemplary containers include, but are not limited to, vials, bottles, pre-filled syringes, IV bags, blister packs (comprising one or more pills). Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

EXEMPLIFICATION

The invention now being generally described, it will be more readily understood by reference to the following examples, which are included merely for purposes of illustration of certain aspects and embodiments of the present invention, and are not intended to limit the invention. For example, the particular constructs and experimental design disclosed herein represent exemplary tools and methods for validating proper function. As such, it will be readily apparent that any of the disclosed specific constructs and experimental plan can be substituted within the scope of the present disclosure.

Example 1

Chemical Conjugation of 3E10 and hMTM1 (mAb3E10*hMTM1)

Chemical Conjugation

Monoclonal Ab 3E10 is of the IgG2a subtype and is derived from the fusion of spleen cells from an MRL/lpr/mpj mouse with FOX-NY hybridoma cells (Mankodi A et al., Mol Cell. 2002 July; 10(1):35-44). Ten milligrams (10 mg) of mAb 3E10 is conjugated covalently to recombinant human MTM1 (AbNova) in a 1/1 molar ratio with the use of two different heterobifunctional reagents, succinimidyl 3-(2-pyridyldithio) propionate and succinimidyl trans-4-(maleimidylmethyl) cyclo-hexane-1-carboxylate. This reaction modifies the lysine residues of mAb 3E10 into thiols and adds thiolreactive maleimide groups to MTM1 (Weisbart R H, et al., J Immunol. 2000 June 1; 164(10:6020-6). After deprotection, the modified proteins are reacted to each other to create a stable thioether bond. Chemical conjugation is performed, and the products are fractionated by gel filtration chromatography. The composition of the fractions are assessed by native and SDS-PAGE in reducing and nonreducing environments. Fractions containing the greatest ratio of mAb 3E10*hMTM1 chemical conjugate to free mAb 3E10 and free hMTM1 are pooled and selected for use in further studies.

Additional chemical conjugates are similarly made for later testing. By way of non-limiting example: (a) hMTM1*3E10, (b) Fv3E10*hMTM1, (c) hMTM1*Fv3E10. Note that throughout the example, the abbreviation Fv is used to refer to a single chain Fv of 3E10. Similarly, mAb 3E10 and 3E10 are used interchangeably. These and other chimeric polypeptides can be tested for enzymatic activity and functionality using, for example, the assays detailed herein. Any chimeric polypeptide comprising an MTM1 portion and an internalizing moiety can be similarly tested to confirm that the chimeric polypeptide maintains the activity of MTM1 and the cell penetrating activity of the internalizing moiety. Reference to any particular chimeric polypeptide in these examples is merely for example. In certain embodiments, a chimeric polypeptide comprising the amino acid sequence set forth in SEQ ID NO: 11, or the amino acid sequence set forth in SEQ ID NO: 11 in the absence of one or both epitope tags is tested in any one or more of these assays set forth in any of the examples. In certain embodiments, a chimeric polypeptide in which the internalizing moiety comprises an antibody or antigen-binding fragment comprising a light chain comprising the amino acid sequence of SEQ ID NO: 4 and comprising a heavy chain comprising the amino acid sequence of SEQ ID NO: 2 is tested. In other embodiments, a chimeric polypeptide in which the internalizing moiety comprises an antibody or antigen-binding fragment comprising a light chain comprising an amino acid sequence at least 95%, 96%, 97%, 98%, or 99% identical to SEQ ID NO: 4 and comprising a heavy chain comprising an amino acid sequence at least 95%, 96%, 97%, 98%, or 99% identical to SEQ ID NO: 2 is tested.

In Vitro PI(3)P and PI(3,5)P Phosphatase Activity of mAb3E10*hMTM1

The phosphatase activity of equimolar dilutions encompassing 5 logs of 1) chemically conjugated mAb3E10*hMTM1, 2) the unconjugated mixture of mAb 3E10 and hMTM1, 3) mAb 3E10 alone, or 4) hMTM1 alone are evaluated according to the instructions of the Malachite Green Phosphatase Assay Kit (Echelon Biosciences, Inc.) and as described by Schaletzky, J. et al. (Current Biology 13:504-509, 2003; Supplemental Data, S1-S3). Phosphatase activity is evaluated to determine whether the chemically conjugated 3E10*hMTM1 construct retains enzymatic activity. Phosphatase activity is evaluated in both a cell free system, as well as in BHK cells in culture (e.g., in BHK cells treated with the conjugates and compared to BHK cells treated with controls). Evaluating phosphatase activity in both cell free and cell-based systems is useful because assaying phosphatase activity in cells may be complicated by the fact that other proteins with PI(3)P and PI(3,5)P phosphatase activity exist (including numerous MTM1 related (MTMR) proteins having PI(3)P and PI(3,5)P phosphatase activity). Accordingly, and given that BHK cells may not provide a clean background for testing PI(3)P or PI(3,5)P phosphatase activity of these constructs, activity of the constructs will be confirmed using both cell free and cell-based systems. Activity criteria include, for example, demonstrated 50% activity of MTM1 alone (by weight) or demonstrated 50% activity of published levels (see, e.g., FIG. S1 in Supplemental Data by Schaletzky, J. et al.).

Although the present examples specifically use PIP3 (also known as "PI(3)P") and PI(3,5)P as MTM1 substrates, one of skill would readily understand that other phosphoinositide substrates as disclosed herein may also be used as a substrate for in vitro assays.

Cell Entry of mAb3E10*hMTM1 and Association with Endosomal Protein Vps34

1. BHK cells are transfected with the cDNA encoding hVps34 and/or the cDNA for the ENT2 transporter that mediates cell uptake of mAb 3E10 (Hansen J E et al., J Biol Chem. 2007 July 20; 282(29):20790-3). Two days later (48 hours post transfection) chemically conjugated mAb3E10*hMTM1 or a mixture of unconjugated mAb 3E10 and hMTM1 are applied to transfected cells, followed by immunoprecipitations with anti-Vps34, anti-hMTM1, or anti-mAb3E10, followed by immunoblot detection of mAb 3E10, hVps34, and hMTM1. Reverse immunoprecipitations are performed as controls. BHK cells are immunologically negative for human MTM1 (hMTM1), human Vps34 (hVps34) (Cao C et al., Traffic 2007; 8: 1052-1067). Cell entry of mAb3E10*hMTM1 via the transfected ENT2 transporter will be verified by treating transfected cells with an ENT2 inhibitor (NBMPR) prior to addition of conjugated and unconjugated material.

Human MTM1 is known to immunoprecipitate hVps34 and hVps15 (Cao C et al., Traffic 2007; 8: 1052-1067), and immunoprecipitation of hVps15 may be used as further validation of an endosomal association or as an alternative to hVps34 for use in immunoprecipitations. Given that BHK cells are immunologically negative for hMTM1 and hVps34, any evidence of co-immunoprecipitation of hVps34 and hMTM1, following addition of conjugated, but not unconjugated material is consistent with the conclusion that hMTM1 was delivered to cells and retained the ability to associate with hVps34.

Synthesis of human Vps34 and ENT2 cDNA: The cDNAs for hVps34 and the ENT2 transporter are as previously published (Hansen J E et al., J Biol Chem. 2007 July 20; 282(29):20790-3; Cao C et al., Traffic 2007; 8: 1052-1067). Each cDNA is cloned into a CMV-based mammalian expression cassette and large scale preps will be made using the Qiagen Mega Endo-free plasmid purification kit.

Transfections: Ten micrograms of the plasmid pCMV hVps34 and/or pCMV ENT2 are transfected into 80% confluent BHK cells using commercially available transfection reagents. Forty-eight hours after transfection chemically conjugated mAb3E10*hMTM1 or a mixture of unconjugated mAb 3E10 and free hMTM1 is applied to cells. Four to 6 hours later, the cells are washed, and treated with saponin, which clears the cytoplasmic contents while maintaining membrane structures intact (Cao C et al., Traffic 2007; 8: 1052-1067). To track the efficiency of transfection, duplicate transfections are performed with plasmids encoding a suitable reporter such as beta-galactosidase or GFP.

Immunoprecipitation and immunoblots: Immunoprecipitations are carried out as previously described (Weisbart R H et al., Mol Immunol. 2003 March; 39(13): 783-9; Cao C et al., Traffic 2007; 8: 1052-1067) with anti-hMTM1, anti-hVps34, and anti-mAb3E10 antibody, followed by immunoblot detection of coimmunoprecipitated hMTM1, hVps34, and mAb3E10. Reverse immunoprecipitations are also performed as controls. When epitope tagging is not be employed, the presence of a coincident anti-3E10 and anti-hMTM1 immunoreactive band of ~190 kDa in mAb3E10*hMTM1 treated cells versus 3E10-alone and hMTM1-alone controls will constitute successful penetration of chemically conjugated 3E10*hMTM1. If the mAb3E10*hMTM1 chemical conjugate remains intact following cell penetration it should immunoprecipitate transfected hVps34 and likewise hVps34 should immunoprecipitate hMTM1 and 3E10. Tubulin detection is used as a loading control.

ENT2 inhibition: To verify the specificity of mAb3E10*MTM1 for the ENT2 transporter all groups will be treated with the ENT2 inhibitor nitrobenzylmercaptopurine riboside (NBMPR) for 1 hour before addition of chemically conjugated mAb3E10*hMTM1 or a mixture of free recombinant mAb 3E10 and free hMTM1, and 4 to 6 hours later the media and cells will be collected for immunoprecipitations as described above.

2. Primary muscle cells are dissociated in parallel from Mtm1δ4 (and/or from other MTM1 deficient mice) and wildtype littermate mice following established method. Briefly, skeletal muscles are harvested, finely minced, and digested using dispase II and collagenase D. Primary myogenic cells are cultured in growth medium (GM: F10 20% FBS, 10 ng/ml 3/4-FGF, 1% pen/strep) on collagen-coated plates and passaged when they reach approximately 70% confluency.

Cells are treated with recombinant Fv3E10-MTM1 at a range of doses and fixed for immunodetection, or cell lysates are collected at a timecourse of endpoints. When present, the myc or 6His-tags of the recombinant Fv3E10-MTM1 protein, such as the protein set forth in SEQ ID NO: 11, is utilized for immunodetection and subsequent determination of intracellular uptake and internal localization. Anti Fv3E10-MTM1 tag antibodies are also utilized to coimmunoprecipitate intracellular Fv3E10-MTM1, to detect the presence of binding proteins, and to test the enzymatic activity (using the Malachite Green Phosphatase Assay Kit described herein) of internally transported Fv3E10-MTM1 protein.

Correction of Fusion Deficit in Primary Muscle Cells

Primary muscle cells are dissociated in parallel from Mtm1δ4 (and/or from other MTM1 deficiency mouse), and wildtype littermate mice following established method. Briefly, skeletal muscles are harvested, finely minced, and digested using dispase II and collagenase D. Primary myogenic cells are cultured in growth medium (GM: F10 20% FBS, 10 ng/ml 3/4-FGF, 1% pen/strep) on collagen-coated plates and passaged when they reach approximately 70% confluency. To assess for differences in cellular proliferation, the same number of primary cells are plated for Mtm1δ4 (and/or from other MTM1 deficient mice) and wild-type myoblasts. Cultures are followed daily for approximately 2 weeks, with or without recombinant MTM1 or Fv3E10-MTM1 addition.

To determine whether treatment with recombinant protein improves the 'fusion' deficiency of myotubularin deficient myoblasts, primary cells are plated in a 12-well plate at a concentration of $2\times10^5$ cells/well. Cells are maintained in differentiation medium consisting of DMEM supplemented 2% horse serum for 7 days, with the medium changed daily. Formation of myotubes is monitored and documented by acquiring microscopic images daily. The fusion index in control and myotubularin-deficient cultures of cells is calculated as the ratio of fused nuclei within myotubes over the number of total nuclei. Fusion indices are compared in control, mutant, and treated cultures using a Wilcoxon rank sum test. These assessments indicate whether treated cells differ in content, proliferation and differentiation abilities.

Following testing or treatment, cultured FDB myofibers or differentiated myotubes are grown on chamber slides, fixed in methanol, blocked in 10% FBS/0.1% Triton X-100, and incubated with either mouse monoclonal antibodies against desmin or myosin heavy chain type 1, type 2a, or type 2b, as described above. Positive fibers are counted and point-to-point measurements of minferet diameter are made using a Nikon Eclipse 90i microscope using NIS-Elements-AR software (Nikon, Melville, N.Y.).

Example 2

Genetic Construct of fv 3E10 and hMTM1 (Fv3E10-GS3-hMTM1 and Fv3E10-GSTS-hMTM1)

Mammalian expression vectors encoding a genetic fusion of Fv3E10 and hMTM1 (fv3E10-GS3-hMTM1, comprising the scFv of mAb 3E10 fused to hMTM1 by the GS3 linker—SEQ ID NO: 3; fv3E10-GSTS-hMTM1, comprising the scFv of mAb 3E10 fused to hMTM1 by the "GSTS" linker—SEQ ID NO: 10) are generated. An exemplary sequence for a fv3E10-GSTS-hMTM1 chimeric polypeptide is provided in SEQ ID NO: 11. Thus, chimeric polypeptides of the invention include a chimeric polypeptide comprising the amino acid sequence set forth in SEQ ID NO: 11, in the presence or absence of the epitope tags (e.g., SEQ ID NO: 11 contains a myc-tag internally and a 6×-His tag at the C terminus).

Following transfection, the cells are immunoprecipitated to verify that the genetic fusion retains the ability to associate with endosomal proteins, as described in Example 1. The conditioned media is also immunoblotted to detect secretion of 3E10 and hMTM1 into the culture media. Following concentration of the conditioned media, phosphatase activity against, e.g., PI(3)P or PI(3,5)P, is measured and the concentrated material is applied to BHK cells expressing Vps34 and ENT2 to further validate that the secreted hMTM1 fusion enters cells and retains the ability to associate with endosomal proteins. Note that these genetic fusions are also referred to as recombinant conjugates or recombinantly produced conjugates.

Additional recombinantly produced conjugates will similarly be made for later testing. By way of non-limiting example: (a) hMTM1-GS3-3E10, (b) 3E10-GS3-hMTM1, (c) hMTM1-GS3-Fv3E10, (d) hMTM1-3E10, (e) 3E10-hMTM1, (I) hMTM1-Fv3E10. Note that throughout the example, the abbreviation Fv is used to refer to a single chain Fv of 3E10. Similarly, mAb 3E10 and 3E10 are used interchangeably. These and other chimeric polypeptides can be tested using, for example, the assays detailed herein.

Synthesis of cDNA for hMTM1 and Fv3E10: The cDNA for human MTM1 (accession number: NP 000243.1) and the cDNA for the mouse Fv3E10 variable light chain linked to the 3E10 heavy chain along with flanking restriction sites that facilitate cloning into appropriate expression vectors are synthesized and sequenced. To maximize expression, each cDNA will be codon optimized for mammalian, *pichia*, and/or *E. coli* expression. The human MTM1 cDNA has three glycosylation consensus sequences that may become modified upon secretion. The cDNA encoding an exemplary mouse Fv3E10 variable light chain linked to the 3E10 heavy chain for use herein contains a mutation that enhances the cell penetrating capacity of the Fv fragment, which occurs at position 31 (D31Q) of the full mouse 3E10 sequence (Zack D J et al., J Immunol. 1996 September 1; 157(5):2082-8), and it is the variant used in the examples. The resulting cDNAs will be cloned into a mammalian expression cassette, or other appropriate expression cassette, and large scale preps of the plasmid pCMV-Fv3E10-GS3-hMTM1 will be made using the Qiagen Mega Endo-free plasmid purification kit. Exemplary sequences of mouse 3E10 VH and mouse 3E10 VL are depicted by SEQ ID NOs: 2 and 4, respectively.

Transfections: Ten micrograms of the plasmid pCMV-hMTM1, pCMV-Fv3E10-GS3-hMTM1, pCMV ENT2 or pCMV are transfected into 80% confluent BHK cells using commercially available transfection reagents. Forty-eight hours after transfection, the conditioned media is collected and concentrated, and the cells are washed and treated with saponin as described in Example 1. To track the efficiency of transfection duplicate transfections are performed with plasmids encoding a suitable reporter such as beta-galactosidase or GFP.

PIP3 phosphatase activity of genetically conjugated hMTM1 fusions: Cell lysates and concentrated conditioned media from BHK cells transfected with pCMV-hMTM1, pCMV-hMTM1 fusion as described herein or pCMV are collected and phosphatase activity, e.g., against PI(3)P or PI(3,5)P from each transfection is evaluated per the instructions of the Malachite Green Phosphatase Assay Kit (Echelon Biosciences, Inc). The general overview of experimental groups and expected results for certain control groups are indicated in Table 1. The cells marked as "?" indicate results to be obtained. Control groups 13-16 (see Table 1) will include application of chemically conjugated mAb3E10*MTM1 to pCMV (mock) transfected cells followed one day later by assessment of phosphatase activity in cell lysates and concentrated conditioned media. The following day (24 hours later) phosphatase activity is examined in cell lysates and concentrated conditioned media. For example, it is expected that phosphatase activity will not be observed in the lysate of group 13 that have been pre-treated with ENT2 inhibitor (Group 13 in Table 1). Additional control groups 17-18 will have a known activity of chemically conjugated mAb3E10*MTM1 spiked into cell lysates and concentrated conditioned media of pCMV (mock) transfected cells and will serve as a positive control and standard curve for phosphatase activity.

TABLE 1

Experimental design to evaluate PIP3 phosphatase activity, endosomal association and secretion of Fv3E10-GS3-MTM1

Table 1: Strategy to evaluate PIP3 phosphatase, endosomal association and secretion of genetically conjugated Fv3E10-GS3-MTM1

| Group | Transfected cDNAs | Immunoprecipitation antibody | Is following protein also immunoprecipitated? Vps34 | hMTM1 | 3E10 | PIP3 activity in immunoprecipitations? Lysate* | Conditioned media |
|---|---|---|---|---|---|---|---|
| 1 | pCMV hMTM1 + | anti-hMTM1 | Yes | Yes | No | Yes | No |
| 2 | CMV hVps34 | anti-hVps34 | Yes | Yes | No | Yes | No |
| 3 | | anti-3E10 | No | No | No | Yes | No |
| 4 | pCMV hMTM1 + | anti-hMTM1 | No | Yes | No | Yes | No |
| 5 | CMV | anti-hVps34 | No | No | No | Yes | No |
| 6 | | anti-3E10 | No | No | No | Yes | No |
| 7 | pCMV 3E10- | anti-hMTM1 | ? | Yes | Yes | ? | ? |
| 8 | GS3-hMTM1 + | anti-hVps34 | Yes | ? | ? | ? | ? |
| 9 | CMV hVps34 | anti-3E10 | ? | Yes | Yes | ? | ? |
| 10 | pCMV 3E10- | anti-hMTM1 | No | Yes | Yes | ? | ? |
| 11 | GS3-hMTM1 + | anti-hVps34 | No | No | No | ? | ? |
| 12 | CMV | anti-3E10 | No | Yes | Yes | ? | ? |

| Group | Transfected cDNAs | ENT2 Inhibitor | Applications of mAb3E10*hMTM1 to cells | PIP3 activity in immunoprecipitations? Lysate* | Conditioned media |
|---|---|---|---|---|---|
| 13 | CMV + CMV | + | + | No | Yes |
| 14 | ENT2 | − | + | Yes | Yes |
| 15 | CMV | + | + | ? | Yes |
| 16 | | − | + | ? | Yes |
| 17 | CMV | − | − | Yes, Spiked | No |
| 18 | | − | − | No | Yes, Spiked |

*PIP3 phosphatase activities will be a function of endogenous and hMTM1 dependent activity. Groups 13 through 16 are controls to shown that ENT2 controls the cell uptake of chemical conjugates of 3E10*hMTM1, and Groups 17 and 18 are controls for detection of MTM1 phosphatase activity in cell lysates and conditioned media Cellular uptake of genetically conjugated hMTM1 fusions: Chemically conjugated mAb3E10*hMTM1 and concentrated conditioned media from BHK cells transfected with pCMV hMTM1 fusion or pCMV is applied to BHK cells transfected 48 hours earlier with pCMV ENT2 or pCMV Table 2. Immunoprecipitations will then proceed as in Example 1. Treatment of duplicate groups with the NBMPR transporter inhibitor will verify that uptake of 3E10 is specific to the ENT2 transporter.

TABLE 2

Experimental design to evaluate if Fv3E10-GS3-hMTM1 enters cells via ENT2 and associates with endosomal proteins
Table 2: Strategy to assess if genetically conjugated Fv3E10-G53-hMTM1 enters cells via ENT2 and associates with endosomal proteins

| | cDNAs | Source of | IP | Cells treated with SALINE before recombinant protein Is following protein also immunoprecipitated? | | | Cells treated with NBMPR before recombinant protein Is following protein also immunoprecipitated? | | |
|---|---|---|---|---|---|---|---|---|---|
| Group | Transfected | 3E10-hMTM1 | Antibody | Vps34 | hMTM1 | 3E10 | Vps34 | hMTM1 | 3E10 |
| 1 | pCMV | 3E10 + hMTM1 | anti-hMTM1 | No | No | No | No | No | No |
| 2 | hVps34 + | mixed | anti-hVps34 | Yes | No | No | Yes | No | No |
| 3 | pCMV ENT2 | unconjugated | anti-3E10 | No | No | Yes | No | No | No |
| 4 | pCMV | | anti-hMTM1 | No | No | No | No | No | No |
| 5 | hVps34 + | | anti-hVps34 | Yes | No | No | Yes | No | No |
| 6 | pCMV | | anti-3E10 | No | No | ? | No | No | No |
| 7 | pCMV + | | anti-hMTM1 | No | No | No | No | No | No |
| 8 | pCMV | | anti-hVps34 | No | No | No | No | No | No |
| 9 | ENT2 | | anti-3E10 | No | No | Yes | No | No | No |
| 10 | pCMV | mAb 3E10* | anti-hMTM1 | Yes* | Yes | Yes | No | No | No |
| 11 | hVps34 + | hMTM1 | anti-hVps34 | Yes | Yes* | Yes* | Yes | No | No |
| 12 | pCMV ENT2 | (chemically conjugated) | anti-3E10 | Yes* | Yes | Yes | No | No | No |
| 13 | pCMV | | anti-hMTM1 | Yes* | Yes | Yes | No | No | No |
| 14 | hVps34 + | | anti-hVps34 | Yes | Yes* | Yes* | Yes | No | No |
| 15 | pCMV | | anti-3E10 | Yes* | Yes | Yes | No | No | No |
| 16 | pCMV + | | anti-hMTM1 | No | Yes | Yes | No | No | No |
| 17 | pCMV | | anti-hVps34 | No | No | No | No | No | No |
| 18 | ENT2 | | anti-3E10 | No | Yes | Yes | No | No | No |
| 19 | pCMV | Concentrated | anti-hMTM1 | ? | ? | ? | No | No | No |
| 20 | hVps34 + | conditioned | anti-hVps34 | Yes | ? | ? | Yes | No | No |
| 21 | pCMV ENT2 | media from pCMV | anti-3E10 | ? | ? | ? | No | No | No |
| 22 | pCMV | Fv3E10-GS3- | anti-hMTM1 | ? | ? | ? | No | No | No |
| 23 | hVps34 + | hMTM1 | anti-hVps34 | Yes | ? | ? | Yes | No | No |
| 24 | pCMV | transfection | anti-3E10 | ? | ? | ? | No | No | No |
| 25 | pCMV + | (genetically | anti-hMTM1 | No | ? | ? | No | No | No |
| 26 | pCMV | conjugated) | anti-hVps34 | No | No | No | No | No | No |
| 27 | ENT2 | | anti-3E10 | No | ? | ? | No | No | No |
| 28 | pCMV | Concentrated | anti-hMTM1 | Yes** | Yes | Yes | Yes** | Yes | Yes |
| 29 | Vps34 + | conditioned | anti-hVps34 | Yes | Yes** | Yes** | Yes | Yes** | Yes** |
| 30 | pCMV 3E10-GS3-hMTM1 | media from pCMV mock transfection | anti-3E10 | Yes** | Yes | Yes | Yes** | Yes | Yes |

*immunoprecipitated and detected by immunoblot only if immunoprecipitated in specific aim 1 table 2 groups 10 through 18.
**assumes the genetic conjugate has no defects in association between Vps34 and hMTM1.

Example 3

Recombinant Production of hMTM1 Fusions and Verification of PIP3 Phosphatase Activity, Cell Penetration, and Endosomal Association with Vps34

Recombinant 3E10-GS3-hMTM1 or 3E10-GSTS-hMTM1 is produced using the *Pichia* yeast protein expression system (Invitrogen, RCT). *Pichia* exhibits excellent protein expression, high cell densities, controllable processes, generation stability, durability and product processing that is similar to mammalian cells. Both secreted and nonsecreted forms of 3E10-GS3-hMTM1 are produced. The hMTM1 sequence contains three potential NXS/T glycosylation sites that may affect the biological activity of any secreted material. In other embodiments, the chimeric polypeptides are produced in a bacterial expression system (e.g., *E. coli*) or a mammalian cell expression system.

Construction of protein expression vectors for *Pichia*: Plasmid construction, transfection, colony selection and culture of *Pichia* will use kits and manuals per the manufacturer's instructions (Invitrogen). The cDNAs for genetically conjugated hMTM1 (3E10-GS3-hMTM1 or 3E10-GSTS-hMTM1) created and validated in Example 2 are cloned into two alternative plasmids; PICZ for intracellular expression and PICZalpha for secreted expression. Protein expression from each plasmid is driven by the AOX1 promoter. Transfected *Pichia* are selected with Zeocin and colonies are tested for expression of recombinant hMTM1 fusion. High expressers will be selected and scaled for purification.

Purification of recombinant hMTM1 fusion: cDNA fusions with mAb 3E10 Fv are ligated into the yeast expression vector pPICZA which is subsequently electroporated into the *Pichia pastoris* X-33 strain. Colonies are selected with Zeocin (Invitrogen, Carlsbad, Calif.) and identified with anti-his6 antibodies (Qiagen Inc, Valencia, Calif.). X-33 cells are grown in baffled shaker flasks with buffered glycerol/methanol medium, and protein synthesis is induced with 0.5% methanol according to the manufacturer's protocol (EasySelect *Pichia* Expression Kit, Invitrogen, Carlsbad, Calif.). The cells are lysed by two passages through a French Cell Press at 20,000 lbs/in2, and recombinant protein is purified from cell pellets solubilized in 9M guanidine HCl and 2% NP40 by immobilized metal ion affinity chromatography (IMAC) on Ni-NTA-Agarose (Qiagen, Valencia, Calif.). Bound protein is eluted in 50 mM NaH2PO4 containing 300 mM NaCl, 500 mM imidazole, and 25% glycerol. Samples of eluted fractions are electrophoresed in 4-20% gradient SDS-PAGE (NuSep Ltd, Frenchs Forest, Australia), and recombinant proteins is identified by Western blotting to nitrocellulose membranes developed with cargo-specific mouse antibodies followed by alkaline-phosphatase-conjugated goat antibodies to mouse IgG. Alkaline phosphatase activity is measured by the chromogenic substrate, nitroblue tetrazolium chloride/5-bromo-4-chloro-3-indolylphosphate p-toluidine salt. Proteins are identified in SDS-PAGE gels with GelCode Blue Stain Reagent (Pierce Chemical Co., Rockford, Ill.). Eluted protein is concentrated, reconstituted with fetal calf serum to 5%, and exchange dialyzed 100-fold in 30,000 MWCO spin filters (Millipore Corp., Billerica, Mass.) against McCoy's medium (Mediatech, Inc., Herndon, Va.) containing 5% glycerol.

Expression is bacteria: Chimeric polypeptide may also be expressed in a bacterial expression system, such as *E. coli*. In such cases, nucleic acid construct encoding the chimeric polypeptide is codon biased optimized for expression in *E. coli*. For expression in *E. coli*, pGEX-2T GST expression vector is used. Different strains of *E. coli* may be tested to optimize expression, such as *E. coli* strains WGA, BL21(DE3), and BL21(DE3) pLysE.

Quality assessment and formulation: Immunoblot against 3E10 and hMTM1 will be used to verify the size and identity of recombinant proteins, followed by silver staining to identify the relative purity of among preparations of 3E10, MTM1 and hMTM1 fusion. Recombinant material will be formulated in a buffer and concentration (~0.5 mg/ml) that is consistent with the needs of subsequent in vivo administrations.

In vitro assessment of recombinant material: Based on studies from Example 2, the amount of phosphatase activity (e.g., against PI(3)P or PI(3,5)P per mole of conjugate that exists in the conditioned media of hMTM1 fusion transfected cells is determined and this value is used as a standard for assessment of phosphatase activity of *pichia* or *E. coli*-derived recombinant hMTM1 fusion. As shown in Table 2, the relative PIP3 phosphatase activity of chemically conjugated, mammalian cell-derived and *pichia*-derived recombinant 3E10-GS3-hMTM1 on Vps34 transfected BHK cells is similarly compared.

Example 4

In Vivo Assessment of Muscle Targeted hMTM1 in MTM KO Mice

Selection of a Mouse Model for Evaluation

Mice possessing a targeted inactivation of the MTM1 gene (MTM1 KO) are born at a submendellian distribution but otherwise appear normal. However, within the first weeks of life MTM1 KO mice begin to lose muscle mass that rapidly progresses to respiratory collapse and death at a median age of 7 weeks (14 weeks maximum) (Bello A B et al., *Proc Natl Acad Sci USA*. 2002 November 12; 99(23): 15060-5). The progressive decline in MTM KO mice coincides with blunted weight gain, reduced forelimb grip strength, reduced ability to support themselves against the force of gravity and increased foot dragging (Bello A B et al., *Proc Natl Acad Sci USA*. 2002 November 12; 99(23): 15060-5). Myofibers of MTM KO mice appear hypotrophic and vacuolated with centrally located nuclei surrounded by mitochondria and glycogen, yet there is very little sarcolemma damage and no evidence of apoptosis or inflammation (Bello A B et al., *Proc Natl Acad Sci USA*. 2002 November 12; 99(23):15060-5). An advantage of using MTM1 KO mice is the ability to use ELISA to track the serum and tissue levels 3E10-GS3-MTM1, and will be necessary for the subsequent pharmacokinetic assessments and the respective pharmacodynamic and toxicologic responses. To control whether a superphysiological level of MTM1 is detrimental, 3E10-hMTM1 will be administered to wildtype MTM1 homozygous mice (+/+).

Exemplary assays for assessing treated mice are described below. In addition, improvement in the condition of mice is assessed based on life expectancy (increase in life expectancy in treated mice), weight, and decrease in foot dragging.

Selection of Dose of 3E10-GS3-hMTM1

The evaluation dose of 3E10 chemically or genetically conjugated to hMTM1 delivered to MTM KO mice is determined. As a starting point, to demonstrate a therapeutic response, a high dose (e.g., 5.0 mg/kg) is administered intravenously twice per week for as long as 20 weeks or death, whichever comes first. A dose of 5 mg/kg of 3E10-GS3-MTM1 is delivered twice per week to MTM KO mice for 20 weeks (Table 3), followed by assessment of changes in disease endpoints. Controls include vehicle and treated heterozygous MTM1 +/+ mice and vehicle treated MTM1 −/− mice. Development of anti-3E10-MTM1 antibodies is also monitored. If we establish that intravenous 3E10*MTM1 or MTM1 genetic fusions (e.g., 3E10-GS3-hMTM1 or 3E10-GSTS-hMTM1) results in an improvement in phenotype, subsequent in vivo PK assessments in MTM KO mice will be initiated to identify a dosing regimen that promotes the greatest pharmacodynamic effect with the least toxicologic consequences.

TABLE 3

In vivo dosing plan for chemically and genetically conjugated 3E10-MTM1

Table 3: In vivo dosing plan for chemically and genetically conjugated 3E10-MTM1

| Group | Strain | Age (weeks) | # of mice | Treatment | Dose (mg/kg) |
|---|---|---|---|---|---|
| 1 | MTM1−/− | 10 | 5 | mAb 3E10*hMTM1 (chemically conjugated) | 5 |

TABLE 3-continued

In vivo dosing plan for chemically and genetically conjugated 3E10-MTM1
Table 3: In vivo dosing plan for chemically and genetically conjugated 3E10-MTM1

| Group | Strain | Age (weeks) | # of mice | Treatment | Dose (mg/kg) |
|---|---|---|---|---|---|
| 2 | MTM1−/− | 10 | 5 | mAb 3E10 & hMTM1 (mixed unconjugated) | 5 |
| 3 | MTM1−/− | 10 | 5 | Fv3E10-GS3-hMTM1 (genetically conjugated) | 5 |
| 4 | MTM1−/− | 10 | 5 | Vehicle | NA |
| 5 | MTM1+/+ | 10 | 5 | mAb 3E10*hMTM1 (chemically conjugated) | 5 |
| 6 | MTM1+/+ | 10 | 5 | mAb 3E10 & hMTM1 (mixed unconjugated) | 5 |
| 7 | MTM1+/+ | 10 | 5 | Fv3E10-GS3-hMTM1 (genetically conjugated) | 5 |
| 8 | MTM1+/+ | 10 | 5 | Vehicle | NA |

Timepoint Information: Dose twice per week for 20 weeks. Daily observations. Collect blood and tissues for IHC, H&E and protein isolation Grip strength: The grip strength device (Columbus Instruments) requires no training on behalf of the mouse. The whole body tension test employed by others (Bello A B et al., *Proc Natl Acad Sci USA*. 2002 November 12; 99(23):15060-5) an animal tied by its tail to a force transducer, the tail is then pinched, and the tension exerted as the animal attempts to escape is measured. Aside from the animal welfare implications of inducing pain as a condition of a response, it is unclear how the pinch force is standardized or how the tail is properly secured to the transducer. As an acceptable alternative, a forelimb grip strength test, normalized to mouse weight, would sufficiently replicate the measurements of the whole body tension test, would survive the scrutiny of an IACUC and can be performed with a readily available force transducer (Columbus Instruments). The angle at which the mouse is pulled from the metal grid will have a proportional effect on the force measurement. Therefore, the grip strength test is standardized by pulling the mouse by the tail parallel to the horizontal grid and away from the force transducer at a rate of about 5 cm/second. Four pulls separated by ~20 seconds of rest are used to gauge any fatigue.

Injection of chemically and genetically conjugated 3E10-MTM1. 3E10*hMTM1 or hMTM1 genetic fusion is formulated and diluted in a buffer that is consistent with intravenous injection (e.g. sterile saline solution or a buffered solution of 50 mM Tris-HCl, pH 7.4, 0.15 M NaCl). The amount of 3E10*hMTM1 or hMTM1 genetic fusion given to each mouse is calculated as follows: dose (mg/kg)×mouse weight (kg)×stock concentration (mg/ml)=volume (ml) of stock per mouse, q.s. to 100 ul with vehicle.

Blood collection. Blood is collected by cardiac puncture at the time that animals are sacrificed for tissue dissection. Serum is removed and frozen at −80° C. To minimize the effects of thawing and handling all analysis of 3E10*MTM1 or MTM1 genetic fusion circulating in the blood is performed on the same day.

Tissue collection and preparation. Sampled tissues are divided for immunoblot, formalin-fixed paraffin-embedded tissue blocks and frozen sections in OCT. One half of the heart, liver, lung, spleen, kidneys, quadriceps, EDL, soleus, diaphragm, and biceps will be subdivided and frozen in plastic tubes for further processing for immunoblot analysis. The remaining half of the heart, liver, lung, spleen, kidneys, quadriceps, EDL, soleus, diaphragm, and biceps will be subdivided, frozen in OCT tissue sectioning medium, or fixed in zinc-formaldehyde fixation for 24 to 48 hours at 4° C. and paraffin embedded.

Histological evaluation. Brightfield microscopy of HE sections are used to determine the percentage of centrally nucleated myofibers and myofiber cross-sectional area from five randomly selected fields. At least 200 fibers are counted per mouse per muscle group. Other sections are stained for NADH-TR. Scoring of blinded sections for central nuclei, myofiber cross-sectional area, and normalization of NADH-TR staining is also performed.

Immunoblot. Protein isolation and immunoblot detection of 3E10 and MTM1 is performed as previously described (Weisbart R H et al., Mol Immunol. 2003 March; 39(13):783-9; Bello A B et al., Human Molecular Genetics, 2008, Vol. 17, No. 14; Lorenzo O et al., Journal of Cell Science 119, 2953-2959 2005).

Analysis of circulating 3E10-hMTM1: An ELISA specific to human 3E10-MTM1 is developed and validated using commercially available anti-human MTM1 antibodies. Recombinant 3E10-MTM1 is diluted and used to generate a standard curve. Levels of 3E10-MTM1 are determined from dilutions of serum (normalized to ng/ml of serum) or tissue extracts (normalized to ng/mg of tissue).

Monitoring of anti-3E10-hMTM1 antibody responses. Purified 3E10-MTM1 used to inject MTM KO mice is plated onto high-binding 96 well ELISA plates at 1 ug/ml in coating buffer (Pierce Biotech), allowed to coat overnight, blocked for 30 minutes in 1% nonfat drymilk (Biorad) in TBS, and rinsed three times in TBS. Two-fold dilutions of sera from vehicle and 3E10-MTM1 injected animals are loaded into wells, allowed to incubate for 30 minutes at 37° C., washed three times, incubated with horseradish peroxidase (HRP)-conjugated rabbit anti-mouse IgA, IgG, and IgM, allowed to incubate for 30 minutes at 37° C., and washed three times. Mouse anti-3E10-MTM1 antibodies are detected with TMB liquid substrate and read at 405 nm in ELISA plate reader. Polyclonal rabbit anti-mouse MTM1 (Bello A B et al., Human Molecular Genetics, 2008, Vol. 17, No. 14), followed by HRP-conjugated goat anti-rabbit serves as the positive control antibody reaction. Any absorbance at 405 nm greater than that of vehicle treated MTM1 KO mice constitutes a positive anti-3E10-MTM1 antibody response.

Statistical Analysis. Pairwise comparisons will employ Student's t-test. Comparisons among multiple groups will employ ANOVA. In both cases a p-value <0.05 will be considered statistically significant.

The foregoing examples help illustrate the experiments that can be used during the making and testing of chimeric polypeptides for use in the methods described herein. Chimeric polypeptides comprising an MTM1 portion and an internalizing moiety are tested using, for example, these methods. Any of the chimeric polypeptides described in the specification can be readily tested. Any chimeric polypeptide comprising an MTM1 portion and an internalizing moiety can be similarly tested to confirm that the chimeric polypeptide maintains the activity of MTM1 and the cell penetrating activity of the internalizing moiety. Reference to any particular chimeric polypeptide in these examples is merely for example. In certain embodiments, a chimeric polypeptide comprising the amino acid sequence set forth in SEQ ID NO: 11, or the amino acid sequence set forth in SEQ ID NO: 11 in the absence of one or both epitope tags is tested in any one or more of the assays set forth in any of the examples. In certain embodiments, a chimeric polypeptide in which the internalizing moiety comprises an antibody or antigen-binding fragment comprising a light chain comprising the amino acid sequence of SEQ ID NO: 4 and comprising a heavy chain comprising the amino acid sequence of SEQ ID NO: 2 is tested. In other embodiments, a chimeric polypeptide in which the internalizing moiety comprises an antibody or antigen-binding fragment comprising a light chain comprising an amino acid sequence at least 95%, 96%, 97%, 98%, or 99% identical to SEQ ID NO: 4 and comprising a heavy chain comprising an amino acid sequence at least 95%, 96%, 97%, 98%, or 99% identical to SEQ ID NO: 2 is tested.

SEQUENCE INFORMATION

```
amino acid sequence of the human MTM1 protein (NP_000243.1)
                                                        SEQ ID NO: 1
MASASTSKYNSHSLENESIKRTSRDGVNRDLTEAVPRLPGETLITDKEVIYICPFNGPIKGRVYI

TNYRLYLRSLETDSSLILDVPLGVISRIEKMGGATSRGENSYGLDITCKDMRNLRFALKQEGHSR

RDMFEILTRYAFPLAHSLPLFAFLNEEKFNVDGWTVYNPVEEYRRQGLPNHHWRITFINKCYELC

DTYPALLVVPYRASDDDLRRVATFRSRNRIPVLSWIHPENKTVIVRCSQPLVGMSGKRNKDDEKY

LDVIRETNKQISKLTIYDARPSVNAVANKATGGGYESDDAYHNAELFFLDIHNIHVMRESLKKVK

DIVYPNVEESHWLSSLESTHWLEHIKLVLTGAIQVADKVSSGKSSVLVHCSDGWDRTAQLTSLAM

LMLDSFYRSIEGFEILVQKKWISFGHKFASRIGHGDKNHTDADRSPIFLQFIDCVWQMSKQFPTA

FEFNEQFLIIILDHLYSCRFGTFLFNCESARERQKVTERTVSLWSLINSNKEKFKNPFYTKEINR

VLYPVASMRHLELWVNYYIRWNPRIKQQQPNPVEQRYMELLALRDEYIKRLEELQLANSAKLSDP

PTSPSSPSQMMPHVQTHF

3E10 Variable heavy chain
                                                        SEQ ID NO: 2
EVQLVESGGGLVKPGGSRKLSCAASGFTFSNYGMHWVRQAPEKGLEWVAYISSGSSTIYYADTVK

GRFTISRDNAKNTLFLQMTSLRSEDTAMYYCARRGLLLDYWGQGTTLTVSS

linker sequence "GS3"
                                                        SEQ ID NO: 3
GGGGSGGGGSGGGGS

3E10 Variable light chain
                                                        SEQ ID NO: 4
DIVLTQSPASLAVSLGQRATISCRASKSVSTSSYSYMHWYQQKPGQPPKLLIKYASY

LESGVPARFSGSGSGTDFHLNIHPVEEEDAATYYCQHSREFPWTFGGGTKLELK

human MTM1 nucleic acid sequence (NM_0002522)
                                                        SEQ ID NO: 5
agagggggcg gagcagggcc cggcagccga gcagcctggc aacggcggtg gcgcccggag

cccgagagtt tccaggatgg cttctgcatc aacttctaaa tataattcac actccttgga

gaatgagtct attaagagga cgtctcgaga tggagtcaat cgagatctca ctgaggctgt

tcctcgactt ccaggagaaa cactaatcac tgacaaagaa gttatttaca tatgtccttt

caatggcccc attaagggaa gagtttacat cacaaattat cgtctttatt taagaagttt

ggaaacggat tcttctctaa tacttgatgt tcctctgggt gtgatctcga gaattgaaaa

aatgggaggc gcgacaagta gaggagaaaa ttcctatggt ctagatatta cttgtaaaga

catgagaaac ctgaggttcg ctttgaaaca ggaaggccac agcagaagag atatgtttga

gatcctcacg agatacgcgt ttcccctggc tcacagtctg ccattatttg catttttaaa

tgaagaaaag tttaacgtgg atggatggac agtttacaat ccagtggaag aatacaggag

gcagggcttg cccaatcacc attggagaat aacttttatt aataagtgct atgagctctg

tgacacttac cctgctcttt tggtggttcc gtatcgtgcc tcagatgatg acctccggag

agttgcaact tttaggtccc gaaatcgaat tccagtgctg tcatggattc atccagaaaa

taagacggtc attgtgcgtt gcagtcagcc tcttgtcggt atgagtggga aacgaaataa
```

-continued

```
agatgatgag aaatatctcg atgttatcag ggagactaat aaacaaattt ctaaactcac
catttatgat gcaagaccca gcgtaaatgc agtggccaac aaggcaacag gaggaggata
tgaaagtgat gatgcatatc ataacgccga acttttcttc ttagacattc ataatattca
tgttatgcgg gaatctttaa aaaaagtgaa ggacattgtt tatcctaatg tagaagaatc
tcattggttg tccagtttgg agtctactca ttggttagaa catatcaagc tcgttttgac
aggagccatt caagtagcag acaaagtttc ttcagggaag agttcagtgc ttgtgcattg
cagtgacgga tgggacagga ctgctcagct gacatccttg gccatgctga tgttggatag
cttctatagg agcattgaag ggttcgaaat actggtacaa aaagaatgga taagttttgg
acataaattt gcatctcgaa taggtcatgg tgataaaaac cacaccgatg ctgaccgttc
tcctattttt ctccagttta ttgattgtgt gtggcaaatg tcaaaacagt tccctacagc
ttttgaattc aatgaacaat tttgattat aattttggat catctgtata gttgccgatt
tggtactttc ttattcaact gtgaatctgc tcgagaaaga cagaaggtta cagaaaggac
tgtttcttta tggtcactga taaacagtaa taaagaaaaa ttcaaaaacc ccttctatac
taaagaaatc aatcgagttt tatatccagt tgccagtatg cgtcacttgg aactctgggt
gaattactac attagatgga accccaggat caagcaacaa cagccgaatc cagtggagca
gcgttacatg gagctcttag ccttacgcga cgaatacata aagcggcttg aggaactgca
gctcgccaac tctgccaagc tttctgatcc cccaacttca ccttccagtc cttcgcaaat
gatgccccat gtgcaaactc acttctgagg ggggaccctg gcaccgcatt agagctcgaa
ataaaggcga tagctgactt tcatttgggg catttgtaaa aagtagatta aaatatttgc
ctccatgtag aacttgaact aacataatct taaactcttg aatatgtgcc ttctagaata
catattacaa gaaaactaca gggtccacac ggcaatcaga agaaaggagc tgagatgagg
ttttggaaaa ccctgacacc tttaaaaagc agtttttgaa agacaaaatt tagatttaat
ttacgtcttg agaaatacta tatatacaat atatattttg tgggcttaat tgaaacaaca
ttattttaaa atcaaagggg atatatgttt gtggaatgga ttttcctgaa gctgcttaac
agttgctttg gattctctaa gatgaatcca aatgtgaaag atgcatgtta ctgccaaaac
caaattgagc tcagcttcct aggcattacc caaaagcaag gtgtttaagt aattgccagc
ttttatacca tcatgagtgg tgacttaagg agaaatagct gtatagatga gtttttcatt
atttggaaat ttaggggtag aaaatgtttt cccctaattt tccagagaag cctattttta
tatttttaaa aaactgacag ggcccagtta aatatgattt gcatttttta aatttgccag
ttttattttc taaattcttt catgagcttg cctaaaattc ggaatggttt tcgggttgtg
gcaaacccca aagagagcac tgtccaagga tgtcgggagc atcctgctgc ttaggggaat
gttttcgcaa atgttgctct agtcagtcca gctcatctgc caaaatgtag ggctaccgtc
ttggatgcat gagctattgc tagagcatca tccttagaaa tcagtgcccc agatgtacat
gtgttgagcg tattcttgaa agtattgtgt ttatgcattt caatttcaat ggtgttggct
tcccctcccc accccacgcg tgcataaaaa ctggttctac aaatttttac ttgaagtacc
aggccgtttg ctttttcagg ttgttttgtt ttatagtatt aagtgaaatt ttaaatgcac
agttctattt gctatctgaa ctaattcatt tattaagtat atttgtaaaa gctaaggctc
gagttaaaac aatgaagtgt tttacaatga tttgtaaagg actatttata actaatatgg
ttttgttttc aatgaattaa gaaagattaa atatatcttt gtaaattatt ttatgtcata
gtttaattgg tctaccaagt aagacatctc aaatacagta gtataatgta tgaattttgt
aagtataaga aattttatta gacattctct tactttttgt aaatgctgta aatatttcat
```

-continued aaattaacaa agtgtcactc cataaaaaga aagctaatac taatagccta aaagattttg tgaaatttca tgaaaacttt ttaatggcaa taatgactaa agacctgctg taataaatgt attaactgaa acctaaaaaa aaaaaaaaaa aa mouse MTM1 protein sequence (NP_064310.1)

SEQ ID NO: 6

MASASASKYNSHSLENESIKKVSQDGVSQDVSETVPRLPGELLITEKEVIYICPFNGPIKGRVYI

TNYRLYLRSLETDSALILDVPLGVISRIEYMGGATSRGENSYGLDITCKDLRNLRFALKQEGHSR

RDMFEILVKHAFPLAHNLPLFAFVNEEKENVDGWTVYNPVEEYRRQGLPNHHWRISFINKCYELC

ETYPALLVVPYRTSDDDLRRIATFRSRNRLPVLSWIHPENKMVIMRCSQPLVGMSGKRNKDDEKY

LDVIRETNKQTSKLMIYDARPSVNAVANKATGGGYESDDAYQNSELSFLDIHNIHVMRESLKKVK

DIVYPNIEESHWLSSLESTHWLEHIKLVLTGAIQVADQVSSGKSSVLVHCSDGWDRTAQLTSLAM

LMLDSFYRTIEGFEILVQKEWISFGHKFASRIGHGDKNHADADRSPIFLQFIDCVWQMSKQFPTA

FEFNEGFLITVLDHLYSCRFGTFLFNCDSARERQKLTERTVSLWSLINSNKDKFKNPFYTKEINR

VLYPVASMRHLELWVNYYIRWNPRVKQQQPNPVEQRYMELLALRDDYIKRLEELQLANSAKLADA

PASTSSSSQMVPHVQTHF mouse MTM1 nucleic acid sequence (NM_019926.2)

SEQ ID NO: 7 ggtgagttcg ctttcttggc tgacctggct cggagccggg cattgcgggg atccaggatt ggaaaggttc caggatggct tctgcatcag catctaagta taattcacac tccttggaga atgaatccat taagaaagtg tctcaagatg gagtcagtca ggatgtgagt gagactgtcc ctcggctccc aggggagtta ctaattactg aaaaagaagt tatttacata tgtcctttca atggccccat taagggaaga gtttacatca caaattatcg tctttattta agaagtttgg aaacggattc tgctctaata cttgatgttc ctctgggtgt gatatcaaga attgaatata tgggaggcgc gactagtaga ggagaaaatt cctatggtct agatattact tgtaaagatt tgagaaacct gaggtttgca ttgaagcaag aaggccacag cagaagagat atgtttgaga tccttgtaaa acatgccttt cctctggcac acaatctgcc attatttgca tttgtaaatg aagagaagtt taacgtggat gggtggactg tttataatcc agttgaagaa tatagaaggc agggcctgcc caatcaccat tggaggataa gttttattaa caagtgctat gagctctgtg agacataccc tgctcttttg gtggttccct atcggacctc agatgatgat cttaggagga tcgcaacgtt tagatcccga aatcggcttc ctgtactgtc gtggattcac ccagaaaaca aaatggtcat tatgcgctgc agtcagcctc ttgtcggtat gagtggtaaa agaaataaag atgacgagaa atacctggat gtgatcaggg aaactaacaa acaaacttct aagctcatga tttatgatgc acgacccagt gtaaatgcag tcgccaacaa ggcaacagga ggaggatatg aaagtgatga cgcatatcaa aactcagaac tttccttctt agacattcat aatattcatg ttatgcgaga atctttaaaa aaagtgaaag atattgttta tcccaacata gaagaatctc attggttgtc cagtttggag tctactcatt ggttagaaca tatcaagctt gttctgaccg gtgccattca agtggcagac caagtgtctt caggaaagag ctcggtactt gtgcactgca gtgacggatg ggacaggacc gctcagctga catccttggc catgctgatg ttggacagct tctacagaac tattgaaggc tttgagatat tggtacagaa agagtggata agttttggcc ataaatttgc atctagaata ggtcatggtg ataaaaacca tgctgatgct gatcgatctc ctatttttct tcagtttatt gactgtgtgt ggcagatgtc gaaacagttc cccacagctt ttgagttcaa tgaaggcttt ttgattaccg ttttggatca tctgtatagc tgtcgatttg gtactttctt attcaactgt gactcggctc gagaaagaca gaaacttaca gaaagaacag -continued tttctctatg gtcgctaatt aacagcaata aagacaaatt caaaaacccc ttctatacaa aagaaatcaa tcgggttttg tatccagttg ccagcatgcg tcacttggaa ctgtgggtga attattacat ccgatggaat cccagggtca agcagcaaca gcccaaccca gtggagcagc gttacatgga gcttttggcc ttgcgtgacg attatataaa gaggctcgag gaattgcagc tggccaactc cgccaagctt gctgatgccc ccgcttcgac ttccagttcg tcacagatgg tgccccatgt gcagacgcac ttctgagggg actcacttct ggcactgcac ttgaactcta gataagtgaa atagctgact ctcattctgg gcatgtggac aaagtagatt taaagtgtct gcctccattt agaagttcaa ctaacatctt agacttttga gtatgtgcct tctgtaatac atatcacaag aaatcgatgg tgtccgtgtg gcaatcataa ggaaggagtc aagagggggt tctggaaaat cctcatactt ttttttacaa agcacttttg caaagataaa acttaaattt aatttacctc tatataaatt ctacatatac agtatgtatt ttgtgggctt aattgaaata ttattttaaa tccagggggg agatttgttt gcaaaatgta ttttcctcca gctgcttata acagttgctt tggattatct aaaattaatc caaatgtgaa agatgggtat tactgccaaa gccaaattgc actctgcttc ttcagcaaat tccaagagca aggcgtttaa ataattgcca atttttattt taccataagt ggtaaggtaa aaagaaagat gaacatttca tcattttgaa tttttgaaaa taaaaggttc tcccatcatt tttcaagaga agcacatttt tatattaaga aaaagtgata aggtttgatt ttttttcccc tcaacattct cagctttgct ttctaaatta tcccatgatt tttgtctaac actgagtcat actcaggttg aaggaaaccc ataaatagca ctgtgcgagg agctggctgg cttctgctgc ttagaggaat atgttcgcaa acatgcctct agtcaattcg ccttatctgc tgaagtgtag gggcaccgcc ttgaatggat gagctatggc tagagcatct ttctttacag taatgcccca ggtgtattct gtttatgtct ctctgtttaa atggtgtgcg tgcataaaaa cttgctctgc acattattac ttgaagtact gggcaatttg ctttttcagg tttttttca ttttgttttg tagtatgaaa tggaatttta aatgcacagt tctatttgat atccgaacta attcatttag taaatatatt tgtaaaagct aaagttaaat caattaatgt tttacagtga tttgtaaagg attatttata gctaatatgg ttttgttttc agtgaattaa gagagattac atttatcttt gtaaattatt ttatgtcata gcttaatggc ctaccaaatg agacatctca aatataatag tataatgtat ggattttgta agtataaaaa ttattagata ttcgtttgct ttttgtaaac actgtaaata tttcataaat taaaatgtgt cactccataa gaagaaaaaa ctaatactaa tagttgacag gaattggtga aatttcatga aaatattttc attgcaataa atattaaaag acctgctg rat MTM1 protein sequence (NP_001013065A)

SEQ ID NO: 8

MASSSASDCDAHPVERESMRKVSQDGVRQDMSKSGPRLPGESAITDKEVIYICPFSGPVKGRLYI

TNYRLYLRSLETDLAPILDVPLGVISRIEKNIGGVTSRGENSYGLDITCKDLRNLRFALKQEGHS

RRDIFDVLTRHAFPLAYNLPLEAFVNEEKFKVDGWAIYNPVEEYRRQGLPDRHWRISFVNQRYEL

CDTYPALLVVPYRASDDDLRRVATFRSRNRIPVLSWIHPENRAAIMRCSQPLVGVGGKRSRDDER

YLDIIRETNKQTSKLTIYDARPGVNAVANKATGGGYEGEDAYPHAELSFLDIHNIHVMRESLRRV

RDIVYPHVEEAHWLSSLESTHWLEHIKLLLTGAIRVADKVASGLSSVLVHCSDGWDRTAQLTTLA

MLMLDGFYRSIEGFEILVQKEWISFGHKFSSRIGHGDKNHADADRSPIFLQFIDCVWQMTKQFPT

AFEFNECFLVAILDHLYSCRFGTFLLNCEAARERQRLAERTVSVWSLINSNKDEFTNPFYARESN

RVIYPVTSVRHLELWVNYYIRWNPRIRQQQPHPM

-continued rat MTM1 nucleic acid sequence (NM_001013047A)

SEQ ID NO: 9 gcgagcgcgt tggcaccagc ggcccccgga gtctcaggtt ccaggatggc gtcctcgtca gcctctgact gtgatgcaca ccccgtggag cgtgagtcca tgaggaaggt gtctcaagat ggagtccgtc aggatatgag caagagtggg cctcgcctcc caggggaatc agccatcact gacaaggaag tcatctacat ttgtcccttc agcggccccg taaagggacg actttacatc accaattacc gtctctacct gagaagtctg gagacggact tggctccgat tcttgacgtc cccctaggcg tgatatcgag aatagagaaa atgggaggcg tgacgagtcg aggagagaat tcctacggcc ttgatatcac ctgcaaagac ctgaggaacc tgaggttcgc tctgaagcag gaaggacaca gcaggaggga catctttgac gtcctcacca gacacgcctt ccccctggct tacaacctgc cgttgtttgc attcgtgaac gaggagaagt ttaaagtgga tggatgggcg atttacaacc cggttgaaga gtacagaagg cagggcctcc ccgatcgcca ttggcggata agtttcgtca atcagcgcta cgagctctgt gacacctacc ctgccctcct ggtcgtcccc taccgtgcgt ccgatgatga cctcagaaga gttgcaacct ttaggtccag aaaccggatt cccgtgctgt cgtggatcca cccagagaac agggcggcga tcatgcggtg cagtcagcct ctggttggtg tgggcgggaa gagaagcaga gatgatgaga gatacctgga catcatccgg gaaaccaata agcagacctc gaagctcaca atttacgatg cgcggcccgg cgtcaatgcg gtggccaaca aggcaacggg aggcggctat gagggcgagg acgcgtaccc tcacgcggag ctctccttcc tggacatcca caacatccac gtgatgcggg aatccttacg gagggtgagg gacatcgtgt acccccacgt ggaggaagct cattggctgt ccagcttgga gtccacccat tggttagagc acatcaagct tctcctcact ggtgccatcc gggtcgcaga caaggtggca tcggggctga gttcagtcct cgtgcactgc agtgacggct gggaccggac ggctcaactg accacgctgg ccatgctgat gctcgatggc ttctaccgca gcatcgaggg ctttgagatc ctggtgcaga aggagtggat cagcttcgga cacaagtttt catctagaat tggccacggt gacaagaacc acgcggatgc cgaccgctcc ccgattttcc tgcagttcat cgactgcgtg tggcagatga cgaagcagtt cccacagct ttcgagttca acgagtgctt cctggttgcc atcttggatc acctgtacag ctgccggttc gggactttct tactaaactg tgaggcggca cgggagagac agagactcgc agaaaggacg gtgtctgtgt ggtccctgat caacagcaac aaagacgaat tcacaaaccc gttctacgca agggagagca accgcgtgat ctacccggtc accagcgtgc gccacctgga actgtgggtg aattactaca tccggtggaa ccccaggatc cggcagcagc agccccaccc catgtagcag cgatataatg agctcctggc cctgcgtgac gattacatca agaagctgga ggagctgcag ctggccacgc ccaccaagct cactgactcc tccaccccgc cttccggttc cgcacagata gctccccgca tgcaaactca cttctgaggg ggttccgggc cccaaaccct gaataagtga cgtcaccaac ttccgttctg tgcgcttgtg caaaggggat ataaagtctc cgcctctgtg tagaagtcga actaacaccc tagaaccttg tgtgacacgt gtgagtgtgc gccttttgtg acgtgtgagt gtgcgatttg tgtgacatgt gtgaatgtgt accctgtgtg atacgtgcaa gtgtgcgcct tgtgtaaagt tcgtgagtgt gcacctcctg taacatgttt tgcaaggaat ctactgcgct tgtgtgccag tcgtgagtac agagtagggg gggtcccgga aaaatcctca cacttttta caaagcgctt gtgcaaagat taaaattaaa ttatatcaat aattatataa attattataa ttatattgca aagattaaaa agttaaattt agtttacctc tatataaatc cagacataca taatatgtac tctgtgcgct taattgaaac gttattttaa atccagaggg gagattttt ttgtaaaatg gatttttcct -continued ccagccactt attttgcaaa gataaaaaag ttaaaataaa agttaaattt aattataaaa aaaaaaaaaa aaaaaaaaaa aaaaaaaaaa aaaaaaaaaa aaaaaaaaaa aaaaaaaaaa aaaaaaaaaa aaaaaa linker sequence "GSTS"

SEQ ID NO: 10

GSTSGSGKSSEGKG

Fv3E10-GSTS-hMTM1

SEQ ID NO: 11

DIVLTQSPASLAVSLGQRATISCRASKSVSTSSYSYMHWYQQKPGQPPKLLIKYASYLESGVPAR

FSGSGSGTDFHLNIHPVEEEDAATYYCQHSREFPWTFGGGTKLELKGGGGSGGGGSGGGSEVQLV

ESGGGLVKPGGSRKLSCAASGFTFSNYGMHWVRQAPEKGLEWVAYISSGSSTIYYADTVKGRFTI

SRDNAKNTLFLQMTSLRSEDTAMYYCARRGLLLDYWGQGTTLTVSSEQKLSEELGSTSGSGKSSE

GKGMASASTSKYNSHSLENESIKRTSRDGVNRDLTEAVPRLPGETLITDKEVIYICPFNGPIKGR

VYITNYRLYLRSLETDSSLILDVPLGVISRIEKNIGGATSRGENSYGLDITKDMRNLRFALKQEG

HRRDMFEILTRYAFPLAHSLPLEAFLNEEKENVDGWTVYNPVEEYRRQGLPNHHWRITFINKCYE

LCDTYPALLVVPYRASDDDLRRVATFRSRNRIPVLSWIHPENKTVIVCSQPLVGMSGKRNKDDKY

LDVIRETNKQISKLTIYDARPSVNAVANKATGGGYESDDAYHNAELFFLDIHNIHVMRESLKKVK

DIVYPNVEESHWLSSLESTHWLEHTKLVLTGAIQVADKVSSGKSVLVHCSDGWDRTAQLTLAMLM

LDSFYRSIEGFEILVQKKWISFGHKFASRIGHGDKNHTDADRSPIFLQFIDCVWQMSKQFPTAFE

FNEQFLIIILDHLYSCRFGTFLENCESARERQKVTERTVLWSLINSNKEKEKNPFYTEINRVLYP

VASMRHLELWVNYYIRWNPRIKQQQPNPVEQRYMELLALRDEYIKRLEELQLANSAKLSDPPTSP

SSPSQMMPHVQTHFHHHHHH

Note-in SEQ ID NO: 11-linker sequences are underlined and epitope tags are double underlined

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

I claim:

1. A chimeric polypeptide comprising: (i) a myotubularin (MTM1) polypeptide, or a bioactive fragment thereof; wherein the MTM1 polypeptide comprises an amino acid sequence having at least 90% sequence identity to SEQ ID NO: 1, and (ii) an internalizing moiety, wherein the chimeric polypeptide has phosphoinositide phosphatase activity;

wherein said internalizing moiety is an antibody or antigen-binding fragment thereof, wherein said antibody or antigen-binding fragment thereof is a monoclonal antibody 3E10, or a variant thereof that retains the cell penetrating activity of 3E10, or an antigen-binding fragment of any of the foregoing.

2. The chimeric polypeptide of claim 1, wherein the MTM1 polypeptide comprises an amino acid sequence having at least 95% sequence identity to SEQ ID NO: 1.

3. The chimeric polypeptide of claim 2, wherein the MTM1 polypeptide comprises a wildtype MTM1 polypeptide.

4. The chimeric polypeptide of claim 1, wherein (i) comprises an amino acid sequence having at least 95% sequence identity to SEQ ID NO: 1.

5. The chimeric polypeptide of claim 1, wherein (i) comprises an amino acid sequence having at least 98% sequence identity to SEQ ID NO: 1.

6. The chimeric polypeptide of claim 1, wherein the internalizing moiety promotes transport of said chimeric polypeptide into muscle cells.

7. The chimeric polypeptide of claim 1 or 3, wherein said antibody or antigen-binding fragment thereof comprises a light chain variable domain that is a humanized variant of SEQ ID NO: 4, and wherein said antibody or antigen-binding fragment thereof further comprises a heavy chain variable domain that is a humanized variant of SEQ ID NO: 2.

8. The chimeric polypeptide of claim 7, wherein the internalizing moiety is a Fab'.

9. The chimeric polypeptide of claim 7, wherein the internalizing moiety is a full-length antibody.

10. The chimeric polypeptide of claim 1, wherein the internalizing moiety is a Fab'.

11. The chimeric polypeptide of claim 1, wherein the internalizing moiety is a F(ab')2 fragment.

12. The chimeric polypeptide of claim 1, wherein the internalizing moiety is a full-length antibody.

13. The chimeric polypeptide of claim 1, comprising a linker joining the MTM1 polypeptide or bioactive fragment thereof to the internalizing moiety.

14. The chimeric polypeptide of claim 13, wherein the internalizing moiety is conjugated to the N-terminal or C-terminal amino acid of the MTM1 polypeptide.

15. The chimeric polypeptide of claim 1, wherein the MTM1 polypeptide or bioactive fragment thereof is chemically conjugated to the internalizing moiety.

16. The chimeric polypeptide of claim 1, wherein the MTM1 polypeptide is expressed in bacterial cells.

17. A nucleic acid construct, comprising a nucleotide sequence that encodes a myotubularin (MTM1) polypeptide, or a bioactive fragment thereof, operably linked to a nucleotide sequence that encodes an internalizing moiety, wherein the nucleic acid construct encodes a chimeric polypeptide having phosphoinositide phosphatase activity; wherein the MTM1 polypeptide comprises an amino acid sequence having at least 90% sequence identity to SEQ ID NO: 1.

18. The nucleic acid of claim 17, wherein the MTM1 polypeptide comprises an amino acid sequence having at least 95% sequence identity to SEQ ID NO: 1.

19. The nucleic acid of claim 18, wherein the MTM1 polypeptide comprises a wildtype MTM1 polypeptide.

20. The nucleic acid of claim 19, wherein said antibody or antigen-binding fragment thereof comprises a light chain variable domain that is a humanized variant of SEQ ID NO: 4, and wherein said antibody or antigen-binding fragment thereof further comprises a heavy chain variable domain that is a humanized variant of SEQ ID NO: 2.

21. The nucleic acid of claim 17, wherein said antibody or antigen-binding fragment thereof comprises a light chain variable domain that is a humanized variant of SEQ ID NO: 4, and wherein said antibody or antigen-binding fragment thereof further comprises a heavy chain variable domain that is a humanized variant of SEQ ID NO: 2.

22. A method of delivering a chimeric polypeptide into a muscle cell, comprising contacting a muscle cell with a chimeric polypeptide, which chimeric polypeptide comprises (i) a myotubularin (MTM1) polypeptide, or a bioactive fragment thereof; wherein the MTM1 polypeptide comprises an amino acid sequence having at least 90% sequence identity to SEQ ID NO: 1, and (ii) an internalizing moiety, wherein the chimeric polypeptide has phosphoinositide phosphatase activity;

wherein said internalizing moiety is an antibody or antigen-binding fragment thereof, wherein said antibody or antigen-binding fragment thereof is a monoclonal antibody 3E10, or a variant thereof that retains the cell penetrating activity of 3E10, or an antigen-binding fragment of any of the foregoing.

23. The method of claim 22, wherein the MTM1 polypeptide comprises an amino acid sequence having at least 95% sequence identity to SEQ ID NO: 1.

24. The method of claim 23, wherein the MTM1 polypeptide comprises a wildtype MTM1 polypeptide.

25. The method of claim 24, wherein said antibody or antigen-binding fragment thereof comprises a light chain variable domain that is a humanized variant of SEQ ID NO: 4, and wherein said antibody or antigen-binding fragment thereof further comprises a heavy chain variable domain that is a humanized variant of SEQ ID NO: 2.

26. The method of claim 22, wherein said antibody or antigen-binding fragment thereof comprises a light chain variable domain that is a humanized variant of SEQ ID NO: 4, and wherein said antibody or antigen-binding fragment thereof further comprises a heavy chain variable domain that is a humanized variant of SEQ ID NO: 2.

27. The method of claim 22, wherein the cell is a skeletal muscle cell.

* * * * *